(12) United States Patent
Von Nussbaum et al.

(10) Patent No.: US 8,580,800 B2
(45) Date of Patent: Nov. 12, 2013

(54) 1,4-DIARYL-PYRIMIDOPYRIDAZINE-2,5-DIONES AND THEIR USE

(75) Inventors: Franz Von Nussbaum, Düsseldorf (DE);
Dagmar Karthaus, Solingen (DE);
Martina Delbeck, Heiligenhaus (DE);
Volkhart Min-Jian Li, Velbert (DE);
Daniel Meibom, Leverkusen (DE);
Klemens Lustig, Wuppertal (DE)

(73) Assignee: Bayer Intellectual Property GmbH, Monheim (DE)

( * ) Notice: Subject to any disclaimer, the term of this patent is extended or adjusted under 35 U.S.C. 154(b) by 0 days.

(21) Appl. No.: 12/991,346

(22) PCT Filed: Apr. 24, 2009

(86) PCT No.: PCT/EP2009/003006
§ 371 (c)(1),
(2), (4) Date: Jan. 26, 2011

(87) PCT Pub. No.: WO2009/135599
PCT Pub. Date: Nov. 12, 2009

(65) Prior Publication Data
US 2011/0118221 A1 May 19, 2011

(30) Foreign Application Priority Data
May 7, 2008 (DE) .......................... 10 2008 022 521

(51) Int. Cl.
*A01N 43/90* (2006.01)
*A61K 31/519* (2006.01)
*C07D 475/00* (2006.01)

(52) U.S. Cl.
USPC ......... 514/262.1; 544/255; 544/256; 544/257

(58) Field of Classification Search
USPC .................. 544/255, 256, 257; 514/262.1
See application file for complete search history.

(56) References Cited

FOREIGN PATENT DOCUMENTS

| | | |
|---|---|---|
| WO | 2004024700 A1 | 3/2004 |
| WO | 2004024701 A1 | 3/2004 |
| WO | 2005082863 A2 | 9/2005 |
| WO | 2005082864 A1 | 9/2005 |
| WO | 2006082412 A2 | 8/2006 |
| WO | 2006136857 A1 | 12/2006 |
| WO | 2007042815 A1 | 4/2007 |
| WO | 2007129060 A1 | 11/2007 |
| WO | 2008030158 A1 | 3/2008 |

OTHER PUBLICATIONS

Vippagunta et al.*
Stockley et al., Am. J. Respir. Crit. Care Med. 1999, vol. 160, 49-52.
Humbert et al., J. Am. Coll. Cardiol. 2004, vol. 43, 13S-24S.
D'Alonzo et al., Ann. Intern. Med. 1991, vol. 115, 343-349.
Ghofrani et al., herz 2005, vol. 30, 296-302.
Rosenzweig, Expert Opin. Emerging Drugs 2006, vol. 11, 609-619.
Ito et al., Curr. Med. Chem. 2007, vol. 14, 719-733.
Rabinovitch et al., Lab. Invest. 1986, vol. 55, 632-653.
Todorovich-Hunter et al., Am. Rev. Respir. Dis. 1992, vol. 146, 213-223.
Rabonivitch et al., Am. J. Physiol. 1999, vol. 277, L5-L12.
Zaidi et al., Circulation 2002, vol. 105, 516-521.
Cowan et al., Nature Med. 2000, vol. 6, 698-702.
Simonneau et al., J. Am. Coll. Cardiol. 2004, vol. 43, 5S-12S.
Gadek et al., J. Clin. Invest. 1981, vol. 68, 889-898.
Werb et al., J. Invest. Dermatol. 1982, vol. 79, 154-159.
Janoff et al., Am. Rev. Respir. Dis. 1985, vol. 132, 417-433.
Barnes et al., N. Engl. J. Med. 2000, vol. 343, 269-280.
Liou et al., Biochemistry 1995, vol. 34, Nr. 49, 16171-16177.
Luhr et al., Am. J. Respir. Crit. Care Med. 1999, vol. 159, 1849-1861.
Chollet-Martin et al., Am. J. Respir. Crit. Care Med. 1996, 154, 594-601.

* cited by examiner

*Primary Examiner* — Paul V. Ward
(74) *Attorney, Agent, or Firm* — Karen B. King

(57) ABSTRACT

The present invention relates to novel 1,4-diarylpyrimido[4,5-d]pyridazine-2,5-dione derivatives, to processes for their preparation, to their use alone or in combination for the treatment and/or prevention of diseases and also to their use for preparing medicaments for the treatment and/or prevention of diseases, in particular for the treatment and/or prevention of disorders of the lung and the cardiovascular system.

9 Claims, No Drawings

1,4-DIARYL-PYRIMIDOPYRIDAZINE-2,5-DIONES AND THEIR USE

The present invention relates to novel 1,4-diarylpyrimido[4,5-d]pyridazine-2,5-dione derivatives, to processes for their preparation, to their use alone or in combination for the treatment and/or prevention of diseases and also to their use for preparing medicaments for the treatment and/or prevention of diseases, in particular for the treatment and/or prevention of disorders of the lung and the cardiovascular system.

Human leukocyte elastase (HLE, EC 3.4.21.37), also called human neutrophil elastase (HNE, hNE), belongs to the family of the serine proteases. The proteolytic enzyme is found in the azurophilic granules of polymorphonuclear leukocytes (PMN leukocytes). Intracellular elastase performs an important function in defense against pathogens by breaking down the foreign particles taken by phagocytosis. Activated neutrophilic cells release the HNE from the granules into the extracellular space (extracellular HNE), with some of the released HNE remaining on the outside of the neutrophilic cell membrane (membrane-associated HNE). The highly active enzyme is able to break down a large number of connective tissue proteins, for example the proteins elastin, collagen and fibronectin. Elastin occurs in high concentrations in all tissue types showing high elasticity, for example in the lung and the arteries. HNE is involved in the tissue breakdown and transformation (tissue remodeling) associated with a large number of pathological processes (for example tissue injuries). HNE is also an important modulator of inflammatory processes. HNE induces for example increased interleukin-8 (IL-8) gene expression.

Accordingly, it is presumed that HNE plays an important role in many disorders, injuries and pathological changes whose formation and/or progression are/is associated with inflammatory events and/or proliferative and hypertrophic tissue and vessel transformation. This can be in particular disorders and/or injuries of the lung or the cardiovascular system, or it may be sepsis, cancerous disorders or other inflammatory disorders.

Disorders and injuries of the lung which may be mentioned in this context are in particular chronic obstructive pulmonary disease (COPD), acute respiratory distress syndrome (ARDS), cystic fibrosis (CF; also referred to as mucoviscidosis), lung emphysema and acute lung injury (ALI). Disorders and injuries of the cardiovascular system where HNE is involved are, for example, tissue transformations during heart failure and reperfusion damage after acute myocardial infarction (AMI), cardiogenic shock, acute coronary syndrome (ACS), and also aneurysms. Disorders associated with sepsis are, for example, systemic inflammatory response syndrome (SIRS), severe sepsis, septic shock and multi-organ failure (MOF; multi-organ dysfunction, MODS) and also disseminated intravascular coagulation (DIC). Examples of tissue breakdown and transformation in cancerous processes are the migration of cancer cells into healthy tissue (formation of metastases) and the formation of new supply blood vessels (neo-angiogenesis). Other inflammatory diseases where HNE plays a role are rheumatoid disorders, for example rheumatoid arthritis, inflammatory bowel disease (IBD), Crohn's disease (CD); ulcerative colitis (UC) and arteriosclerosis.

It is generally assumed that elastase-mediated pathological processes are based on a displaced equilibrium between free elastase and endogenous elastase inhibitor protein (mainly alpha-1 antitrypsin, AAT) [*Neutrophils and protease/antiprotease imbalance*, Stockley, *Am. J. Respir. Crit. Care Med.* 160, 49-52 (1999)]. AAT is present in large excess in the plasma and thus very rapidly neutralizes free HNE. The concentration of free elastase is elevated in various pathological processes, so that there is a local shift in the balance between protease and protease inhibitor in favor of the protease. In addition, membrane-associated elastase of the activated PMN cells is very substantially protected from inhibition by AAT. The same applies to free elastase, which is located in a microcompartment which is difficult to access between the neutrophilic cell and the adjoining tissue cell (for example endothelial cell). In addition, strong oxidizing conditions prevail in the vicinity of activated leukocytes (oxidative burst), and thus AAT is oxidized and loses several orders of magnitude in the inhibitory effect.

Novel elastase-inhibiting active compounds (exogenously administered inhibitors of HNE) ought accordingly to have a low molecular weight in order to be able also to reach and inhibit the membrane-associated HNE and the HNE present in the protected microcompartment (see above). Also necessary for this purpose is good in vivo stability of the substances (low in vivo clearance). In addition, these compounds ought to be stable under oxidative conditions in order not to lose inhibitory power in the pathological process.

Pulmonary arterial hypertension (PAH) is a progressive lung disorder which, untreated, leads to death on average within 2.8 years after being diagnosed. An increasing constriction of the pulmonary circulation leads to increased stress on the right heart, which may develop into right heart failure. By definition, the mean pulmonary aterial pressure (mPAP) in case of chronic pulmonary hypertension is >25 mmHg at rest or >30 mmHg during exertion (normal value <20 mmHg). The pathophysiology of pulmonary arterial hypertension is characterized by vasoconstriction and remodeling of the pulmonary vessels. In chronic PAH there is neomuscularization of initially unmuscularized pulmonary vessels, and the vascular muscles of the already muscularized vessels increase in circumference. This increasing obliteration of the pulmonary circulation results in progressive stress on the right heart, which leads to a reduced output from the right heart and eventually ends in right heart failure (M. Humbert et al., *J. Am. Coll. Cardiol.* 2004, 43, 13S-24S). PAH is an extremely rare disorder, with a prevalence of 1-2 per million. The average age of the patients has been estimated to be 36 years, and only 10% of the patients were over 60 years of age. Distinctly more women than men are affected (G. E. D'Alonzo et al., *Ann. Intern. Med.* 1991, 115, 343-349).

Despite all the advances in the therapy of pulmonary arterial hypertension there is as yet no prospect of cure of this serious disorder. Standard therapies available on the market (for example prostacyclin analogs, endothelin receptor antagonists, phosphodiesterase inhibitors) are able to improve the quality of life, the exercise tolerance and the prognosis of the patients. The principles of these therapies are primarily hemodynamic, influencing vessel tone but having no direct influence on the pathogenic remodeling processes. In addition, the possibility of using these medicaments is restricted through the sometimes serious side effects and/or complicated types of administration. The period over which the clinical situation of the patients can be improved or stabilized by specific monotherapy is limited (for example owing to the development of tolerance). Eventually the therapy escalates and thus a combination therapy is applied, where a plurality of medicaments must be given concurrently.

Novel combination therapies are one of the most promising future therapeutic options for the treatment of pulmonary arterial hypertension. In this connection, the finding of novel pharmacological mechanisms for the treatment of PAH is of particular interest (Ghofrani et al., Herz 2005, 30, 296-302; E. B. Rosenzweig, *Expert Opin. Emerging Drugs* 2006, 11, 609-619; T. Ito et al., *Curr. Med. Chem.* 2007, 14, 719-733). Therapeutic options which intervene directly in the remodeling event (antiremodeling mechanisms reverse remodeling mechanisms) in particular might form the basis for a more causal treatment and thus be of great advantage for the patients. In this connection, it will be possible to combine known and novel therapies. In order to minimize the risk of interfering medicament-medicament interactions in such a combination therapy, these novel active compounds ought to inhibit metabolizing P450 CYP enzymes only to a very small extent or not at all.

These days, one proceeds on the assumption that elastase plays a central role in pathological remodeling. It has been possible to find a fragmentation of connective tissue (internal elastic lamina) in animal models and in patients with elevated pulmonary arterial blood pressure (pulmonary arterial hypertension) [Rabinovitch et al., *Lab. Invest.* 55, 632-653 (1986)], and it was possible to show in animal models of pulmonary arterial hypertension (hypoxic rat and mouse model, monocrotaline rat model) that elastase activity was increased and was associated with the fragmentation of connective tissue [Todorovich-Hunter et al., *Am. Rev. Respir. Dis.* 146, 213-223 (1992)]. It is suspected that the tissue remodeling to be observed during the disease process of pulmonary arterial hypertension is induced by an elastase-mediated release of connective tissue-associated growth factors, for example of basic fibroblast growth factor (bFGF) [Rabinovitch, *Am. J. Physiol.* 277, L5-L12 (1999)]. It was possible to show a positive effect with an overexpressed elastase inhibitor protein in the hypoxic mouse model of pulmonary arterial hypertension [Zaidi et al., *Circulation* 105, 516-521 (2002)]. It was possible to show a positive effect with synthetic low-molecular-weight elastase inhibitors in the monocrotaline rat model of pulmonary arterial hypertension; in this case a beneficial effect on tissue remodeling was also to be noted [Cowan et al., *Nature Med.* 6, 698-702 (2000)]. However, all previously disclosed low-molecular-weight elastase inhibitors have low selectivity, are chemically reactive and/or have only limited oral availability, thus to date thwarting clinical development of an oral elastase inhibitor for these indications.

The term "pulmonary arterial hypertension" includes particular types of pulmonary hypertension as have been specified for example by the World Health Organization (WHO) (*Clinical Classification of Pulmonary Hypertension*, Venice 2003; G. Simonneau et al., *J. Am. Coll. Cardiol.* 2004, 43, 5S-12S).

According to this classification, pulmonary arterial hypertension includes idiopathic pulmonary arterial hypertension (IPAH, formerly also called primary pulmonary hypertension, PPH), familial pulmonary arterial hypertension (FPAH), persistent pulmonary hypertension in neonates and also associated pulmonary arterial hypertension (APAH) which is associated with collagenoses, congenital systemic-pulmonary shunt vitiae, portal hypertension, HIV infections, intake of particular drugs and medicaments (for example anorectics), with disorders having a significant venous/capillary involvement, such as pulmonary venal-occlusive disease and pulmonary capillary hemangiomatosis, or with other disorders such as thyroid disorders, glycogen storage diseases, Gaucher's disease, hereditary teleangiectasia, hemoglobinopathies, myeloproliferative disorders and splenectomy.

Other types of pulmonary hypertension include, for example, the pulmonary hypertension associated with left heart disorders, for example with ventricular or valvular disorders, the pulmonary hypertension associated with disorders of the respiratory tract and/or of the lungs, for example with chronic obstructive lung disease, interstitial lung disease or pulmonary fibrosis, the pulmonary hypertension attributable to chronic thrombotic and/or embolic disorders, for example associated with thromboembolic obstruction of pulmonary arteries, and the pulmonary hypertension caused by generally inflammatory disease processes or by special causes (for example associated with schistosomiasis, sarcoidosis and neoplastic diseases).

Chronic obstructive pulmonary disease (COPD) is a pulmonary disease which progresses slowly and is characterized by obstruction of breathing caused by pulmonary emphysema and/or chronic bronchitis. First symptoms of the disorder generally appear from the fourth to the fifth decade of life onwards. In the years that follow, the short breath frequently worsens and a cough, associated with extensive and sometimes prolonged discharge and obstructed breathing up to breathlessness (dyspnea), manifests itself. COPD is primarily a smoker's disease: smoking is responsible for 90% of all cases of COPD and 80-90% of all deaths caused by COPD. COPD is a major medical problem and represents the sixth most frequent cause of death world-wide. About 4-6% of people over the age of 45 are affected.

Although the obstruction of breathing may only be partial and temporal, COPD cannot be cured. Accordingly, the target of the treatment is to improve the quality of life, to ameliorate the symptoms, to prevent acute worsening and to slow the progressive impairment of pulmonary function. Existing pharmacotherapies, which have hardly changed over the last two to three decades, are the use of bronchodilators to open up blocked respiratory paths, and in certain situations corticosteroids to control the inflammation of the lung [P. J. Barnes, *N. Engl. J. Med.* 343, 269-280 (2000)]. The chronic inflammation of the lung, caused by cigarette smoke or other irritants, is the force behind the development of the disease. The mechanism on which it is based involves immune cells which, during the course of the inflammatory reaction of the lung, secrete various chemokines. This attracts neutrophilic cells and subsequently alveolar macrophages to the connective tissue of the lung and the lumen. Neutrophilic cells secrete a protease cocktail which contains mainly HNE and protease 3. This causes the local protease/antiprotease balance to shift in favor of the proteases, resulting inter alia in an unchecked elastase activity and as a consequence thereof an excess degradation of the elastins of the alveolar cells [J. E. Gadek et al., *J. Clin. Invest.* 68, 889-898 (1981); Z. Werb et al., *J. Invest. Dermatol.* 79, 154-159 (1982); A. Janoff, *Am. Rev. Respir. Dis.* 132, 417-433 (1985); P. J. Barnes, *N. Engl. J. Med.* 343, 269-280 (2000)]. This tissue degradation causes the bronchii to collapse. This is associated with a reduced elasticity of the lung, which leads to obstructed breathing and impaired respiration. In addition, frequent and persistent inflammation of the lung may lead to remodeling of the bronchii and as a consequence to the formation of lesions. Such lesions contribute to chronic cough, which characterizes chronic bronchitis.

Alpha-1 antitrypsin (AAT) is a small endogenous protein and represents, as mentioned above, the most important endogenous elastase inhibitor. In patients having a genetic deficiency of this protein (AADT), the protease/antiprotease balance is shifted. Accordingly, in AADT patients, the effective radius and the duration of action of HNE is increased by a factor of 2.5 and 6.5, respectively [T. G. Liou and E. J. Campbell, *Biochemistry* 1995, 16171-16177]. AADT patients have an increased risk of developing pulmonary emphysema or COPD, and in many AADT patients a lung transplant is indicated.

Bronchiectasis is understood as an abnormal dilation of the bronchial tree. Two forms may be distinguished: sack-shaped localized bronchiectases and generalized, cylindrical bronchiectases. Bronchiectases may be congenital; however, in most cases they are acquired and are found in particular in smokers. Owing to the dilation, drainage of the bronchial secretions is rendered more difficult, and the retained bronchial secretions promote infections. Frequently, bronchiectases are also encountered in the case of congenital disorders of the mucosa such as mucoviscidosis with abnormal viscosity of the bronchial secretions and in the case of ciliary dyskinesia syndrome. In the case of this syndrome (Kartagener syndrome), the architecture and function of the cilia and thus drainage of the secretions are impaired. Other causes of bronchiectases may be obstructions proximal to the ectasis, for example by tumours or foreign bodies. Recurrent and persisting infections weakening the bronchial walls are also thought to be causal. Furthermore, there are bronchiectasias which can not be connected unambiguously to states of infection or exogenic noxa (idiopathic bronchiectasias).

Bronchiectasia is characterized by migration of neutrophils into the pulmonary tissue. The patients show a marked imbalance between neutrophilic activity and protective inhibitor proteins, resulting in damage to the pulmonary tissue by the proteases (mainly HNE) secreted by the neutrophils [Schaaf et al., Respiration 67, 52-59 (2000)].

Bronchiolitis obliterans is an inflammation of the bronchioli with destruction of the epithelium and formation of a fibrin-rich exudate in the bronchioli and the neighbouring alveoli. Organization of the exudate results in plugs of connective tissue reaching from the bronchioli into the alveoli. The disease is characterized by an increased number of neutrophils in the respiratory tract and an imbalance between free elastase and the endogenous elastase inhibitor protein [Elssner et al., Transpl. Infect. Dis. 3, 168-176 (2001)] Prior infections and medicaments are being discussed as possible causes. The disease may also occur in the context of a transplant rejection.

Acute lung injury (ALI) and the more pronounced form thereof, acute respiratory distress syndrome (ARDS), are serious disorders associated with a mortality of 50-60%. According to the definition of the North American-European Consensus Conference (NAECC) of 1994, ALI and ARDS are defined by an acute onset, bilateral radiologically visible infiltrates, a $PaO_2/FiO_2$ index of $\leq 300$ mmHg (ALI) or $\leq 200$ mmHg (ARDS), a pulmonary capillary wedge pressure of <18 mmHg and no clinical evidence of left atrial hypertension.

The development of acute lung injury may be preceded both by pulmonary and extrapulmonary disorders. Aspiration of stomach content, pneumonias, smoke poisoning, pulmonary contusion and near-drowning are considered to be lung-specific predisposing factors. In particular the aspiration of stomach content and pneumonias are frequently seen as initial disorders of ALI/ARDS of pulmonary origin. The most frequent indirect events are polytrauma, sepsis, repeated blood transfusions, acute pancreatitis and burns. The incidence is 17.9 cases of ALI and 13.5 cases of ARDS per 100 000 inhabitants and year [Luhr et al., Am. J. Respir. Crit. Care Med. 159, 1849-1861 (1999)].

A central role in the development of these disorders is played by the massive inflammatory changes in the lung, which are triggered by a widely branched system of mediators. An important role in the development of lung injury is also played by neutrophilic granulocytes, the number of which increases permanently during the inflammatory process [Chollet-Martin et al., Am. J. Respir. Crit. Care Med. 154, 594-601 (1996)]. The action of the mediators causes damage to the alveolocapillary membranes, and this results in an increased permeability of the alveolar capillary barrier. Owing to the increased permeability, protein-rich fluid can permeate into the alveolae and also into the interstitial space; a low-pressure pulmonary edema develops. Characteristic for ALI/ARDS, this is a noncardiogenic edema. The edema fluid contains mainly fibrin, erythrocytes, leukocytes, hyaline membranes and other proteins. Together with the products of activated neutrophils, the protein-rich exudate leads to dysfunction of the surfactant. The inflammatory processes cause damage and loss of pneumocytes of type II, which form surfactant, resulting in a reduced surfactant production. The surfactant deficit increases the surface tension in the alveolae; the alveolae collapse and atelectases are formed. With perfusion being maintained, there is thus a ventilation/perfusion imbalance resulting in an increase of the pulmonary right-left shunt. Furthermore, compliance is reduced, and in contrast the alveolar dead space is increased because there are areas which are ventilated but, owing to pulmonary hypertension, no longer sufficiently perfused.

An increased elastase activity, which correlates to the severity of the lung injury, could be measured in the bronchoalveolar lavage fluid (BALF) of ARDS patients. In animal models where the lung is injured (for example by administration of LPS), this effect can be reproduced. Here, treatment with elastase inhibitors (for example sivelestat or elafin, vide infra,) reduces the elastase activity in the BALF considerably and improves lung function.

In Japan and South Korea, an elastase inhibitor (sivelestat, Elaspol®) is approved for the treatment of acute lung injury associated with SIRS. The reversible, but reactive compound has only a relatively weak effect on HNE ($K_i$ 200 nM) and also acts on the pancreas elastase ($IC_{50}$ 5.6 µM). The active compound is administered intravenously, oral administration is not possible.

Elafin and structural analogs are also investigated as therapeutically useful elastase inhibitors. Elafin is an endogenous small protein which inhibits both elastase and proteinase 3. However, owing to the proteinergic character, oral administration of elafin is not possible.

It is an object of the present invention to provide novel substances acting as low-molecular-weight, non-reactive and selective inhibitors of human neutrophil elastase (HNE), which are suitable as such for the treatment and/or prevention in particular of pulmonary disorders and disorders of the cardiovascular system.

WO 2004/024700, WO 2004/024701, WO 2005/082863, WO 2005/082864 and WO 2008/003412 disclose various 1,4-diaryldihydropyrimidin-2-one derivatives as HNE inhibitors for the treatment of chronic obstructive pulmonary disease, acute coronary syndrome, myocardial infarction and heart failure. Di- and multimers of such compounds for the treatment of respiratory disorders are claimed in WO 2006/082412, WO 2006/136857, WO 2007/042815 and WO 2008/030158. 4-Aryldihydropyrimidin-2-one derivatives as inhibitors of the calcium channel function for the treatment of hypertension are described in WO 2005/009392. WO 2007/129060 and WO 2008/135537 disclose tetrahydropyrrolopyrimidinediones and multimers thereof as HNE inhibitors.

Surprisingly, it has now been found that certain 1,4-diarylpyrimido[4,5-d]pyridazine-2,5-dione derivatives are particularly suitable for the treatment and/or prevention of disorders. These compounds described below are low-molecular-weight, non-reactive and selective inhibitors of human neutrophil elastase (HNE) which additionally have advantageous pharmacokinetic properties with respect to their bioavailability, half-life and/or protein binding. Accordingly, these substances are promising starting points for novel medicaments for the treatment and/or prevention of in particular disorders of the lung and the cardiovascular system.

The present invention provides compounds of the general formula (I)

$$\text{(I)}$$

in which

A represents CH or N, $R^1$ represents hydrogen, halogen, cyano, nitro, $(C_1$-$C_6)$-alkyl, difluoromethyl, trifluoromethyl, $(C_1$-$C_6)$-alkoxy, difluoromethoxy, trifluoromethoxy, amino, mono- or di-$(C_1$-$C_6)$-alkyl-amino
or
represents a group of the formula —NH—C(=O)—$R^6$, —NH—C(=O)—NH$R^6$, —NH—SO$_2$—$R^7$ or —S(O)$_n$—$R^8$ in which
$R^6$ represents hydrogen or $(C_1$-$C_6)$-alkyl,
$R^7$ represents $(C_1$-$C_6)$-alkyl,
$R^8$ represents $(C_1$-$C_6)$-alkyl which may be substituted by hydroxyl, $(C_1$-$C_4)$-alkoxy, amino, mono- or di-$(C_1$-$C_4)$-alkylamino, hydroxycarbonyl, aminocarbonyl, $(C_3$-$C_6)$-cycloalkyl or phenyl, or represents $(C_2$-$C_6)$-alkenyl, $(C_3$-$C_6)$-cycloalkyl or phenyl,
where the $(C_3$-$C_6)$-cycloalkyl groups mentioned may be substituted up to two times by identical or different substituents from the group consisting of $(C_1$-$C_4)$-alkyl, hydroxyl and $(C_1$-$C_4)$-alkoxy
and
the phenyl groups mentioned may be substituted up to two times by identical or different substituents from the group consisting of fluorine, chlorine, cyano, $(C_1$-$C_4)$-alkyl, difluoromethyl, trifluoromethyl, $(C_1$-$C_4)$-alkoxy, difluoromethoxy and trifluoromethoxy,
and
n represents the number 0, 1 or 2, $R^2$ represents hydrogen, represents $(C_1$-$C_6)$-alkyl or $(C_2$-$C_6)$-alkenyl, each of which may be substituted up to three times by fluorine, or represents phenyl, pyridyl or pyrimidinyl,
where phenyl, pyridyl and pyrimidinyl for their part may be substituted up to two times by identical or different substituents from the group consisting of fluorine, chlorine, cyano, $(C_1$-$C_4)$-alkyl, trifluoromethyl, $(C_1$-$C_4)$-alkoxy and trifluoromethoxy,
or
$R^2$ represents a group of the formula —C(=O)—O—$R^9$, -$L^1$-C(=O)—O—$R^{10}$, -$L^2$-C(=O)—NR$^{11}$R$^{12}$, -$L^2$-SO$_2$—NR$^{11}$R$^{12}$, -$L^2$-C(=O)—NR$^{13}$—NR$^{11}$R$^{12}$ or -$L^2$-SO$_2$—$R^{14}$ in which
$L^1$ represents $(C_1$-$C_6)$-alkanediyl,
$L^2$ represents a bond or $(C_1$-$C_6)$-alkanediyl,
$R^9$ represents $(C_1$-$C_6)$-alkyl,
$R^{10}$ represents hydrogen or $(C_1$-$C_6)$-alkyl,
$R^{11}$ and 12 are identical or different and independently of one another represent hydrogen, $(C_1$-$C_6)$-alkyl, $(C_3$-$C_6)$-cycloalkyl or 4- to 6-membered heterocyclyl,
where $(C_1$-$C_6)$-alkyl, $(C_3$-$C_6)$-cycloalkyl and 4- to 6-membered heterocyclyl for their part may be substituted up to two times by identical or different substituents from the group consisting of fluorine, hydroxyl, $(C_1$-$C_4)$-alkoxy, oxo, amino, mono- or di-$(C_1$-$C_4)$-alkylamino, hydroxycarbonyl, $(C_1$-$C_4)$-alkoxycarbonyl and aminocarbonyl and where in $(C_1$-$C_6)$-alkyl a CH$_2$ group may be exchanged for an oxygen atom if this results in a chemically stabile compound
or
$R^{11}$ and $R^{12}$ together with the nitrogen atom to which they are attached form a 4- to 6-membered heterocycle which may contain a further ring heteroatom from the group consisting of N, O, S, SO and SO$_2$ and which may be substituted up to two times by identical or different substituents from the group consisting of $(C_1$-$C_4)$-alkyl, hydroxyl, $(C_1$-$C_4)$-alkoxy, oxo, amino, mono- and di-$(C_1$-$C_4)$-alkylamino,
where $(C_1$-$C_4)$-alkyl for its part may be substituted by hydroxyl or $(C_1$-$C_4)$-alkoxy,
$R^{13}$ represents hydrogen or $(C_1$-$C_4)$-alkyl
and
$R^{14}$ represents $(C_1$-$C_6)$-alkyl, $(C_3$-$C_6)$-cycloalkyl, phenyl or 5- or 6-membered heteroaryl,
where $(C_1$-$C_6)$-alkyl may be substituted by fluorine, chlorine, hydroxyl, $(C_1$-$C_4)$-alkoxy, mono- or di-$(C_1$-$C_4)$-alkylamino
and
phenyl and 5- or 6-membered heteroaryl for their part may be substituted up to two times by identical or different substituents from the group consisting of fluorine, chlorine, cyano, $(C_1$-$C_4)$-alkyl, trifluoromethyl, $(C_1$-$C_4)$-alkoxy and trifluoro-methoxy, $R^3$ represents $(C_1$-$C_6)$-alkyl or $(C_2$-$C_6)$-alkenyl, each of which may be substituted by hydroxyl, $(C_1$-$C_4)$-alkoxy, amino, mono- or di-$(C_1$-$C_4)$-alkylamino, hydroxycarbonyl, $(C_1$-$C_4)$-alkoxycarbonyl, aminocarbonyl or mono- or di-$(C_1$-$C_4)$-alkylaminocarbonyl,
or
represents a group of the formula -$L^3$-$R^{15}$ in which
$L^3$ represents a bond or $(C_1$-$C_4)$-alkanediyl
and
$R^{15}$ represents $(C_3$-$C_7)$-cycloalkyl, 4- to 7-membered heterocyclyl, phenyl or 5- or 6-membered heteroaryl,
where $(C_3$-$C_7)$-cycloalkyl and 4- to 7-membered heterocyclyl for their part may be substituted up to two times by identical or different substituents from the group consisting of $(C_1$-$C_4)$-alkyl, oxo, hydroxyl and $(C_1$-$C_4)$-alkoxy
and
phenyl and 5- or 6-membered heteroaryl for their part may be substituted up to two times by identical or different substituents from the group consisting of fluorine, chlorine, cyano, $(C_1$-$C_4)$-alkyl, trifluoromethyl, $(C_1$-$C_4)$-alkoxy, trifluoromethoxy and amino, $R^4$ represents nitro or trifluoromethyl
and
$R^5$ represents hydrogen, fluorine or chlorine,
and their salts, solvates and solvates of the salts.

Compounds according to the invention are the compounds of the formula (I) and the salts, solvates and solvates of the salts thereof, the compounds of the formulae mentioned hereinafter and encompassed by formula (I) and the salts, solvates and solvates of the salts thereof, and the compounds which are mentioned hereinafter as exemplary embodiments and encompressed by formula (I) and the salts, solvates and solvates of the salts thereof, insofar as the compounds encompassed by formula (I) and mentioned hereinafter are not already salts, solvates and solvates of the salts.

The compounds according to the invention may, depending on their structure, exist in stereoisomeric forms (enantiomers, diastereomers). The present invention therefore relates to the enantiomers and diastereomers and also to their respective mixtures. The stereoisomerically pure constituents can be isolated in a known manner from such mixtures of enantiomers and/or diastereomers.

If the compounds according to the invention may occur in tautomeric forms, the present invention encompasses all tautomeric forms.

Salts which are preferred for the purposes of the present invention are physiologically acceptable salts of the compounds according to the invention. Also encompassed are salts which are themselves unsuitable for pharmaceutical uses but can be used for example for isolating or purifying the compounds according to the invention.

Physiologically acceptable salts of the compounds according to the invention include acid addition salts of mineral acids, carboxylic acids and sulphonic acids, for example salts of hydrochloric acid, hydrobromic acid, sulphuric acid, phosphoric acid, methanesulphonic acid, ethanesulphonic acid, toluenesulphonic acid, benzenesulphonic acid, naphthalenedisulphonic acid, acetic acid, trifluoroacetic acid, propionic acid, lactic acid, tartaric acid, malic acid, citric acid, fumaric acid, maleic acid and benzoic acid.

Physiologically acceptable salts of the compounds according to the invention also include salts of conventional bases such as, by way of example and preferably, alkali metal salts (for example sodium salts and potassium salts), alkaline earth metal salts (for example calcium salts and magnesium salts) and ammonium salts derived from ammonia or organic amines having 1 to 16 carbon atoms, such as, by way of example and preferably, ethylamine, diethylamine, triethylamine, ethyldiisopropylamine, monoethanolamine, diethanolamine, triethanolamine, dicyclohexylamine, dimethylaminoethanol, procaine, dibenzylamine, N-methylmorpholine, arginine, lysine, ethylenediamine and N-methylpiperidine.

Solvates refers for the purposes of the invention to those forms of the compounds according to the invention which form, in the solid or liquid state, a complex by coordination with solvent molecules. Hydrates are a specific form of solvates in which the coordination takes place with water. Hydrates are preferred solvates in the context of the present invention.

The present invention additionally encompasses prodrugs of the compounds of the invention. The term "prodrugs" encompasses compounds which themselves may be biologically active or inactive, but are converted during their residence time in the body into compounds according to the invention (for example by metabolism or hydrolysis).

In the context of the present invention, the substituents have the following meaning, unless specified otherwise:

($C_1$-$C_6$)-Alkyl and ($C_1$-$C_4$)-alkyl stand for the purposes of the invention for a straight-chain or branched alkyl radical having respectively 1 to 6 and 1 to 4 carbon atoms. A straight-chain or branched alkyl radical having 1 to 4 carbon atoms is preferred. Examples which may be preferably mentioned are: methyl, ethyl, n-propyl, isopropyl, n-butyl, isobutyl, sec-butyl, tert-butyl, 1-ethylpropyl, n-pentyl, neopentyl and n-hexyl.

($C_1$-$C_6$)-Alkanediyl and ($C_1$-$C_4$)-alkanediyl stand for the purposes of the invention for a straight-chain or branched divalent alkyl radical having respectively 1 to 6 and 1 to 4 carbon atoms. A straight-chain or branched alkanediyl radical having 1 to 4 carbon atoms is preferred. Examples which may be preferably mentioned are: methylene, ethane-1,2-diyl (1,2-ethylene), ethane-1,1-diyl, propane-1,3-diyl (1,3-propylene), propane-1,1-diyl, propane-1,2-diyl, propane-2,2-diyl, butane-1,4-diyl (1,4-butylene), butane-1,2-diyl, butane-1,3-diyl, butane-2,3-diyl, pentane-1,5-diyl (1,5-pentylene), pentane-2,4-diyl, 3-methylpentane-2,4-diyl and hexane-1,6-diyl (1,6-hexylene).

($C_2$-$C_6$)-Alkenyl and ($C_2$-$C_4$)-alkenyl stand for the purposes of the invention for a straight-chain or branched alkenyl radical having respectively 2 to 6 and 2 to 4 carbon atoms and a double bond. A straight-chain or branched alkenyl radical having 2 to 4 carbon atoms is preferred. Examples which may be preferably mentioned are: vinyl, allyl, isopropenyl, n-but-2-en-1-yl, n-but-3-en-1-yl, n-pent-2-en-1-yl, n-pent-3-en-1-yl, n-pent-4-en-1-yl, 3-methylbut-2-en-1-yl and 4-methylpent-3-en-1-yl.

($C_1$-$C_6$)-Alkoxy and ($C_1$-$C_4$)-alkoxy stand for the purposes of the invention for a straight-chain or branched alkoxy radical having respectively 1 to 6 and 1 to 4 carbon atoms. A straight-chain or branched alkoxy radical having 1 to 4 carbon atoms is preferred. Examples which may be preferably mentioned are: methoxy, ethoxy, n-propoxy, isopropoxy, n-butoxy, isobutoxy, sec-butoxy, tert-butoxy, 1-ethylpropoxy, n-pentoxy, neopentoxy and n-hexoxy.

($C_1$-$C_4$)-Alkoxycarbonyl stands for the purposes of the invention for a straight-chain or branched alkoxy radical having 1 to 4 carbon atoms which is attached via a carbonyl group. Examples which may be preferably mentioned are: methoxycarbonyl, ethoxycarbonyl, n-propoxycarbonyl, isopropoxycarbonyl, n-butoxycarbonyl and tert-butoxycarbonyl.

Mono-($C_1$-$C_6$)-alkylamino and mono-($C_1$-$C_4$)-alkylamino stand for the purposes of the invention for an amino group having a straight-chain or branched alkyl substituent having respectively 1 to 6 and 1 to 4 carbon atoms. A straight-chain or branched monoalkylamino radical having 1 to 4 carbon atoms is preferred. Examples which may be preferably mentioned are: methylamino, ethylamino, n-propylamino, isopropylamino, n-butylamino, tert-butylamino, n-pentylamino and n-hexylamino.

Di-($C_1$-$C_6$)-alkylamino and di-($C_1$-$C_4$)-alkylamino stand for the purposes of the invention for an amino group having two identical or different straight-chain or branched alkyl substituents having in each case respectively 1 to 6 and 1 to 4 carbon atoms. A straight-chain or branched dialkylamino radical having in each case 1 to 4 carbon atoms is preferred. Examples which may be preferably mentioned are: N,N-dimethylamino, N,N-diethylamino, N-ethyl-N-methylamino, N-methyl-N-n-propylamino, N-isopropyl-N-methylamino, N-isopropyl-N-n-propylamino, N,N-diisopropylamino, N-n-butyl-N-methylamino, N-tert-butyl-N-methylamino, N-methyl-N-n-pentylamino and N-n-hexyl-N-methylamino.

Mono- and di-($C_1$-$C_4$)-alkylaminocarbonyl stand for the purposes of the invention for an amino group which is attached via a carbonyl group and has respectively one straight-chain or branched and two identical or different straight-chain or branched alkyl substituents having in each case 1 to 4 carbon atoms. Examples which may be preferably mentioned are: methylaminocarbonyl, ethyl-aminocarbonyl, n-propylaminocarbonyl, isopropylaminocarbonyl, n-butylaminocarbonyl, tert-butylaminocarbonyl, N,N-dimethylaminocarbonyl, N,N-diethylaminocarbonyl, N-ethyl-N-methyl-aminocarbonyl, N-methyl-N-n-propylaminocarbonyl, N-isopropyl-N-methylaminocarbonyl, N-n-butyl-N-methylaminocarbonyl and N-tert-butyl-N-methylaminocarbonyl.

$(C_3-C_7)$-Cycloalkyl and $(C_3-C_6)$-cycloalkyl stand for the purposes of the invention for a monocyclic saturated cycloalkyl group having respectively 3 to 7 and 3 to 6 ring carbon atoms. Examples which may be preferably mentioned are: cyclopropyl, cyclobutyl, cyclopentyl, cyclohexyl and cycloheptyl.

A 4- to 7-membered heterocycle stands for the purposes of the invention for a monocyclic saturated heterocycle having a total of 4 to 7 ring atoms which contains one or two ring heteroatoms from the group consisting of N, O, S, SO and $SO_2$ and which is attached via a ring carbon atom or, if appropriate, via a ring nitrogen atom. Preference is given to a 4- to 6-membered heterocycle having one or two ring heteroatoms from the group consisting of N, O and S; particular preference is given to a 5- or 6-membered heterocycle having one or two ring heteroatoms from the group consisting of N and O. Examples which may be mentioned are: azetidinyl, oxetanyl, pyrrolidinyl, pyrazolidinyl, tetrahydrofuranyl, thiolanyl, piperidinyl, piperazinyl, tetrahydropyranyl, tetrahydrothiopyranyl, morpholinyl, thiomorpholinyl, hexahydroazepinyl and hexahydro-1,4-diazepinyl. Preference is given to azetidinyl, pyrrolidinyl, tetrahydrofuranyl, piperidinyl, piperazinyl, tetrahydropyranyl and morpholinyl; particular preference is given to pyrrolidinyl, tetrahydrofuranyl, piperidinyl and morpholinyl.

A pyrrolidino, piperidino- or morpholino radical stands for the purposes of the invention for a pyrrolidino, piperidino- or morpholino ring which is attached via the respective ring nitrogen atom.

5- or 6-membered heteroaryl stands for the purposes of the invention for an aromatic heterocycle (heteroaromatic) having a total of 5 or 6 ring atoms which contains one or two ring heteroatoms from the group consisting of N, O and S and which is attached via a ring carbon atom or, if appropriate, via a ring nitrogen atom. Examples which may be mentioned are: furyl, pyrrolyl, thienyl, pyrazolyl, imidazolyl, oxazolyl, thiazolyl, isoxazolyl, isothiazolyl, pyridyl, pyrimidinyl, pyridazinyl and pyrazinyl. Preference is given to thienyl, pyridyl, pyrimidinyl, pyridazinyl and pyrazinyl.

Halo=embraces for the purposes of the invention fluorine, chlorine, bromine and iodine. Preference is given to chlorine, fluorine or bromine; particular preference is given to fluorine or chlorine.

For the purposes of the invention, an oxo substituent is an oxygen atom which is attached via a double bond to a carbon atom.

When radicals in the compounds according to the invention are substituted, the radicals may be mono- or polysubstituted, unless specified otherwise. For the purposes of the present invention, the meanings of all radicals which occur more than once are independent of one another. Preference is given to substitution by one or two identical or different substituents. Very particularly preferred is substitution by one substituent.

The present invention provides in particular those compounds of the formula (I) in which
A represents CH,
and their salts, solvates and solvates of the salts.

The present invention furthermore provides in particular those compounds of the formula (I) in which
$R^4$ represents trifluoromethyl
and
$R^5$ represents hydrogen or fluorine,
and their salts, solvates and solvates of the salts.

Preferred for the purposes of the present invention are compounds of the formula (I) in which
A represents CH,
$R^1$ represents hydrogen, fluorine, chlorine, cyano, nitro, $(C_1-C_4)$-alkyl, difluoromethyl, trifluoromethyl, $(C_1-C_4)$-alkoxy, difluoromethoxy, trifluoromethoxy, amino, mono- or di-$(C_1-C_4)$-alkylamino
or
represents a group of the formula —NH—C(=O)—$R^6$, —NH—$SO_2$—$R^7$ or —$SO_2$—$R^8$ in which
$R^6$ and $R^7$ each represent $(C_1-C_4)$-alkyl
and
$R^8$ represents $(C_1-C_4)$-alkyl which may be substituted by hydroxyl, $(C_1-C_4)$-alkoxy, hydroxycarbonyl, aminocarbonyl, $(C_3-C_6)$-cycloalkyl or phenyl, or represents $(C_3-C_6)$-cycloalkyl or phenyl,
where the mentioned phenyl groups may be substituted up to two times by identical or different substituents from the group consisting of fluorine, chlorine, cyano, methyl, trifluoromethyl, methoxy and trifluoromethoxy,
$R^2$ represents hydrogen, $(C_1-C_4)$-alkyl or $(C_2-C_4)$-alkenyl
or
represents a group of the formula -$L^1$-C(=O)—O—$R^{10}$, -$L^2$-C(=O)—$NR^{11}R^{12}$ or -$L^2$-$SO_2$—$R^{14}$ in which
$L^1$ represents methylene or ethane-1,2-diyl,
$L^2$ represents a bond, methylene, ethane-1,1-diyl or ethane-1,2-diyl,
$R^{10}$ represents hydrogen or $(C_1-C_4)$-alkyl,
$R^{11}$ represents hydrogen or $(C_1-C_4)$-alkyl which may be substituted by hydroxyl or $(C_1-C_4)$-alkoxy,
$R^{12}$ represents hydrogen, $(C_1-C_6)$-alkyl or $(C_3-C_6)$-cycloalkyl,
where $(C_1-C_6)$-alkyl may be substituted up to two times by identical or different substituents from the group consisting of hydroxyl, $(C_1-C_4)$-alkoxy, hydroxycarbonyl, $(C_1-C_4)$-alkoxycarbonyl and aminocarbonyl and where in $(C_1-C_6)$-alkyl a $CH_2$ group may be exchanged for an oxygen atom if this results in a chemically stable compound,
or
$R^{11}$ and $R^{12}$ together with the nitrogen atom to which they are attached form a 5- or 6-membered heterocycle which may contain a further ring heteroatom from the group consisting of N, O and S and which may be substituted by $(C_1-C_4)$-alkyl, hydroxyl, $(C_1-C_4)$-alkoxy or oxo,
where $(C_1-C_4)$-alkyl for its part may be substituted by hydroxy or $(C_1-C_4)$-alkoxy,
and
$R^{14}$ represents $(C_1-C_4)$-alkyl, $(C_3-C_6)$-cycloalkyl or phenyl,
where phenyl may be substituted up to two times by identical or different substituents from the group consisting of fluorine, chlorine, cyano, methyl, trifluoromethyl, methoxy and trifluoromethoxy,
$R^3$ represents $(C_1-C_4)$-alkyl which may be substituted by hydroxyl, $(C_1-C_4)$-alkoxy, hydroxycarbonyl, $(C_1-C_4)$-alkoxycarbonyl, aminocarbonyl, mono- or di-$(C_1-C_4)$-alkyl-aminocarbonyl or 5- or 6-membered heteroaryl, represents $(C_2-C_4)$-alkenyl or
represents a group of the formula -$L^3$-$R^{15}$ in which
$L^3$ represents a bond or ($C_1$-$C_4$)-alkanediyl
and
$R^{15}$ represents ($C_3$-$C_7$)-cycloalkyl, 4- to 6-membered heterocyclyl or phenyl,
where 4- to 6-membered heterocyclyl for its part may be substituted by oxo
and
phenyl for its part may be substituted up to two times by identical or different substituents from the group consisting of fluorine, chlorine, cyano, methyl, trifluoromethyl, methoxy and trifluoromethoxy,
$R^4$ represents trifluoromethyl
and
$R^5$ represents hydrogen or fluorine,
and their salts, solvates and solvates of the salts.

Particularly preferred for the purposes of the present invention are compounds of the formula (I) in which
A represents CH,
$R^1$ represents hydrogen, fluorine, chlorine, nitro, methyl, difluoromethyl, trifluoromethyl, methoxy, trifluoromethoxy or a group of the formula —$SO_2$—$R^8$ in which
$R^8$ represents ($C_1$-$C_4$)-alkyl which may be substituted by hydroxyl, methoxy or ethoxy,
$R^2$ represents hydrogen, ($C_1$-$C_4$)-alkyl or a group of the formula —$CH_2$—C(=O)—O—$R^{10}$ or —$CH_2$—C(=O)—$NR^{11}R^{12}$ in which
$R^{10}$ represents ($C_1$-$C_4$)-alkyl,
$R^{11}$ represents hydrogen or methyl,
$R^{12}$ represents hydrogen or ($C_1$-$C_4$)-alkyl which may be substituted by hydroxyl, methoxy or ethoxy
or
$R^{11}$ and $R^{12}$ together with the nitrogen atom to which they are attached form a pyrrolidino, piperidino or morpholino ring,
$R^3$ represents ($C_1$-$C_4$)-alkyl which may be substituted by hydroxyl, pyrrolidino, piperidino, morpholino or pyridyl, represents allyl or represents a group of the formula -$L^3$-$R^{15}$ in which
$L^3$ represents a bond, methylene or ethane-1,2-diyl
and
$R^{15}$ represents ($C_3$-$C_7$)-cycloalkyl or phenyl,
where phenyl for its part may be substituted up to two times by identical or different substituents from the group consisting of fluorine, chlorine, cyano, methyl and trifluoromethyl,
$R^4$ represents trifluoromethyl
and
$R^5$ represents hydrogen,
and their salts, solvates and solvates of the salts.

Very particularly preferred for the purposes of the present invention are compounds of the formula (I) in which
A represents CH,
$R^1$ represents hydrogen, trifluoromethyl or methylsulphonyl,
$R^2$ represents hydrogen or a group of the formula —$CH_2$—C(=O)—$NR^{11}R^{12}$ in which
$R^{11}$ and $R^{12}$ independently of one another represent hydrogen or methyl
or
$R^{11}$ and $R^{12}$ together with the nitrogen atom to which they are attached form a pyrrolidino ring,
$R^3$ represents methyl, ethyl, 2-hydroxyethyl or 2-(morpholin-4-yl)ethyl, $R^4$ represents trifluoromethyl
and
$R^5$ represents hydrogen,
and their salts, solvates and solvates of the salts.

Of particular relevance are compounds according to formula (I) having the configuration shown in formula (I-ent) at the 4-position of the dihydropyrimidinone ring

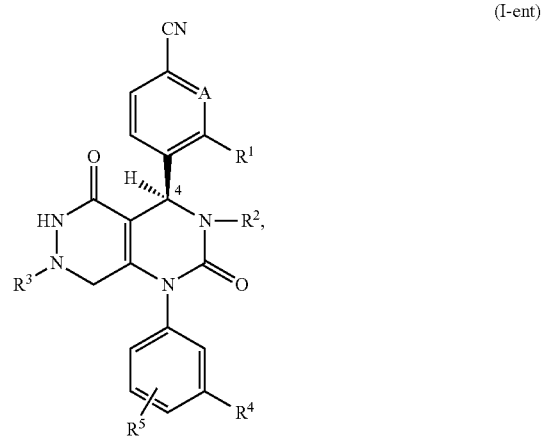

(I-ent)

in which A, $R^1$, $R^2$, $R^3$, $R^4$ and $R^5$ each have the meanings given above, and their salts, solvates and solvates of the salts.

Specific radical definitions given in the respective combinations or preferred combinations of radicals are, independently of the combinations of radicals given in each case, also replaced by any radical definitions of other combinations.

Very particular preference is given to combinations of two or more of the preferred ranges mentioned above.

The 1,4-diarylpyrimido[4,5-d]pyridazine-2,5-diones of the formula (I) according to the invention can be present in various tautomeric forms (cf. Scheme 1 below); the present invention expressly incorporates all tautomeric forms.

Scheme 1

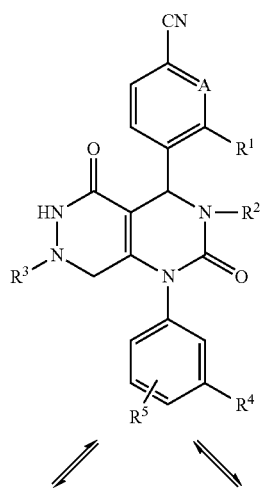

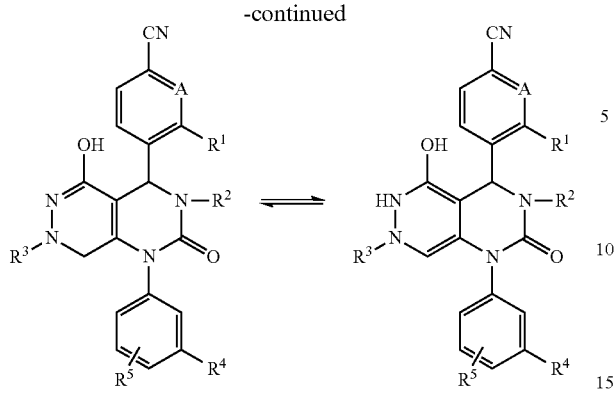

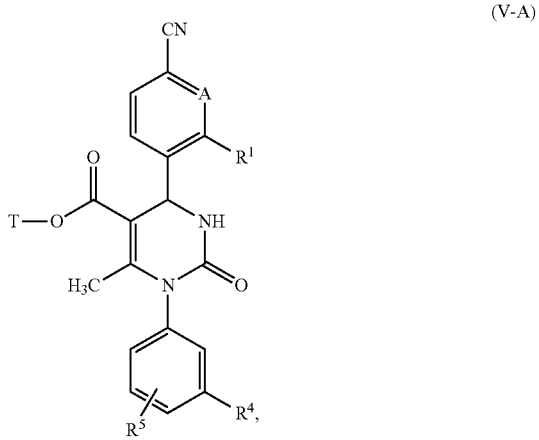

The invention furthermore provides a process for preparing the compounds of the formula (I) according to the invention, characterized in that initially a compound of the formula (II)

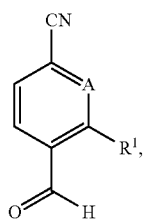
(II)

in which A and $R^1$ have the meanings given above, is condensed in the presence of an acid or an acid anhydride in a 3-component one-pot reaction or sequentially with an acetoacetic ester of the formula (III)

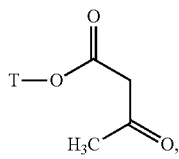
(III)

in which

T represents methyl or ethyl, and a phenylurea derivative of the formula (IV)

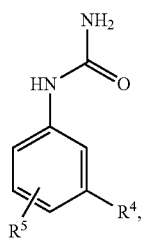
(IV)

in which $R^4$ and $R^5$ have the meanings given above, to give a compound of the formula (V-A)

(V-A)

in which A, T, $R^1$, $R^4$ and $R^5$ each have the meanings given above, and this compound is then

[A] in the case that $R^2$ in formula (I) represents hydrogen, brominated in an inert solvent to give a compound of the formula (VI-A)

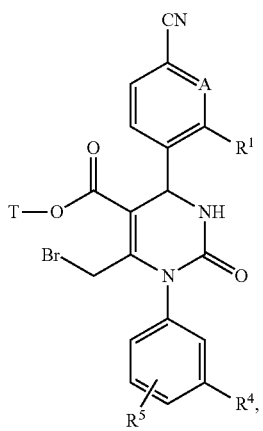
(VI-A)

in which A, T, $R^1$, $R^4$ and $R^5$ each have the meanings given above, and subsequently reacted with a hydrazine derivative of the formula (VII)

$R^3$—NH—NH$_2$ (VII), in which $R^3$ has the meaning given above, with formation of a six-membered ring to give a compound of the formula (I-A)

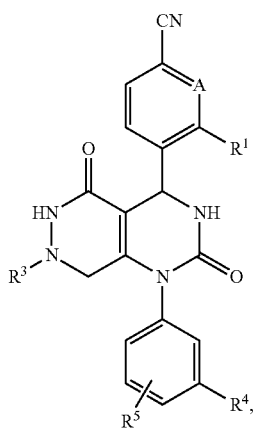
(I-A)

in which A, R$^1$, R$^3$, R$^4$ and R$^5$ each have the meanings given above, or

[B] in the case that R$^2$ in formula (I) is different from hydrogen, initially reacted with a compound of the formula (VIII)

R$^{2A}$—X                (VIII), in which

R$^{2A}$ has the meaning of R$^2$ given above, but does not represents hydrogen, and X represents a leaving group such as, for example, halogen, mesylate, tosylate or triflate, in the presence a base to give a compound of the formula (V-B)

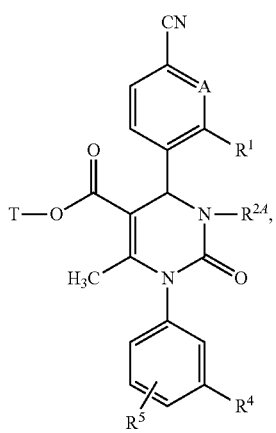
(V-B)

in which A, T, R$^1$, R$^{2A}$, R$^4$ and R$^5$ each have the meanings given above, then brominated in an inert solvent to give a compound of the formula (VI-B)

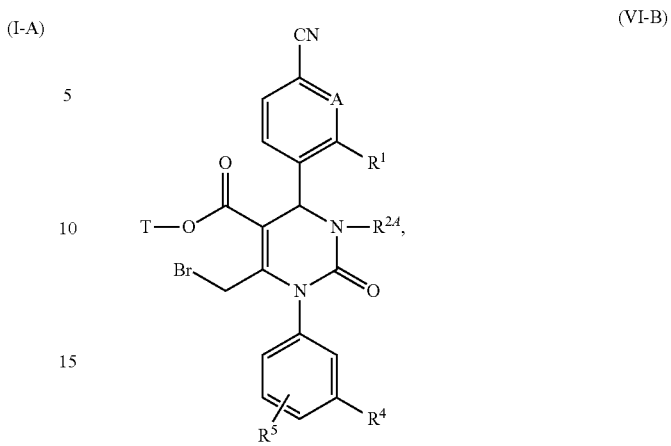
(VI-B)

in which A, T, R$^1$, R$^{2A}$, R$^4$ and R$^5$ each have the meanings given above, and subsequently reacted with a hydrazine derivative of the formula (VII)

R$^3$—NH—NH$_2$           (VII), in which R$^3$ has the meaning given above, with cyclization to give a compound of the formula (I-B)

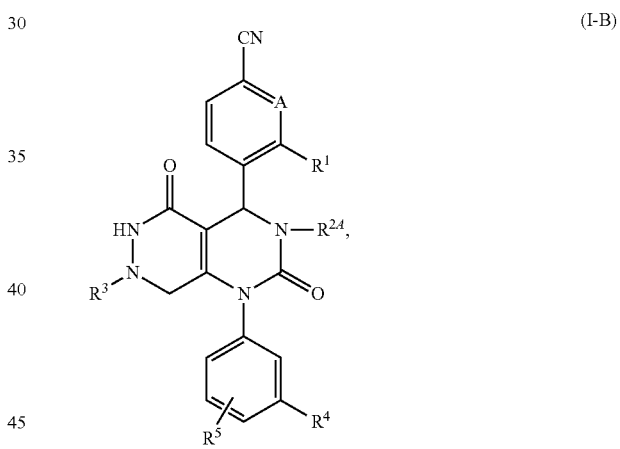
(I-B)

in which A, R$^1$, R$^{2A}$, R$^3$, R$^4$ and R$^5$ each have the meanings given above, and the compound of the formula (I-A) or (I-B) obtained in this manner is, if appropriate, separated by methods known to the person skilled in the art into its enantiomers and/or diastereomers and/or converted with the appropriate (i) solvents and/or (ii) bases or acids into its solvates, salts and/or solvates of the salts.

Suitable solvents for the process step (II)+(III)+(IV)→(V-A) are customary organic solvents which do not change under the reaction conditions. These include, for example, ethers, such as diethyl ether, diisopropyl ether, methyl tert-butyl ether, 1,2-dimethoxyethane, dioxane or tetrahydrofuran, alcohols, such as methanol, ethanol, n-propanol, isopropanol, n-butanol or tert-butanol, hydrocarbons, such as pentane, hexane, cyclohexane, benzene, toluene or xylene, halogenated hydrocarbons, such as dichloromethane, 1,2-dichloroethan, trichloromethane or chlorobenzene, or other solvents, such as ethyl acetate, acetonitrile, dimethyl sulphoxide or N,N-di-methylformamide. It is also possible to use mixtures of the solvents mentioned. Preference is given to using methyl tert-butyl ether, tetrahydrofuran or dioxane.

Suitable acids for the process step (II)+(III)+(IV)→(V-A) are customary inorganic or organic acids or acid anhydrides. These preferably include carboxylic acids, such as, for example, acetic acid or trifluoroacetic acid, sulphonic acids, such as methanesulphonic acid, trifluoromethane-sulphonic acid or p-toluenesulphonic acid, hydrochloric acid, sulphuric acid, phosphoric acid, phosphonic acids, or phosphoric or phosphonic anhydrides or esters, such as polyphosphoric acid, phosphoric acid triethyl ester, polyphosphoric acid ethyl ester, phosphorus pentoxide or propanephosphonic anhydride. Preference is given to using phosphoric acid triethyl ester in combination with phosphorus pentoxide. The acid is generally employed in an amount of from 0.25 mol to 100 mol based on 1 mol of the compound (III).

The process step (II)+(III)+(IV)→(V-A) is generally carried out in a temperature range of from +20° C. to +150° C., preferably at from +50° C. to +100° C. The reaction can be carried out at atmospheric, elevated or reduced pressure (for example from 0.5 to 5 bar). In general, the process is carried out at atmospheric pressure.

The bromination in process step (V-A)→(VI-A) and (V-B)→(VI-B) is preferably carried out using elemental bromine in a customary inert solvent such as chloroform at a temperature of from −20° C. to +40° C.

The dihydropyridazinone formation in process step (VI-A)+(VII)→(I-A) bzw. (VI-B)+(VII)→(I-B) is preferably carried out in an ether, such as tetrahydrofuran, 1,2-dimethoxyethane or dioxane as inert solvent at a temperature of from +20° C. to +120° C. Here, the hydrazine derivative of the formula (VII) can also be employed in the form of a salt, for example as hydrochloride; in this case the reaction is carried out in the presence of a tertiary amine base, such as, for example, triethyl-amine, N-methylmorpholine, N-methylpiperidine or N,N-diisopropylethylamine, or a carbonate base, such as, for example, sodium carbonate, potassium carbonate or caesium carbonate or polymer-supported carbonate.

Suitable solvents for the process step (V-A)+(VIII)→(V-B) are customary organic solvents which do not change under the reaction conditions. These include, for example, ethers, such as diethyl ether, diisopropyl ether, methyl tert-butyl ether, 1,2-dimethoxyethane, dioxane or tetrahydrofuran, hydrocarbons, such as pentane, hexane, cyclohexane, benzene, toluene or xylene, halogenated hydrocarbons, such as dichloromethane, 1,2-dichloroethan, trichloromethane or chlorobenzene, or other solvents, such as ethyl acetate, acetone, methyl ethyl ketone, methyl tert-butyl ketone, acetonitrile, dimethyl sulphoxide, N,N-dimethylformamide, N,N'-dimethyl-propyleneurea (DMPU) or N-methylpyrrolidone (NMP). It is also possible to use mixtures of the solvents mentioned. Preference is given to using tetrahydrofuran, acetonitrile or dimethylformamide.

Suitable bases for the process step (V-A)+(VIII)→(V-B) are customary inorganic or organic bases. These include in particular alkali metal or alkaline earth metal carbonates, such as lithium carbonate, sodium carbonate, potassium carbonate, calcium carbonate or caesium carbonate, alkali metal alkoxides, such as sodium tert-butoxide or potassium tert-butoxide, alkali metal hydrides, such as sodium hydride or potassium hydride, amides, such as lithium bis(trimethylsilyl)amide or potassium bis(trimethylsilyl)amide or lithium diisopropylamide (LDA), organic amines, such as triethylamine, N-methylmorpholine, N-methylpiperidine, N,N-diisopropylethylamine, 1,5-diazabicyclo [4.3.0]non-5-ene (DBN), 1,8-diazabicyclo[5.4.0]undec-7-ene (DBU), pyridine or 4-N,N-dimethylaminopyridine, or phosphazene bases ("Schwesinger bases"), such as, for example, P1-t-Bu, P2-t-Bu or P4-t-Bu. Preference is given to using potassium carbonate, caesium carbonate, sodium hydride, triethylamine or N,N-diisopropylethylamine; particular preference is given to potassium carbonate and sodium hydride. The base is generally employed in an amount of from 0.1 mol to 10 mol, preferably from 1 mol to 3 mol, based on 1 mol of the compound (V-A).

The process step (V-A)+(VIII)→(V-B) is generally carried out in a temperature range of from −20° C. to +100° C., preferably at from 0° C. to +80° C. The reaction can be carried out at atmospheric, elevated or reduced pressure (for example from 0.5 to 5 bar). In general, the process is carried out at atmospheric pressure.

If expedient, further compounds of the formula (I) according to the invention can also be prepared by transformations of functional groups of individual substituents, in particular those listed under $R^1$, $R^2$ and $R^3$, starting with other compounds of the formula (I) obtained by the above process. These transformations are carried out according to customary methods known to the person skilled in the art and include, for example, reactions such as nucleophilic or electrophilic substitution reactions, transition metal-mediated coupling reactions (for example Suzuki or Heck reaction), oxidation, reduction, hydrogenation, alkylation, acylation, amination, hydroxylation, etherification, esterification, ester cleavage and ester hydrolysis, formation of nitriles, carboxamides, sulphonamides, carbamates and ureas, and also the introduction and removal of temporary protective groups [cf. also the Reaction Schemes 2-4 below and the exemplary embodiments].

Separation of the compounds according to the invention into the corresponding enantiomers and/or diastereomers is possible, as expedient, at the stage of the compounds (I-A) or (I-B) or else at the stage of the compounds (V-A) or (V-B), where the latter can then, in separated form, be reacted further according to the process steps described above. Such a separation of stereoisomers can be carried out by customary methods known to the person skilled in the art; preference is given to chromatographic methods, in particular to HPLC chromatography on a chiral phase.

The compounds of the formulae (III), (IV), (VII) and (VIII) are commercially available, known per se from the literature or can be prepared by customary methods described in the literature.

Some of the compounds of the formula (II) are known from the literature, or they can be prepared analogously to processes described in the literature [cf. also Reaction Schemes 5 and 6 below and the literature cited therein].

In the process described above, it may, if appropriate, be synthetically expedient to employ, instead of the compound of the formula (II), initially a compound of the formula (II-A)

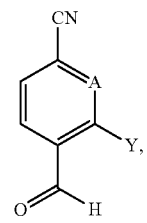

(II-A)

in which A has the meaning given above
and

Y represents an exchangeable group, such as, for example, fluorine, chlorine, bromine, iodine, nitro or amino, in the reaction sequence described and then to introduce the desired aryl substituent R¹ at the stage of the dihydropyrimidinone—which corresponds to the compound (V-A) or (V-B)—in exchange for the radical Y. Some of the compounds of the formula (II-A) are likewise known from the literature, or they can be prepared analogously to methods known from the literature.

The processes described above can be illustrated in an examplary manner by the reaction schemes below:

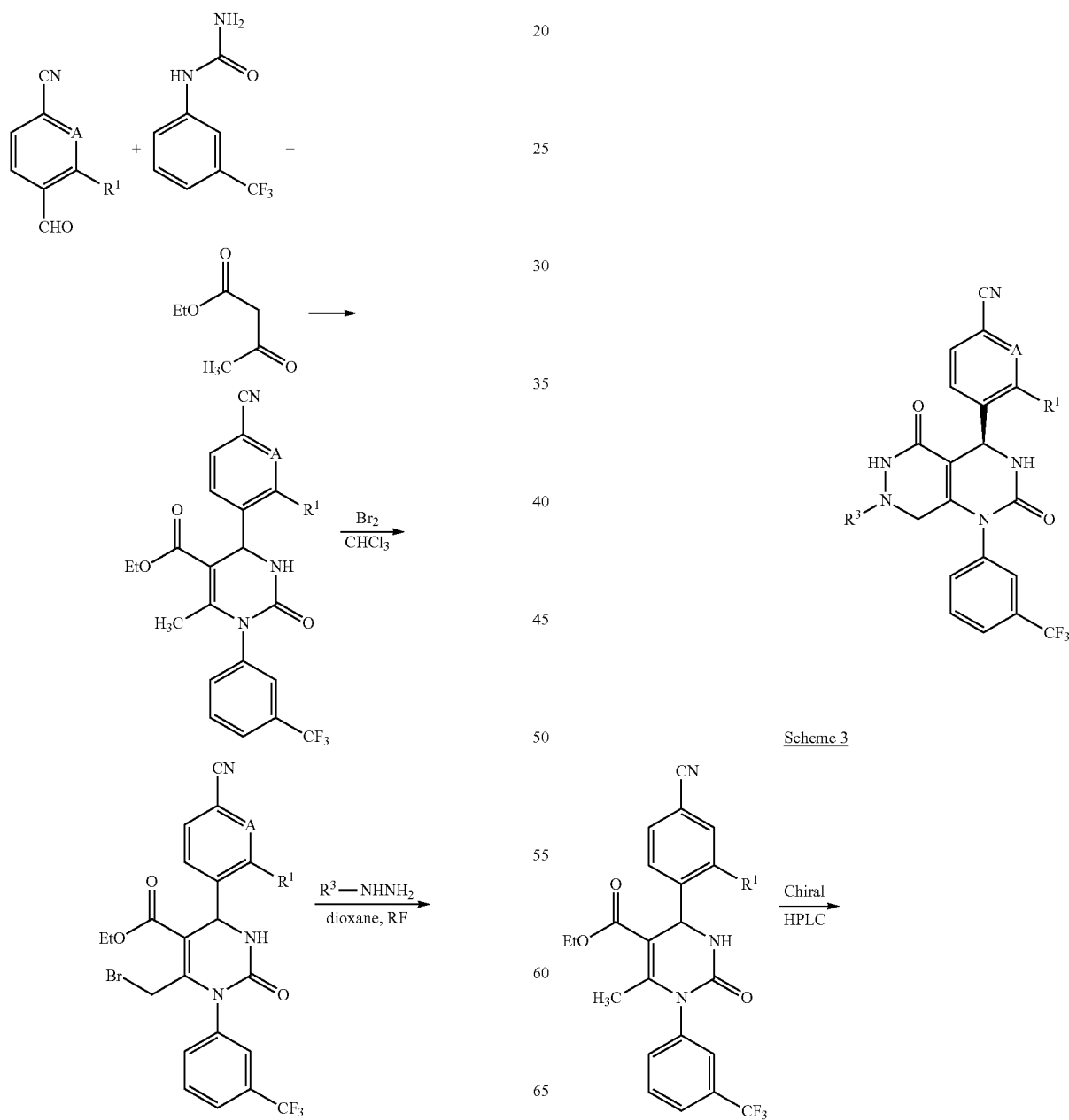

Scheme 4
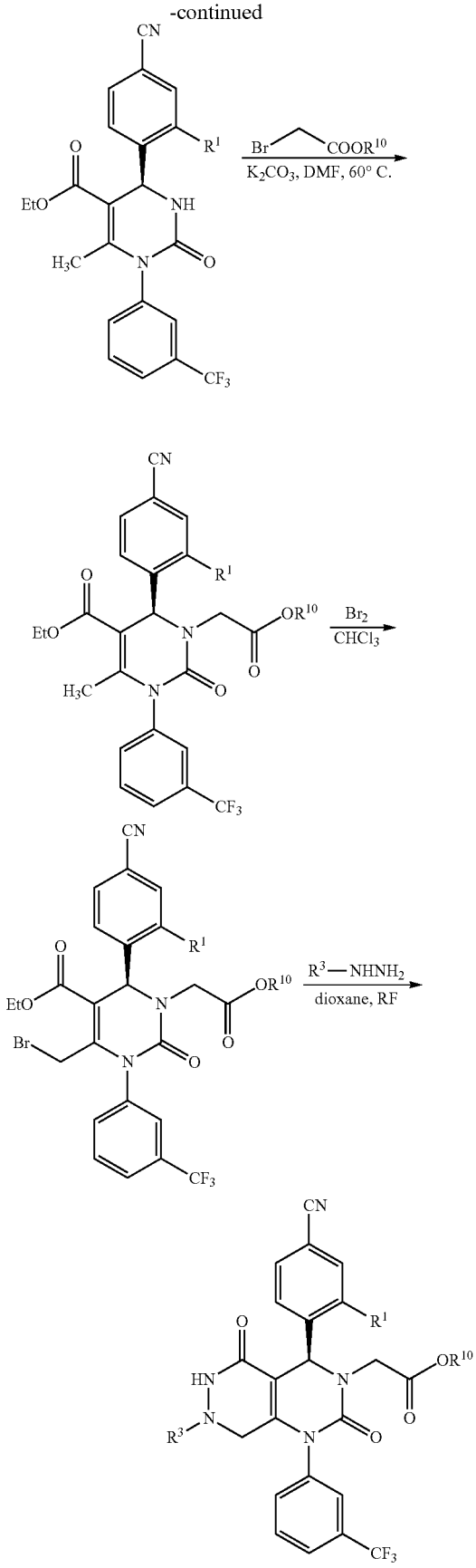
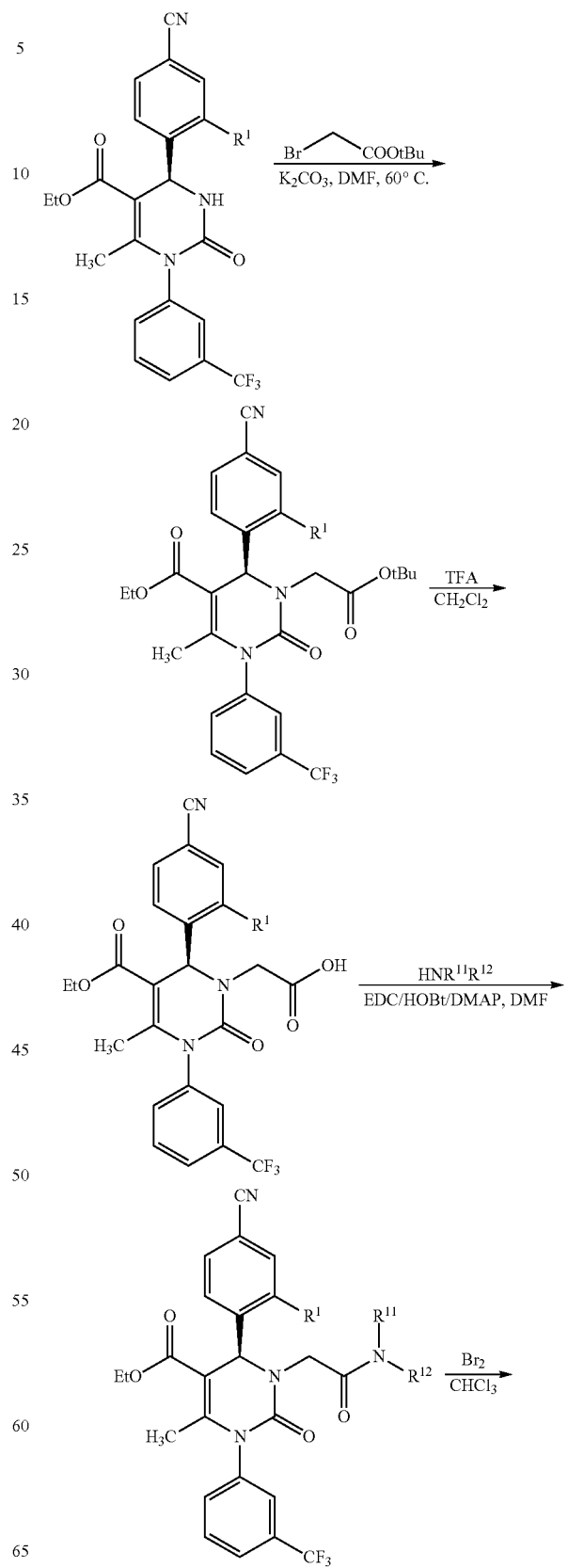

-continued
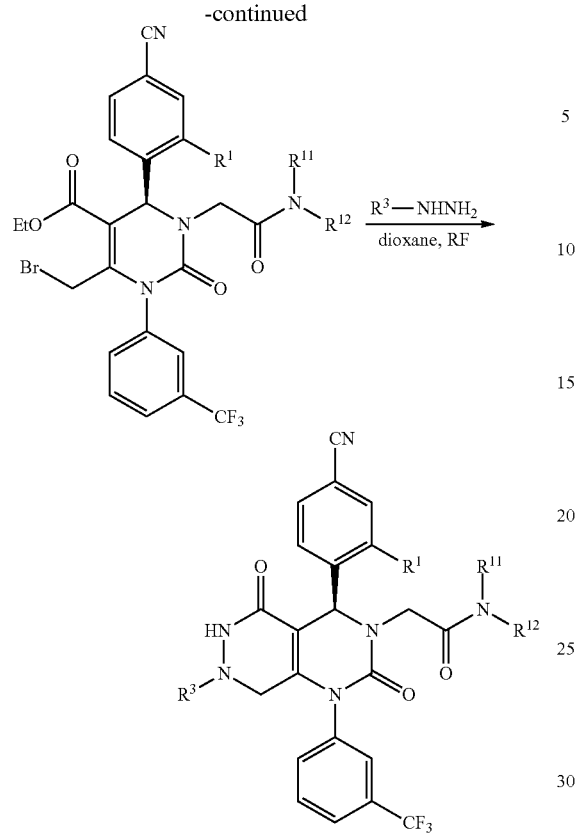
Scheme 5
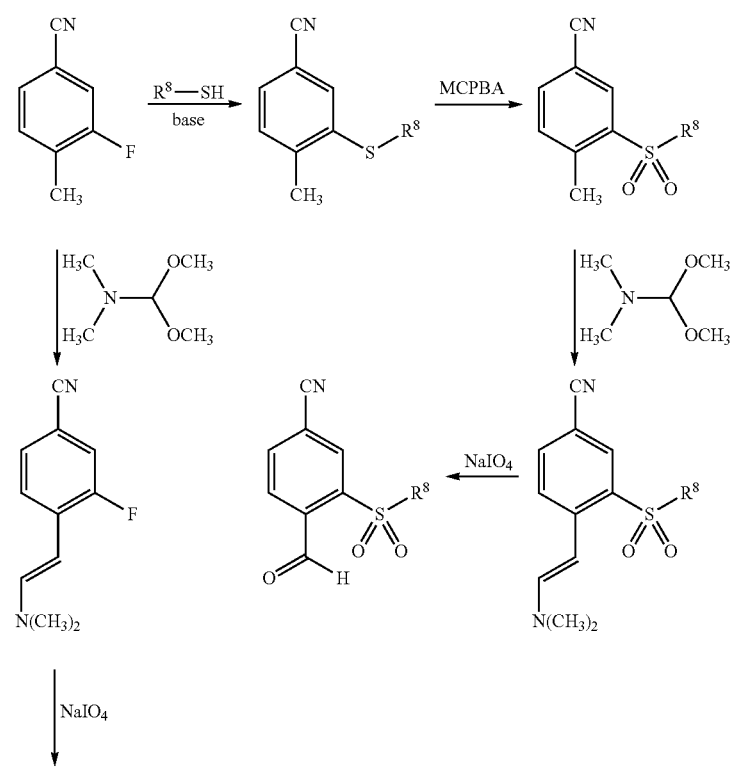

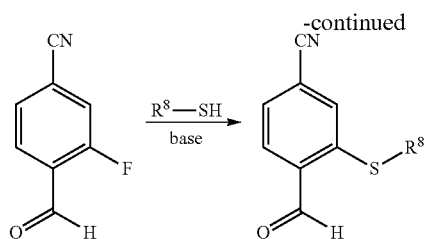

-continued

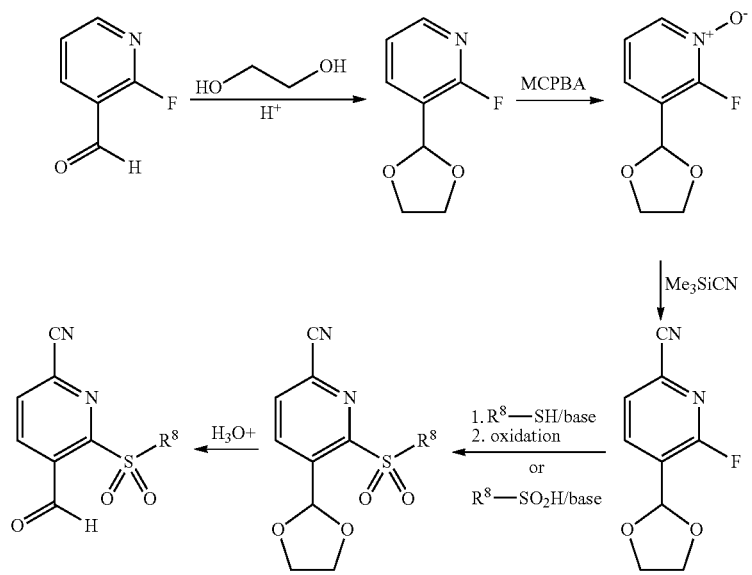

Scheme 6

[cf., for example, W. K. Fife, *J. Org. Chem.* 48, 1375 (1983); H. Vorbrüggen and K. Krolikiewicz, *Synthesis*, 316 (1983); R. T. Shuman et al., *J. Org. Chem.* 55, 738 (1990); C. S. Burgey et al., *J. Med. Chem.* 46 (4), 461 (2003); J. J. Li et al., *J. Med. Chem.* 39, 1846 (1996); K. N. Dack et al., *Bioorg. Med. Chem. Lett.* 8 (16), 2061 (1998)].

The compounds according to the invention have useful pharmacological properties and can be used for prevention and treatment of disorders in humans and animals.

The compounds according to the invention are potent low-molecular-weight, unreactive and selective inhibitors of human neutrophil elastase. Furthermore, the compounds according to the invention have advantageous pharmacokinetic properties, such as, for example good bioavailability and/or half-life or oral administration or only low plasma proteins binding.

Accordingly, the compounds according to the invention are particularly suitable for the treatment and/or prevention of disorders and pathological processes, in particular those where neutrophil elastase (HNE) is involved in an inflammatory event and/or a tissue or vessel remodeling.

For the purposes of the present invention, this includes in particular disorders such as pulmonary arterial hypertension (PAH) and other forms of pulmonary hypertension (PH), chronic obstructive pulmonary disease (COPD), acute respiratory distress syndrome (ARDS), acute lung injury (ALI), alpha-1-antitrypsin deficiency (AATD), pulmonary fibrosis, pulmonary emphysema (e.g. cigarette-smoke-induced pulmonary emphysema), cystic fibrosis (CF), acute coronary syndrome (ACS), inflammations of the heart muscle (myo-carditis) and other autoimmune heart conditions (pericarditis, endocarditis, valvolitis, aortitis, cardiomyopathies), myocardial infarction, cardiogenic shock, heart failure, aneurysms, sepsis (SIRS), multi-organ failure (MODS, MOF), arteriosclerosis, inflammatory disorders of the kidney, chronic inflammations of the intestine (IBD, CD, UC), pancreatitis, peritonitis, rheumatoid disorders, inflammatory skin disorders and also inflammatory eye disorders.

The compounds according to the invention can furthermore be used for the treatment and/or prevention of asthmatic disorders of various degrees of severity with intermittent or persistent course (refractive asthma, bronchial asthma, allergic asthma, intrinsic asthma, extrinsic asthma, asthma induced by medicaments or by dust), of various forms of bronchitis (chronic bronchitis, infectious bronchitis, eosinophilic bronchitis), of Bronchiolitis obliterans, bronchiectasia, pneumonia, farmer's lung and related diseases, coughs and colds (chronic inflammatory cough, iatrogenic cough), inflammations of the nasal mucosa (including medicament-related rhinitis, vasomotoric rhinitis and seasonal allergic rhinitis, for example hay fever) and of polyps.

In addition, the compounds according to the invention can also be used for the treatment and/or prevention of micro- and macrovascular injuries (vasculitis), reperfusion damage, arterial and venous thromboses, diabetic and non-diabetic nephropathy, glomerulonephritis, glomerulosclerosis, nephrotic syndrome, hypertensive nephrosclerosis, microalbuminuria, acute and chronic renal insufficiency, acute and chronic renal failure, cystitis, urethritis, prostatitis, epidymitis, oophoritis, salpingitis, vulvovaginitis, erectile dysfunction, Hunner's ulcer, Peyronie's disease, arterial hypertension, shock, atrial and ventricular arrhythmias, transitory and ischemic attacks, heart failure, stroke, endothelial dysfunction, peripheral and cardiovascular disorders, impaired peripheral perfusion, edema formation such as, for example, pulmonary edema, brain edema, renal edema and heart failure-related edema, restenoses, for example after thrombolysis therapies, percutaneous transluminal angioplasties (PTA), transluminal coronary angioplasties (PTCA), heart transplants and bypass operations, for increased levels of fibrinogen and low-density LDL and also for increased concentrations of plasminogen activator inhibitor 1 (PAI-1), of dyslipidemias (hypercholesterolemia, hypertriglyceridemia, increased concentrations of postprandial plasma triglycerides, hypoalphalipoproteinemia, combined hyperlipidemias) and also metabolic disorders (metabolic syndrome, hyperglycemia, insulin-dependent diabetes, non-insulin-dependent diabetes, gestational diabetes, hyperinsulinemia, insulin resistance, glucose intolerance, adipositas and diabetic sequelae, such as retinopathy, nephropathy and neuropathy), neoplastic disorders (skin cancer, brain tumours, breast cancer, bone marrow tumours, leukaemias, liposarcomas, carcinomas of the gastrointestinal tract, the liver, the pancreas, the lungs, the kidneys, the urethra, the prostate and the genital tract and also malignant tumours of the lymphoproliferative system, such as, for example, Hodgkin's and non-Hodgkin's lymphoma), of disorders of the gastrointestinal tract and the abdomen (glossitis, gingivitis, periodontitis, oesophagitis, eosinophilic gastroenteritis, mastocytosis, Crohn's disease, colitis, proctitis, anus pruritis, diarrhoea, coeliac disease, hepatitis, hepatic fibrosis, cirrhosis of the liver, pancreatitis and cholecystitis), of disorders of the central nervous system and neurodegenerative disorders (stroke, Alzheimer's disease, Parkinson's disease, dementia, epilepsy, depressions, multiple sclerosis), immune disorders, thyroid disorders (hyperthyreosis), skin disorders (psoriasis, acne, eczema, neurodermitis, various forms of dermatitis, such as, for example, dermatitis abacribus, actinic dermatitis, allergic dermatitis, ammonia dermatitis, facticial dermatitis, autogenic dermatitis, atopic dermatitis, dermatitis calorica, dermatitis combustionis, dermatitis congelationis, dermatitis cosmetica, dermatitis escharotica, exfoliative dermatitis, dermatitis gangraenose, stasis dermatitis, dermatitis herpetiformis, lichenoid dermatitis, dermatitis linearis, dermatitis maligna, medicinal eruption dermatitis, dermatitis palmaris and plantaris, parasitic dermatitis, photoallergic contact dermatitis, phototoxic dermatitis, dermatitis pustularis, seborrhoeic dermatitis, sunburn, toxic dermatitis, Meleney's ulcer, dermatitis veneata, infectious dermatitis, pyrogenic dermatitis and perioral dermatitis, and also keratitis, bullosis, vasculitis, cellulitis, panniculitis, lupus erythematosus, erythema, lymphomas, skin cancer, Sweet syndrome, Weber-Christian syndrome, scar formation, wart formation, chilblains), of inflammatory eye diseases (saccoidosis, blepharitis, conjunctivitis, iritis, uveitis, chorioiditis, ophthalmitis), viral diseases (caused by influenza, adeno and corona viruses, such as, for example, HPV, HCMV, HIV, SARS), of disorders of the skeletal bone and the joints and also the skeletal muscle (multifarious forms of arthritis, such as, for example, arthritis alcaptonurica, arthritis ankylosans, arthritis dysenterica, arthritis exsudativa, arthritis fungosa, arthritis gonorrhoica, arthritis mutilans, arthritis psoriatica, arthritis purulenta, arthritis rheumatica, arthritis serosa, arthritis syphilitica, arthritis tuberculosa, arthritis urica, arthritis villonodularis pigmentosa, atypical arthritis, haemophilic arthritis, juvenile chronic arthritis, rheumatoid arthritis and metastatic arthritis, furthermore Still syndrome, Felty syndrome, Sjörgen syndrome, Clutton syndrome, Poncet syndrome, Pott syndrome and Reiter syndrome, multifarious forms of arthropathias, such as, for example, arthropathie deformans, arthropathie neuropathica, arthropathie ovaripriva, arthropathie psoriatica and arthropathie tabica, systemic scleroses, multifarious forms of inflammatory myopathies, such as, for example, myopathie epidemica, myopathie fibrosa, myopathie myoglobinurica, myopathie ossificans, myopathie ossificans neurotica, myopathie ossificans progressiva multiplex, myopathie purulenta, myopathie rheumatica, myopathie trichinosa, myopathie tropica and myopathie typhosa, and also the Günther syndrome and the Münchmeyer syndrome), of inflammatory changes of the arteries (multifarious forms of arteritis, such as, for example, endarteritis, mesarteritis, periarteritis, panarteritis, arteritis rheumatica, arteritis deformans, arteritis temporalis, arteritis cranialis, arteritis gigantocellularis and arteritis granulomatosa, and also Horton syndrome, Churg-Strauss syndrome and Takayasu arteritis), of Muckle-Well syndrome, of Kikuchi disease, of polychondritis, dermatosclerosis and also other disorders having an inflammatory or immunological component, such as, for example, cataract, cachexia, osteoporosis, gout, incontinence, lepra, Sezary syndrome and paraneoplastic syndrome, for rejection reactions after organ transplants and for wound healing and angiogenesis in particular in the case of chronic wounds.

By virtue of their property profile, the compounds according to the invention are suitable in particular for the treatment and/or prevention of pulmonary arterial hypertension (PAH) and other forms of pulmonary hypertension (PH), chronic obstructive lung disease (COPD), acute lung injury (ALI), acute respiratory distress syndrome (ARDS), bronchiectasia, bronchiolitis obliterans, pulmonary emphysema, alpha-1-antitrypsin deficiency (AATD), cystic fibrosis (CF), sepsis and systemic-inflammatory response syndrome (SIRS), multiple organ failure (MOF, MODS), inflammatory intestinal disorders (IBD, Crohn's disease, colitis), chronic bronchitis, asthma, rhinitis, rheumatoid arthritis, inflammatory skin and eye diseases, arterioscleroses and cancerous disorders.

The present invention furthermore provides the use of the compounds according to the invention for the treatment and/or prevention of disorders, in particular the disorders mentioned above.

The present invention furthermore provides the use of the compounds according to the invention for preparing a medicament for the treatment and/or prevention of disorders, in particular the disorders mentioned above.

The present invention furthermore provides the use of the compounds according to the invention in a method for the treatment and/or prevention of disorders, in particular the disorders mentioned above.

The present invention furthermore provides a method for the treatment and/or prevention of disorders, in particular the disorders mentioned above, using an effective amount of at least one of the compounds according to the invention.

The compounds according to the invention can be employed alone or, if required, in combination with other active compounds. Accordingly, the present invention furthermore provides medicaments comprising at least one of the compounds according to the invention and one or more further active compounds, in particular for the treatment and/or prevention of the disorders mentioned above. Suitable active compounds for combinations are, by way of example and preferably:

compounds which inhibit the signal transduction cascade, for example and preferably from the group of the kinase inhibitors, in particular from the group of the tyrosine kinase and/or serine/threonine kinase inhibitors;

compounds which inhibit the degradation and remodelling of the extracellular matrix, for example and preferably inhibitors of matrix metalloproteases (MMPs), in particular inhibitors of stromelysin, collagenases, gelatinases and aggrecanases (here in particular of MMP-1, MMP-3, MMP-8, MMP-9, MMP-10, MMP-11 and MMP-13) and of metalloelastase (MMP-12);

compounds which block the binding of serotonin to its receptor, for example and preferably antagonists of the 5-HT$_{2b}$ receptor;

organic nitrates and NO donors, such as, for example, sodium nitroprusside, nitroglycerin, isosorbide mononitrate, isosorbide dinitrate, molsidomine or SIN-1, and also inhaled NO;

NO-independent but hem-dependent stimulators of soluble guanylate cyclase, such as, in particular, the compounds described in WO 00/06568, WO 00/06569, WO 02/42301 and WO 03/095451;

NO- and hem-independent activators of soluble guanylate cyclase, such as, in particular, the compounds described in WO 01/19355, WO 01/19776, WO 01/19778, WO 01/19780, WO 02/070462 and WO 02/070510;

prostacyclin analogs, such as, by way of example and preferably, iloprost, beraprost, treprostinil or epoprostenol;

compounds which inhibit soluble epoxide hydrolase (sEH), such as, for example, N,N'-dicyclo-hexylurea, 12-(3-adamantan-1-ylureido)dodecanoic acid or 1-adamantan-1-yl-3-{5-[2-(2-ethoxyethoxy)ethoxy]pentyl}urea;

compounds which influence the energy metabolism of the heart, such as, by way of example and preferably, etomoxir, dichloroacetate, ranolazine or trimetazidine;

compounds which inhibit the degradation of cyclic guanosine monophosphate (cGMP) and/or cyclic adenosine monophosphate (cAMP), such as, for example, inhibitors of phosphodiesterases (PDE) 1, 2, 3, 4 and/or 5, in particular PDE 5 inhibitors, such as sildenafil, vardenafil and tadalafil;

agents having antithrombotic action, by way of example and preferably from the group of the platelet aggregation inhibitors, of anticoagulants or of profibrinolytic substances;

active compounds which lower blood pressure, by way of example and preferably from the group of the calcium antagonists, angiotensin AII antagonists, ACE inhibitors, vasopeptidase inhibitors, endothelin antagonists, renin inhibitors, alpha-receptor blockers, beta-receptor blockers, mineralocorticoid receptor antagonists, Rho kinase inhibitors and diuretics;

agents having a bronchodilatory effect, by way of example and preferably from the group of the beta-adrenergic receptor agonists, such as, in particular, albuterol, isoproterenol, metaproterenol, terbutalin, formoterol or salmeterol, or from the group of the anticholinergics, such as, in particular, ipratropium bromide;

agents having antiinflammatory action, by way of example and preferably from the group of the glucocorticoids, such as, in particular, prednisone, prednisolone, methylprednisolone, triamcinolone, dexamethasone, beclomethasone, betamethasone, flunisolide, budesonide or fluticasone; and/or active ingredients which alter lipid metabolism, for example and preferably from the group of the thyroid receptor agonists, cholesterol synthesis inhibitors, such as, by way of example and preferably, HMG-CoA reductase inhibitors or squalene synthesis inhibitors, of ACAT inhibitors, CETP inhibitors, MTP inhibitors, PPAR-alpha, PPAR-gamma and/or PPAR-delta agonists, cholesterol absorption inhibitors, lipase inhibitors, polymeric bile adsorbents, bile acid reabsorption inhibitors and lipoprotein(a) antagonists.

In a preferred embodiment of the invention, the compounds according to the invention are employed in combination with a kinase inhibitor such as by way of example and preferably borte-zomib, canertinib, erlotinib, gefitinib, imatinib, lapatinib, lestaurtinib, lonafarnib, pegaptinib, peli-tinib, semaxanib, sorafenib, sunitinib, tandutinib, tipifarnib, vatalanib, fasudil, lonidamine, lefluno-mide, BMS-3354825 or Y-27632.

In a preferred embodiment of the invention, the compounds according to the invention are employed in combination with a serotonin receptor antagonist such as, by way of example and preferably, PRX-08066.

Agents having an antithrombotic effect preferably mean compounds from the group of platelet aggregation inhibitors, of anticoagulants or of profibrinolytic substances.

In a preferred embodiment of the invention, the compounds according to the invention are administered in combination with a platelet aggregation inhibitor such as by way of example and preferably aspirin, clopidogrel, ticlopidine or dipyridamole.

In a preferred embodiment of the invention, the compounds according to the invention are administered in combination with a thrombin inhibitor such as by way of example and preferably ximelagatran, melagatran, bivalirudin or clexane.

In a preferred embodiment of the invention, the compounds according to the invention are administered in combination with a GPIIb/IIIa antagonist such as by way of example and preferably tirofiban or abciximab.

In a preferred embodiment of the invention, the compounds according to the invention are administered in combination with a factor Xa inhibitor such as by way of example and preferably rivaroxaban, DU-176b, fidexaban, razaxaban, fondaparinux, idraparinux, PMD-3112, YM-150, KFA-1982, EMD-503982, MCM-17, MLN-1021, DX 9065a, DPC 906, JTV 803, SSR-126512 or SSR-128428.

In a preferred embodiment of the invention, the compounds according to the invention are administered in combination with heparin or a low molecular weight (LMW) heparin derivative.

In a preferred embodiment of the invention, the compounds according to the invention are administered in combination with a vitamin K antagonist such as by way of example and preferably coumarin.

Agents which lower blood pressure preferably mean compounds from the group of calcium antagonists, angiotensin AII antagonists, ACE inhibitors, endothelin antagonists, renin inhibitors, alpha-receptor blockers, beta-receptor blockers, mineralocorticoid receptor antagonists, Rho kinase inhibitors, and diuretics.

In a preferred embodiment of the invention, the compounds according to the invention are administered in combination with a calcium antagonist such as by way of example and preferably nifedipine, amlodipine, verapamil or diltiazem.

In a preferred embodiment of the invention, the compounds according to the invention are administered in combination with an alpha-1 receptor blocker such as by way of example and preferably prazosin.

In a preferred embodiment of the invention, the compounds according to the invention are administered in combination with a beta-receptor blocker such as by way of example and preferably propranolol, atenolol, timolol, pindolol, alprenolol, oxprenolol, penbutolol, bupranolol, metipranolol, nadolol, mepindolol, carazalol, sotalol, metoprolol, betaxolol, celiprolol, bisoprolol, carteolol, esmolol, labetalol, carvedilol, adaprolol, landiolol, nebivolol, epanolol or bucindolol.

In a preferred embodiment of the invention, the compounds according to the invention are administered in combination with an angiotensin AII antagonist such as by way of example and preferably losartan, candesartan, valsartan, telmisartan or embusartan.

In a preferred embodiment of the invention, the compounds according to the invention are administered in combination with an ACE inhibitor such as by way of example and preferably enalapril, captopril, lisinopril, ramipril, delapril, fosinopril, quinopril, perindopril or trandopril.

In a preferred embodiment of the invention, the compounds according to the invention are administered in combination with an endothelin antagonist such as by way of example and preferably bosentan, darusentan, ambrisentan or sitaxsentan.

In a preferred embodiment of the invention, the compounds according to the invention are administered in combination with a renin inhibitor such as by way of example and preferably aliskiren, SPP-600 or SPP-800.

In a preferred embodiment of the invention, the compounds according to the invention are administered in combination with a mineralocorticoid receptor antagonist such as by way of example and preferably spironolactone or eplerenone.

In a preferred embodiment of the invention, the compounds according to the invention are administered in combination with a Rho kinase inhibitor such as by way of example and preferably fasudil, Y-27632, SLx-2119, BF-66851, BF-66852, BF-66853, KI-23095, SB-772077, GSK-269962A or BA-1049.

In a preferred embodiment of the invention, the compounds according to the invention are administered in combination with a diuretic such as by way of example and preferably furosemide.

Agents which alter lipid metabolism preferably mean compounds from the group of CETP inhibitors, thyroid receptor agonists, cholesterol synthesis inhibitors such as HMG-CoA reductase inhibitors or squalene synthesis inhibitors, of ACAT inhibitors, MTP inhibitors, PPAR-alpha, PPAR-gamma and/or PPAR-delta agonists, cholesterol absorption inhibitors, polymeric bile acid adsorbents, bile acid reabsorption inhibitors, lipase inhibitors and lipoprotein(a) antagonists.

In a preferred embodiment of the invention, the compounds according to the invention are administered in combination with a CETP inhibitor such as by way of example and preferably torcetrapib (CP-529 414), JJT-705 or CETP vaccine (Avant).

In a preferred embodiment of the invention, the compounds according to the invention are administered in combination with a thyroid receptor agonist such as by way of example and preferably D-thyroxine, 3,5,3'-triiodothyronine (T3), CGS 23425 or axitirome (CGS 26214).

In a preferred embodiment of the invention, the compounds according to the invention are administered in combination with an HMG-CoA reductase inhibitor from the class of statins such as by way of example and preferably lovastatin, simvastatin, pravastatin, fluvastatin, atorvastatin, rosuvastatin, cerivastatin or pitavastatin.

In a preferred embodiment of the invention, the compounds according to the invention are administered in combination with a squalene synthesis inhibitor such as by way of example and preferably BMS-188494 or TAK-475.

In a preferred embodiment of the invention, the compounds according to the invention are administered in combination with an ACAT inhibitor such as by way of example and preferably avasimibe, melinamide, pactimibe, eflucimibe or SMP-797.

In a preferred embodiment of the invention, the compounds according to the invention are administered in combination with an MTP inhibitor such as by way of example and preferably implitapide, BMS-201038, R-103757 or JTT-130.

In a preferred embodiment of the invention, the compounds according to the invention are administered in combination with a PPAR-gamma agonist such as by way of example and preferably pioglitazone or rosiglitazone.

In a preferred embodiment of the invention, the compounds according to the invention are administered in combination with a PPAR-delta agonist such as by way of example and preferably GW-501516 or BAY 68-5042.

In a preferred embodiment of the invention, the compounds according to the invention are administered in combination with a cholesterol absorption inhibitor such as by way of example and preferably ezetimibe, tiqueside or pamaqueside.

In a preferred embodiment of the invention, the compounds according to the invention are administered in combination with a lipase inhibitor such as by way of example and preferably orlistat.

In a preferred embodiment of the invention, the compounds according to the invention are administered in combination with a polymeric bile acid adsorbent such as by way of example and preferably cholestyramine, colestipol, colesolvam, CholestaGel or colestimide.

In a preferred embodiment of the invention, the compounds according to the invention are administered in combination with a bile acid reabsorption inhibitor such as by way of example and preferably ASBT (=IBAT) inhibitors such as, for example, AZD-7806, S-8921, AK-105, BARI-1741, SC-435 or SC-635.

In a preferred embodiment of the invention, the compounds according to the invention are administered in combination with a lipoprotein(a) antagonist such as by way of example and preferably gemcabene calcium (CI-1027) or nicotinic acid.

The present invention further provides medicaments comprising at least one compound according to the invention, usually in combination with one or more inert, non-toxic, pharmaceutically suitable excipients, and their use for the purposes mentioned above.

The compounds according to the invention may have systemic and/or local effects. For this purpose, they can be administered in a suitable way such as, for example, by the oral, parenteral, pulmonary, nasal, sublingual, lingual, buccal, rectal, dermal, transdermal, conjunctival or otic route or as implant or stent.

The compounds according to the invention can be administered in administration forms suitable for these administration routes.

Suitable for oral administration are administration forms which function according to the prior art and deliver the compounds according to the invention rapidly and/or in a modified manner, and which contain the compounds of the invention in crystalline and/or amorphized and/or dissolved form, such as, for example, tablets (uncoated and coated tablets, for example having coatings which are resistant to gastric juice or are insoluble or dissolve with a delay and control the release of the compound of the invention), tablets which disintegrate rapidly in the mouth, or films/wafers, films/lyophilizates, capsules (for example hard or soft gelatin capsules), sugar-coated tablets, granules, pellets, powders, emulsions, suspensions, aerosols or solutions.

Parenteral administration can take place with avoidance of an absorption step (e.g. intravenous, intraarterial, intracardiac, intraspinal or intralumbar) or with inclusion of an absorption (e.g inhalative, intramuscular, subcutaneous, intracutaneous, percutaneous, or intraperitoneal). Administration forms suitable for parenteral administration are, inter alia, preparations for injection and infusion in the form of solutions, suspensions, emulsions, lyophilizates or sterile powders.

Suitable for the other routes of administration are, for example, pharmaceutical forms for inhalation (inter alia powder inhalers, nebulizers, aerosols), nasal drops, solutions, sprays; tablets for lingual, sublingual or buccal administration, films/wafers or capsules, suppositories, preparations for the ears and eyes, vaginal capsules, aqueous suspensions (lotions, shaking mixtures), lipophilic suspensions, ointments, creams, transdermal therapeutic systems (for example patches), milk, pastes, foams, dusting powders, implants or stents.

Oral or parenteral administration are preferred, especially oral and intravenous administration and administration by inhalation.

The compounds according to the invention can be converted into the stated administration forms. This can take place in a manner known per se by mixing with inert, non-toxic, pharmaceutically suitable excipients. These excipients include inter alia carriers (for example microcrystalline cellulose, lactose, mannitol), solvents (e.g. liquid polyethylene glycols), emulsifiers and dispersants or wetting agents (for example sodium dodecyl sulphate, polyoxysorbitan oleate), binders (for example polyvinylpyrrolidone), synthetic and natural polymers (for example albumin), stabilizers (e.g. antioxidants such as, for example, ascorbic acid), colorings (e.g. inorganic pigments such as, for example, iron oxides) and masking flavors and/or odors.

It has generally proved to be advantageous on parenteral administration to administer amounts of about 0.001 to 1 mg/kg, preferably about 0.01 to 0.5 mg/kg of body weight per day to achieve effective results. On oral administration, the dosage is about 0.01 to 100 mg/kg, preferably about 0.01 to 20 mg/kg, and very particularly preferably about 0.1 to 10 mg/kg of body weight.

It may nevertheless be necessary where appropriate to deviate from the stated amounts, in particular as a function of body weight, administration route, individual response to the active ingredient, type of preparation and time or interval over which administration takes place. Thus, in some cases it may be sufficient to make do with less than the aforementioned minimum amount, whereas in other cases the upper limit mentioned must be exceeded. Where relatively large amounts are administered, it may be advisable to distribute these in a plurality of single doses over the day.

The following exemplary embodiments illustrate the invention. The invention is not restricted to the examples.

The percentage data in the following tests and examples are, unless indicated otherwise, percentages by weight; parts are parts by weight. Solvent ratios, dilution ratios and concentration data of liquid/liquid solutions are based in each case on the volume.

A. EXAMPLES

Abbreviations and Acronyms:
aq. aqueous, aqueous solution
c concentration
cat. catalytic
CDI N,N'-carbonyldiimidazole
TLC thin-layer chromatography
DCI direct chemical ionization (in MS)
dist. distilled
DIEA N,N-diisopropylethylamine
DMAP 4-N,N-dimethylaminopyridine
DMF dimethylformamide
DMSO dimethyl sulphoxide
EDC N'-(3-dimethylaminopropyl)-N-ethylcarbodiimide hydrochloride
ee enantiomeric excess
ent enantiomerically pure, enantiomer
eq. equivalent(s)
ESI electrospray ionization (in MS)
Et ethyl
GC-MS gas chromatography-coupled mass spectrometry
h hour(s)
HATU O-(7-azabenzotriazol-1-yl)-N,N,N',N'-tetramethyluronium-hexafluorophosphate
HOBt 1-hydroxy-1H-benzotriazole hydrate
HPLC high-pressure, high-performance liquid chromatography
conc. concentrated
LC-MS liquid chromatography-coupled mass spectrometry
MCPBA meta-chloroperbenzoic acid
Me methyl
min minute(s)
MPLC medium-pressure liquid chromatography
MS mass spectrometry
MTBE methyl tert-butyl ether
NMR nuclear magnetic resonance spectrometry
Ph phenyl
PyBOP benzotriazol-1-yloxytris(pyrrolidino)phosphonium hexafluoro-phosphate
quant. quantitative (in yield)
rac racemic, racemate
RT room temperature
$R_t$ retention time (in HPLC)
m.p. melting point
tBu tert-butyl
TFA trifluoroacetic acid
TFAA trifluoroacetic anhydride
THF tetrahydrofuran
UV ultraviolet spectrometry
v/v volume to volume ratio (of a solution)
HPLC, LC-MS and GC-MS Methods:
Method 1 (LC-MS):

MS instrument type: Micromass ZQ; HPLC instrument type: Waters Alliance 2795; column: Phenomenex Synergi 2μ Hydro-RP Mercury 20 mm×4 mm; mobile phase A: 1 l of water+0.5 ml of 50% strength formic acid, mobile phase B: 1 l of acetonitrile+0.5 ml of 50% strength formic acid; gradient: 0.0 min 90% A→2.5 min 30% A→3.0 min 5% A→4.5 min 5% A; flow rate: 0.0 min 1 ml/min→2.5 min/3.0 min/4.5 min 2 ml/min; oven: 50° C.; UV detection: 210 nm.

Method 2 (LC-MS):

MS instrument type: Micromass ZQ; HPLC instrument type: HP 1100 Series; UV DAD; column: Phenomenex Gemini 3μ 30 mm×3.0 mm; mobile phase A: 1 l of water+0.5 ml of 50% strength formic acid, mobile phase B: 1 l of acetonitrile+0.5 ml 50% strength formic acid; gradient: 0.0 min 90% A→2.5 min 30% A→3.0 min 5% A→4.5 min 5% A; flow rate; 0.0 min 1 ml/min→2.5 min/3.0 min/4.5 min 2 ml/min; oven: 50° C.; UV detection: 210 nm.

Method 3 (LC-MS):

Instrument: Micromass Quattro LCZ with HPLC Agilent Series 1100; column: Phenomenex Onyx Monolithic C18, 100 mm×3 mm; mobile phase A: 1 l of water+0.5 ml of 50% strength formic acid, mobile phase B: 1 l of acetonitrile+0.5 ml of 50% strength formic acid; gradient: 0.0 min 90% A→2 min 65% A→4.5 min 5% A→6 min 5% A; flow rate: 2 ml/min; oven: 40° C.; UV detection: 208-400 nm.

Method 4 (LC-MS):

MS instrument type: Waters ZQ; HPLC instrument type: Waters Alliance 2795; column: Phenomenex Onyx Monolithic C18, 100 mm×3 mm; mobile phase A: 1 l of water+0.5 ml of 50% strength formic acid, mobile phase B: 1 l of acetonitrile+0.5 ml of 50% strength formic acid; gradient: 0.0 min 90% A→2 min 65% A→4.5 min 5% A→6 min 5% A; flow rate: 2 ml/min; oven: 40° C.; UV detection: 210 nm.

Method 5 (LC-MS):

Instrument: Micromass QuattroPremier with Waters HPLC Acquity; column: Thermo Hypersil GOLD 1.9μ 50 mm×1 mm; mobile phase A: 1 l of water+0.5 ml of 50% strength formic acid, mobile phase B: 1 l of acetonitrile+0.5 ml of 50% strength formic acid; gradient: 0.0 min 90% A→0.1 min 90% A→1.5 min 10% A→2.2 min 10% A; flow rate: 0.33 ml/min; oven: 50° C.; UV detection: 210 nm.

Method 6 (LC-MS):

MS instrument type: Micromass ZQ; HPLC instrument type: Waters Alliance 2795; column: Merck Chromolith SpeedROD RP-18e 100 mm×4.6 mm; mobile phase A: water+500 μl of 50% strength formic acid/litre; mobile phase B: acetonitrile+500 μl of 50% strength formic acid/litre; gradient: 0.0 min 10% B→7.0 min 95% B→9.0 min 95% B; flow rate: 0.0 min 1.0 ml/min 7.0 min 2.0 ml/min 9.0 min 2.0 ml/min; oven: 35° C.; UV detection: 210 nm.

Method 7 (LC-MS):

MS instrument type: Micromass ZQ; HPLC instrument type: Waters Alliance 2795; column: Phenomenex Synergi 2.5μ MAX-RP 100A Mercury 20 mm×4 mm; mobile phase A: 1 l of water+0.5 ml of 50% strength formic acid, mobile phase B: 1 l of acetonitrile+0.5 ml of 50% strength formic acid; gradient: 0.0 min 90% A→0.1 min 90% A→3.0 min 5% A→4.0 min 5% A→4.01 min 90% A; flow rate: 2 ml/min; oven: 50° C.; UV detection: 210 nm.

Method 8 (analytical HPLC):

Instrument: HP 1100 with DAD detection; column: Kromasil 100 RP-18, 60 mm×2.1 mm, 3.5 μm; mobile phase A: 5 ml of HClO$_4$ (70% strength)/1 of water, mobile phase B: acetonitrile; gradient: 0 min 2% B→0.5 min 2% B→4.5 min 90% B→9 min 90% B→9.2 min 2% B→10 min 2% B; flow rate: 0.75 ml/min; column temperature: 30° C.; UV detection: 210 nm.

Method 9 (analytical HPLC):

Instrument: HP 1100 with DAD detection; column: Kromasil 100 RP-18, 60 mm×2.1 mm, 3.5 μm; mobile phase A: 5 ml of HClO$_4$ (70% strength)/1 of water, mobile phase B: acetonitrile; gradient: 0 min 2% B→0.5 min 2% B→4.5 min 90% B→6.5 min 90% B→6.7 min 2% B→7.5 min 2% B; flow rate: 0.75 ml/min; column temperature: 30° C.; UV detection: 210 nm.

Method 10 (preparative HPLC):

Instrument: Abimed Gilson Pump 305/306, Manometric Module 806; column: GromSil C18, 250 mm×30 mm, 10 μm; mobile phase A: water+0.1% trifluoroacetic acid, mobile phase B: acetonitrile; gradient: 0-3 min 10% B, ramp 3.01-34 min 95% B, 34.01-38 min 95% B, 38.01-40 min 10% B; flow rate: 50 ml/min; UV detection: 210 nm.

Method 11 (preparative HPLC):

Instrument: Abimed Gilson Pump 305/306, Manometric Module 806; column: GromSil 1200DS-4HE, 250 mm×40 mm, 10 μm; mobile phase A: water+0.1% trifluoroacetic acid, mobile phase B: acetonitrile; gradient: 0-3 min 30% B, ramp 3.01-40 min 95% B, 40.01-50 min 95% B, 50.01-55 min 30% B; flow rate: 50 ml/min; UV detection: 210 nm.

Method 12 (preparative HPLC):

Instrument: Abimed Gilson Syringe Pump 402, Gilson 231XL Autosampler, Gilson Fraction Collector; software: Gilson UniPoint 2.10; column: Kromasil C18, 125 mm×20 mm, 5 μm, 100 Å; mobile phase A: water+0.01% formic acid, mobile phase B: acetonitrile; gradient: 0 min 10% B→2 min 10% B→9 min 90% B→12 min 90% B→12.1 min 10% B→15 min 10% B; flow rate: 0.35 ml/min; UV detection: 254 nm.

Method 13 (preparative HPLC):

Column: Gemini C18, 5 μm, 250 mm×21.2 mm (from Phenomenex); mobile phase: water/acetonitrile 2:3 (v/v); flow rate: 25 ml/min; temperature: 30° C.; UV detection: 210 nm.

Method 14 (preparative HPLC):

Column: XBridge C18, 5 μm OBD, 150 mm×19 mm (from Waters); mobile phase: water with 0.1% diethylamine/acetonitrile 3:2 (v/v); flow rate: 25 ml/min; temperature: 30° C.; UV detection: 235 nm.

Method 15 (preparative HPLC):

Column: Sunfire C18 OBD, 5 μm, 250 mm×20 mm; mobile phase: water with 0.2% trifluoroacetic acid/acetonitrile 6:4 (v/v); flow rate: 25 ml/min; temperature: 24° C.; UV detection: 210 nm.

Method 16 (GC-MS):

Instrument: Micromass GCT, GC 6890; column: Restek RTX-35, 15 m×200 μm×0.33 μm; constant flow of helium: 0.88 ml/min; oven: 70° C.; inlet: 250° C.; gradient: 70° C., 30° C./min 310° C. (maintained for 3 min)

Starting Materials and Intermediates:

Example 1A

4-Methyl-3-(methylsulphanyl)benzonitrile

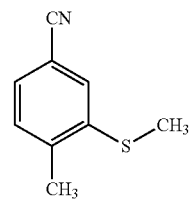

Method A:

The reaction was carried out under argon. 3-Fluoro-4-methylbenzonitrile (3000 mg, 22.2 mmol) and sodium methanethiolate (1572 mg, 20.2 mmol) were initially charged in DMF (30 ml), potassium carbonate (6973 mg, 50.5 mmol) was added and the mixture was stirred under reflux overnight. The reaction was then concentrated, the residue was suspended in methylene chloride/methanol (10:1) and the insoluble potassium carbonate was filtered off. The filtrate was reconcentrated and the residue was chromatographed on silica gel (mobile phase: cyclohexane/ethyl acetate 10:1). This gave 2.51 g (64% of theory) of the desired compound.

Method B:

The reaction was carried out with the aid of a washer filled with sodium hypochlorite solution. 3-Fluoro-4-methylbenzonitrile (200 g, 1479.9 mmol) was initially charged in DMF (1.5 liters) and warmed to 40° C., and sodium methanethiolate (altogether 126.8 g, 1627.9 mmol) was added a little at a time (about 25 g per portion). During the addition, the temperature increased to 100° C. The reaction mixture was stirred initially at a bath temperature of 175° C. for 1.5 h and then at room temperature overnight. The reaction mixture was then poured into water (7.5 liters) and extracted twice with ethyl acetate (1875 ml each). The combined organic phases were washed with saturated sodium chloride solution (1875 ml) and concentrated on a rotary evaporator, and the residue was chromatographed on silica gel (mobile phase: petroleum ether/ethyl acetate 95:5, about 30 liters). Removal of the solvent on a rotary evaporator and drying under high vacuum gave 172 g (71% of theory) of the desired compound.

GC-MS (Method 16): $R_t$=5.25 min; MS (ESIpos): m/z (%)=163.0 (100) $[M]^+$ $^1$H-NMR (400 MHz, $d_6$-DMSO): δ=2.30 (s, 3H), 2.54 (s, 3H), 7.38 (d, 1H), 7.52 (dd, 1H), 7.58 (br. s, 1H).

Example 2A

4-Methyl-3-(methylsulphonyl)benzonitrile

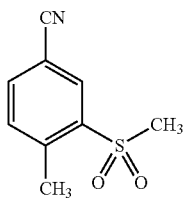

Method A:

4-Methyl-3-(methylsulphanyl)benzonitrile (14 050 mg, 80.1 mmol; Example 1A) was dissolved in dichloromethane (700 ml) and cooled to 0° C., and 3-chloroperbenzoic acid (50 923 mg, 206.6 mmol) was added slowly. The mixture was then stirred initially at 0° C. for 40 min and then at room temperature overnight. The precipitated 3-chlorobenzoic acid was filtered off, the filtrate was washed with 1N aqueous sodium hydroxide solution and the organic phase was dried over sodium sulphate and concentrated. The residue was purified by silica gel chromatography (mobile phase: cyclohexane/ethyl acetate 1:1, 1:2). This gave 13.65 g (81% of theory) of the desired compound.

Method B:

3-Chloroperbenzoic acid (2501 g, 10 144.4 mmol) was dissolved in 27.2 liters of dichloromethane and cooled to 10° C., and 4-methyl-3-(methylsulphanyl)benzonitrile (552 g, 3381.5 mmol; Example 1A) was added a little at a time. After the addition had ended, the mixture was stirred at RT for 5 h. The precipitated 3-chlorobenzoic acid was filtered off with suction and the solid was washed with dichloromethane (3 liters). The combined filtrates were stirred with 1N aqueous sodium hydroxide solution (15 liters), the mixture was filtered and the organic phase was separated off. The latter was once more stirred with 1N aqueous sodium hydroxide solution (15 liters), separated from the sodium hydroxide solution, dried and concentrated on a rotary evaporator. The residue was suspended in diethyl ether (4 liters), stirred for 10 min and then filtered. The solid was washed with a little diethyl ether and dried under high vacuum. This gave 613 g (93% of theory) of the desired compound.

GC-MS (Method 16): $R_t$=6.59 min; MS (ESIpos): m/z (%)=195.0 (100) $[M]^+$ $^1$H-NMR (400 MHz, $d_6$-DMSO): δ=2.30 (s, 3H), 2.54 (s, 3H), 7.38 (d, 1H), 7.52 (dd, 1H), 7.58 (br. s, 1H).

Example 3A

4-[2-(Dimethylamino)ethenyl]-3-(methylsulphonyl)benzonitrile

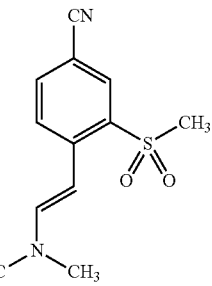

Method A:

The reaction was carried out under argon. At 140° C., 4-methyl-3-(methylsulphonyl)benzonitrile (13.0 g, 66.6 mmol; Example 2A) and 1,1-dimethoxy-N,N-dimethylmethanamine (10.315 g, 86.6 mmol) were stirred in DMF (200 ml) for 14 h. To bring the reaction to completion, more 1,1-dimethoxy-N,N-dimethylmethanamine (3.967 g, 33.3 mmol) was then added, and the mixture was stirred at 140° C. for a further 24 h. The DMF was then removed on a rotary evaporator, and the residue was reacted without further purification in the next step.

Method B:

The reaction was carried out under argon. 4-Methyl-3-(methylsulphonyl)benzonitrile (612 g, 3134.6 mmol; Example 2A) was initially charged in DMF (6.12 liters), 1,1-dimethoxy-N,N-di-methylmethanamine (859 g, 7209.5 mmol) was added and the mixture was stirred at 140° C. for 7 h. The reaction mixture was then poured into 35 liters of 10% strength sodium chloride solution and extracted twice with in each case 10 liters of ethyl acetate. The combined organic phases were washed with saturated sodium chloride solution (5 liters), dried and concentrated on a rotary evaporator, and the residue was dried under high vacuum overnight. This gave 1098 g (98% of theory) of the desired compound.

GC-MS (Method 16): $R_t$=8.95 min; MS (ESIpos): m/z (%)=250.0 (10) $[M]^+$.

Example 4A

4-Formyl-3-(methylsulphonyl)benzonitrile

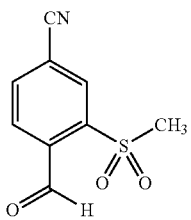

Method A:

4-[2-(Dimethylamino)ethenyl]-3-(methylsulphonyl)benzonitrile (16 666 mg, 66.6; Example 3A) was initially charged in water/THF (1:1, 500 ml), sodium periodate (42 722 mg, 199.7 mmol) was added and the mixture was stirred at room temperature overnight. The precipitated solid was filtered off and washed with ethyl acetate. The combined organic phases were washed with saturated sodium bicarbonate solution and saturated sodium chloride solution, dried over sodium sulphate, filtered and concentrated. The residue was purified by silica gel chromatography (mobile phase: cyclohexane/ethyl acetate 1:1). This gave 4.6 g (33% of theory) of the desired compound.

Method B:

4-[2-(Dimethylamino)ethenyl]-3-(methylsulphonyl)benzonitrile (1098 g, 3070.5 mmol; Example 3A) was initially charged in THF/water (1:1, 13.8 liters), sodium periodate (1970 g, 9211.4 mmol) was added and the mixture was stirred at room temperature for 1 h. The precipitated solid was filtered off with suction and washed with ethyl acetate (17 liters). Water (17 liters) was added to the combined filtrates, and after the extraction the aqueous phase was removed. The organic phase was washed with saturated sodium bicarbonate solution (8.5 liters) and saturated sodium chloride solution (8.5 liters), and then dried and concentrated on a rotary evaporator. The residue was purified by silica gel chromatography (mobile phase: dichloromethane/ethyl acetate 9:1, 60 liters). The product fractions were concentrated, the residue was suspended in petroleum ether and then filtered off with suction and the solid was dried under high vacuum overnight. This gave 436 g (65% of theory) of the desired compound.

GC-MS (Method 16): $R_t$=6.89 min; MS (ESIpos): m/z (%)=191.1 (15) [M-18]$^+$, 161.0 (100)

$^1$H-NMR (400 MHz, d$_6$-DMSO): δ=3.57 (s, 3H), 8.10 (d, 1H), 8.39 (dd, 1H), 8.45 (d, 1H), 10.63 (s, 1H).

Example 5A

Ethyl (4R)-4-(4-cyanophenyl)-6-methyl-2-oxo-1-[3-(trifluoromethyl)phenyl]-1,2,3,4-tetrahydro-pyrimidine-5-carboxylate

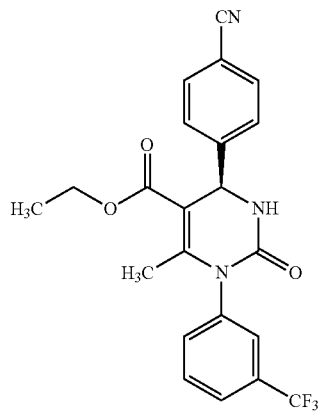 [SMILES: CCOC(=O)C1=C(C)N(c2cccc(C(F)(F)F)c2)C(=O)N[C@@H]1c1ccc(C#N)cc1]

The title compound was prepared as described in WO 2008/003412 (Example 1).

Example 6A

Ethyl (4R)-6-(bromomethyl)-4-(4-cyanophenyl)-2-oxo-1-[3-(trifluoromethyl)phenyl]-1,2,3,4-tetrahydropyrimidine-5-carboxylate

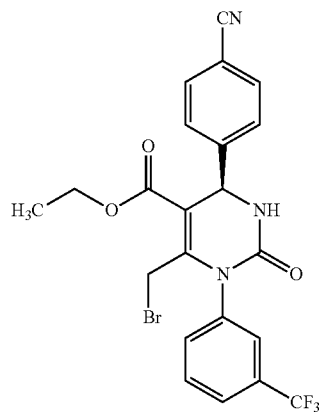 [SMILES: CCOC(=O)C1=C(CBr)N(c2cccc(C(F)(F)F)c2)C(=O)N[C@@H]1c1ccc(C#N)cc1]

20 g (46.576 mmol) of the compound described in Example 5A were dissolved in 350 ml of chloroform, and 8.2 g (51.234 mmol) of bromine were added at 0° C. The ice-bath was removed, and the mixture was stirred for one hour. The mixture was then washed with 10% strength sodium thiosulphate solution, and the organic phase was removed and dried over sodium sulphate. After filtration, the solution was concentrated on a rotary evaporator and the residue was triturated with diethyl ether. The solid was filtered off with suction and dried under reduced pressure. This gave 21.1 g (87% of theory) of the target compound.

LC-MS (Method 1): $R_t$=2.41 min; MS (ESIpos): m/z=510 [M+H]$^+$.

For the $^1$H-NMR data of the racemic compound see WO 2004/024700 (Example 19).

Example 7A

[(6R)-6-(4-Cyanophenyl)-5-(ethoxycarbonyl)-4-methyl-2-oxo-3-[3-(trifluoromethyl)phenyl]-3,6-dihydropyrimidin-1(2H)-yl]acetic acid

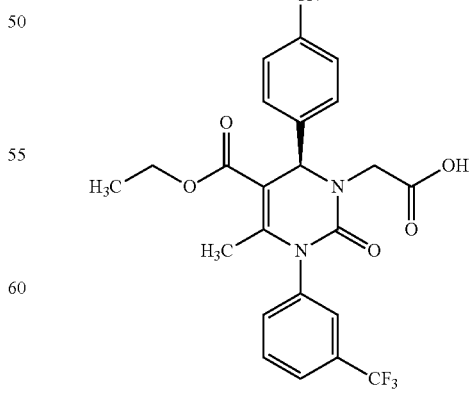

The title compound was prepared as described in WO 2008/003412 (Example 13).

Example 8A

Ethyl (4R)-3-(2-amino-2-oxoethyl)-4-(4-cyanophenyl)-6-methyl-2-oxo-1-[3-(trifluoromethyl)-phenyl]-1,2,3,4-tetrahydropyrimidine-5-carboxylate

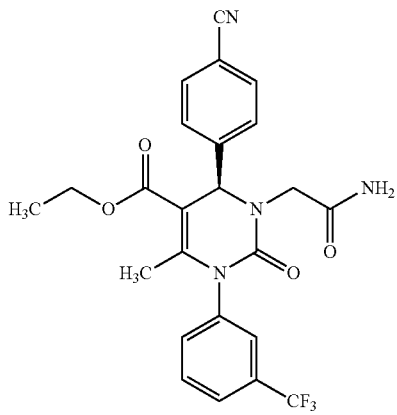 [SMILES: CCOC(=O)C1=C(C)N(c2cccc(C(F)(F)F)c2)C(=O)N(CC(N)=O)[C@@H]1c1ccc(C#N)cc1]

The title compound was prepared as described in WO 2008/003412 (Example 22).

Example 9A

Ethyl (4R)-4-(4-cyanophenyl)-3-[2-(dimethylamino)-2-oxoethyl]-6-methyl-2-oxo-1-[3-(trifluoromethyl)phenyl]-1,2,3,4-tetrahydropyrimidine-5-carboxylate

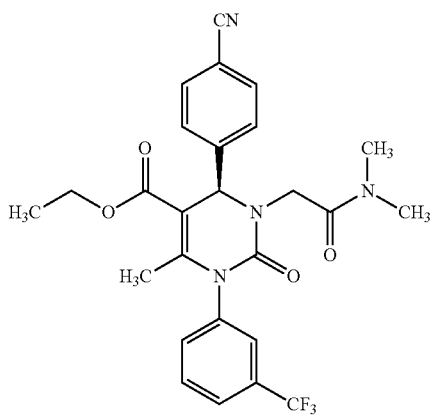 [SMILES: CCOC(=O)C1=C(C)N(c2cccc(C(F)(F)F)c2)C(=O)N(CC(=O)N(C)C)[C@@H]1c1ccc(C#N)cc1]

The title compound was prepared as described in WO 2008/003412 (Example 30).

Example 10A

Ethyl (4R)-4-(4-cyanophenyl)-6-methyl-2-oxo-3-(2-oxo-2-pyrrolidin-1-ylethyl)-1-[3-(trifluoromethyl)phenyl]-1,2,3,4-tetrahydropyrimidine-5-carboxylate

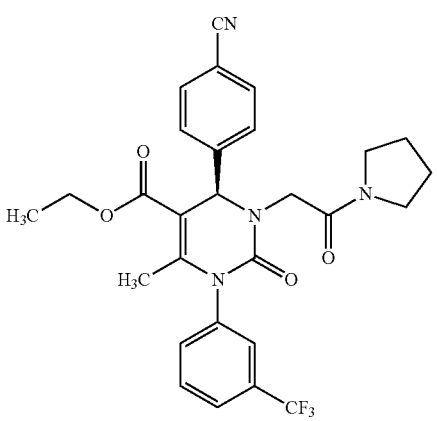 [SMILES: CCOC(=O)C1=C(C)N(c2cccc(C(F)(F)F)c2)C(=O)N(CC(=O)N2CCCC2)[C@@H]1c1ccc(C#N)cc1]

500 mg (1.026 mmol) of the compound described in Example 7A were dissolved in 1.5 ml of DMF, and 161 mg (2.257 mmol) of pyrrolidine, 251 mg (2.052 mmol) of DMAP, 305 mg (2.257 mmol) of HOBt and 393 mg (2.052 mmol) of EDC were added in succession. The mixture was stirred at room temperature overnight and then purified directly, without further work-up, by preparative HPLC (Method 10). This gave 239 mg (41% of theory) of the target compound.

LC-MS (Method 2): $R_t$=2.67 min; MS (ESIpos): m/z (%)=541.2 (100) [M+H]$^+$.

$^1$H-NMR (400 MHz, $d_6$-DMSO): δ=1.12 (t, 3H), 1.74 (m, 2H), 1.84 (m, 2H), 2.04 (s, 3H), 3.29 (m, 4H), 3.58 (d, 1H), 4.05 (m, 2H), 4.35 (d, 1H), 5.53 (s, 1H), 7.61 (d, 1H), 7.67 (d, 2H), 7.72 (t, 2H), 7.81 (d, 1H), 7.88 (d, 2H).

Analogously to the procedure for Example 10A, the compound in the table below was prepared from the starting material prepared in Example 7A and 2-(methylamino)ethanol:

| Example | Structure | Yield | Analytical data |
|---|---|---|---|
| 11A | 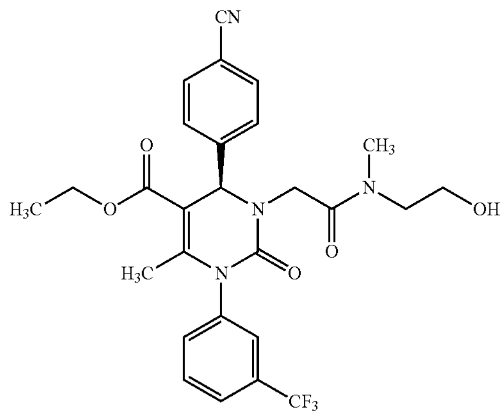 [SMILES: CCOC(=O)C1=C(C)N(c2cccc(C(F)(F)F)c2)C(=O)N(CC(=O)N(C)CCO)[C@@H]1c1ccc(C#N)cc1] | 77% of theory | LC-MS (Method 3): $R_t$ = 3.46 min; MS (ESIpos): m/z = 545 [M + H]⁺. |

Example 12A

Ethyl (4R)-3-(2-amino-2-oxoethyl)-6-(bromomethyl)-4-(4-cyanophenyl)-2-oxo-1-[3-(trifluoromethyl)phenyl]-1,2,3,4-tetrahydropyrimidine-5-carboxylate

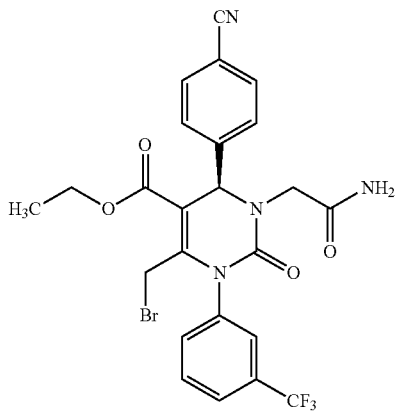 [SMILES: CCOC(=O)C1=C(CBr)N(c2cccc(C(F)(F)F)c2)C(=O)N(CC(N)=O)[C@@H]1c1ccc(C#N)cc1]

600 mg (1.233 mmol) of the compound described in Example 8A were dissolved in 15 ml of chloroform, and 197 mg (1.233 mmol) of bromine were added at 0° C. The ice-bath was removed, and the mixture was stirred for one hour. The mixture was then washed with 10% strength sodium thiosulphate solution, and the organic phase was separated off and dried over sodium sulphate. After filtration, the solution was concentrated on a rotary evaporator and the residue was purified by preparative HPLC (Method 11). This gave 479 mg (69% of theory) of the target compound.

LC-MS (Method 4): $R_t$=3.43 min; MS (ESIpos): m/z (%)=567.1 (100) [M+H]⁺.

¹H-NMR (400 MHz, d₆-DMSO): δ=1.16 (t, 3H), 3.41 (d, 1H), 4.11 (m, 3H), 4.27 (br. s, 1H), 4.46 (br. s, 1H), 5.58 (s, 1H), 7.13 (s, 1H), 7.43 (s, 1H), 7.66 (d, 2H), 7.75 (d, 2H), 7.81 (s, 1H), 7.87 (d, 1H), 7.92 (d, 2H).

Analogously to the procedure for Example 12A, the starting materials stated were used to prepare the compounds in the table below:

| Example | Structure | Starting material | Yield | Analytical data |
|---|---|---|---|---|
| 13A | 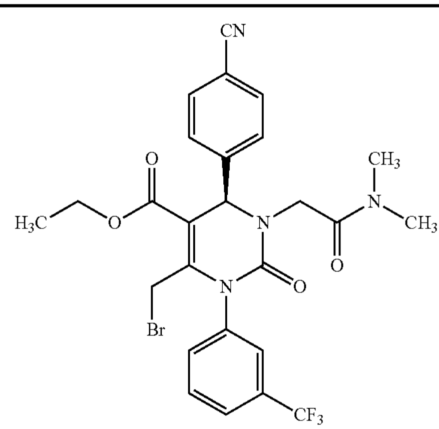 | 9A | 75% of theory | LC-MS (Method 2): $R_t$ = 2.68 min; MS (ESIpos): m/z = 595 [M + H]⁺. |

| Example | Structure | Starting material | Yield | Analytical data |
|---|---|---|---|---|
| 14A | 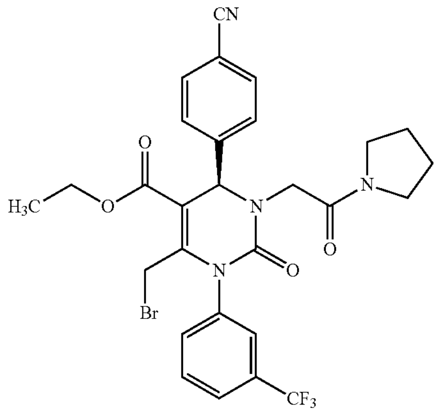 [SMILES: CCOC(=O)C1=C(CBr)N(c2cccc(C(F)(F)F)c2)C(=O)N(CC(=O)N2CCCC2)[C@@H]1c1ccc(C#N)cc1] | 10A | 39% of theory | LC-MS (Method 3): R$_t$ = 3.88 min; MS (ESIpos): m/z = 621 [M + H]$^+$. |
| 15A | 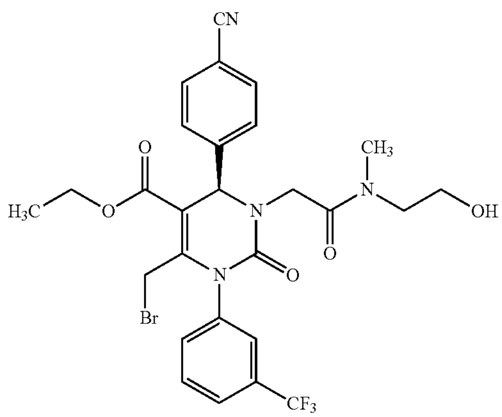 [SMILES: CCOC(=O)C1=C(CBr)N(c2cccc(C(F)(F)F)c2)C(=O)N(CC(=O)N(C)CCO)[C@@H]1c1ccc(C#N)cc1] | 11A | 65% of theory | LC-MS (Method 4): R$_t$ = 3.45 min; MS (ESIpos): m/z = 625 [M + H]$^+$. |

Example 16A

Ethyl (4R)-4-(4-cyanophenyl)-3-(2-methoxy-2-oxo-ethyl)-6-methyl-2-oxo-1-[3-(trifluoromethyl)-phenyl]-1,2,3,4-tetrahydropyrimidine-5-carboxylate

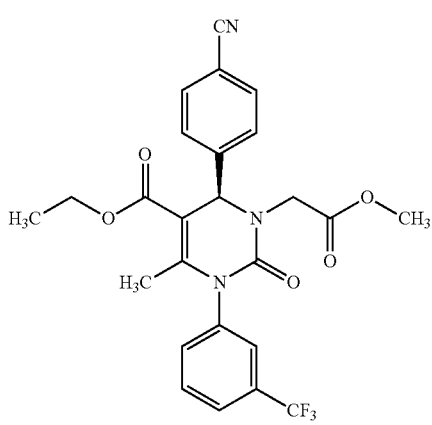 [SMILES: CCOC(=O)C1=C(C)N(c2cccc(C(F)(F)F)c2)C(=O)N(CC(=O)OC)[C@@H]1c1ccc(C#N)cc1]

500 mg (1.164 mmol) of the compound from Example 5A were stirred together with 220 mg (1.397 mmol) of methyl bromoacetate and 322 mg (2.329 mmol) of potassium carbonate in 20 ml of DMF at 60° C. overnight. The solid was then filtered off, the filtrate was concentrated on a rotary evaporator, the residue was dissolved in dichloromethane and this solution was washed three times with water. The organic phase was separated off, dried over sodium sulphate, filtered and concentrated. The crude product was purified by chromatography on silica gel (mobile phase toluene/ethyl acetate 3:1). This gave 419 mg (72% of theory) of the desired product.

LC-MS (Method 4): R$_t$=3.76 min; MS (ESIpos): m/z (%)=502.1 (100) [M+H]$^+$; MS (ESIneg): m/z (%)=500.2 (100) [M−H]$^-$.

$^1$H-NMR (400 MHz, d$_6$-DMSO): δ=7.89 (d, 2H), 7.83 (d, 1H), 7.79 (s, 1H), 7.74 (t, 2H), 7.70 (s, 1H), 7.67 (d, 1H), 5.64 (s, 1H), 4.19 (d, 1H), 4.05 (m, 2H), 3.93 (d, 1H), 3.56 (s, 3H), 2.07 (s, 3H), 1.12 (t, 3H).

Example 17A

Ethyl (4R)-6-(bromomethyl)-4-(4-cyanophenyl)-3-(2-methoxy-2-oxoethyl)-2-oxo-1-[3-(trifluoromethyl)phenyl]-1,2,3,4-tetrahydropyrimidine-5-carboxylate

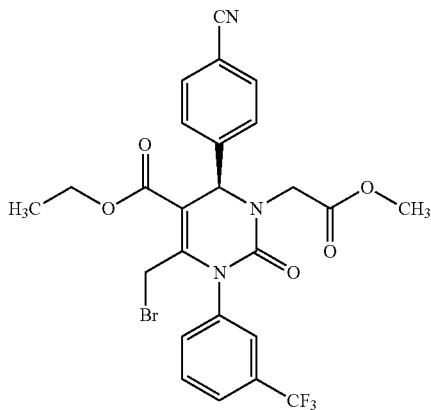 [SMILES: CCOC(=O)C1=C(CBr)N(c2cccc(C(F)(F)F)c2)C(=O)N(CC(=O)OC)[C@@H]1c1ccc(C#N)cc1]

100 mg (0.199 mmol) of the compound described in Example 16A were dissolved in 2 ml of chloroform, and 35 mg (0.219 mmol) of bromine were added at 0° C. After 30 minutes, the ice-bath was removed, and the mixture was stirred overnight. The mixture was then washed three times with 10% strength sodium thiosulphate solution. The combined aqueous phases were re-extracted with dichloromethane. The combined organic phases were dried over sodium sulphate, filtered and freed from the solvent under reduced pressure. Purification of the crude product by preparative HPLC (Method 10) gave 65 mg (54% of theory) of the target compound.

LC-MS (Method 2): $R_t$=2.83 min; MS (ESIpos): m/z (%)=582.0 (100) [M+H]$^+$.

$^1$H-NMR (400 MHz, d$_6$-DMSO): δ=7.91 (d, 2H), 7.88 (d, 1H), 7.79 (br. s, 1H), 7.78-7.71 (m, 2H), 7.69 (d, 2H), 5.69 (s, 1H), 4.60 (br. d, 1H), 4.19 (d, 1H), 4.17-4.09 (m, 3H), 4.02 (d, 1H), 3.54 (s, 3H), 1.15 (t, 3H).

Example 18A (rac)-Ethyl 4-(4-cyano-2-(methylsulphonyl)phenyl)-6-methyl-2-oxo-1-[3-(trifluoromethyl)phenyl]-1,2,3,4-tetrahydropyrimidine-5-carboxylate

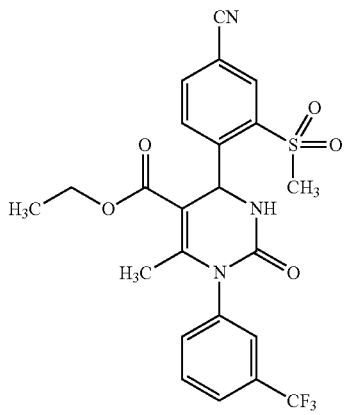 [SMILES: CCOC(=O)C1=C(C)N(c2cccc(C(F)(F)F)c2)C(=O)NC1c1ccc(C#N)cc1S(C)(=O)=O]

The reaction was carried out under argon. Triethyl phosphate (4.18 g, 22.9 mmol) and di-phosphorus pentoxide (2.17 g, 15.3 mmol) were stirred at 50° C. overnight. The mixture was then diluted with methyl tert-butyl ether (60 ml), and 4-formyl-3-(methylsulphonyl)benzonitrile (4.00 g, 19.1 mmol; Example 4A), 1-[3-(trifluoromethyl)phenyl]urea (3.90 g, 19.1 mmol) and ethyl acetoacetate (3.73 g, 28.7 mmol) were added. The mixture was stirred under reflux overnight. The precipitate formed was filtered off with suction and washed with diethyl ether (300 ml). Since the reaction had not gone to completion, more triethyl phosphate (5.36 g, 29.4 mmol) and diphosphorus pentoxide (2.71 g, 19.1 mmol) were stirred at 50° C. overnight and then stirred together with the solid isolated beforehand and methyl tert-butyl ether (25 ml) under reflux for another night. The precipitate formed was once more filtered off with suction and washed with diethyl ether. This gave 5.93 g (61% of theory) of the target compound.

HPLC (Method 8): $R_t$=4.56 min; MS (DCI/NH$_3$): m/z=508.1 [M+H]$^+$, 525 [M+NH$_4$]$^+$ $^1$H-NMR (400 MHz, d$_6$-DMSO): δ=0.94 (t, 3H), 2.13 (s, 3H), 3.50 (s, 3H), 3.89-4.02 (q, 2H), 6.41 (s, 1H), 7.25 (s, 1H), 7.68-7.90 (m, 4H), 8.09 (d, 1H), 8.26 (d, 1H), 8.39 (s, 1H).

Example 19A (rac)-Ethyl 6-(bromomethyl)-4-[4-cyano-2-(methylsulphonyl)phenyl]-2-oxo-1-[3-(trifluoromethyl)phenyl]-1,2,3,4-tetrahydropyrimidine-5-carboxylate

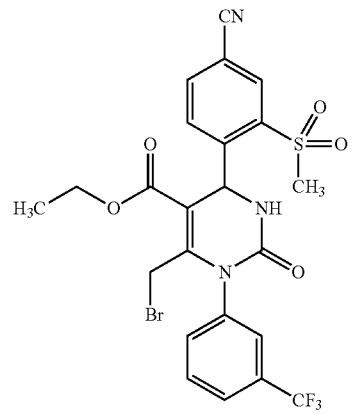

The compound described in Example 18A (3.00 g, 5.62 mmol) was dissolved in chloroform (50 ml), and bromine (987 mg, 6.18 mmol) was added at 0° C. The ice-bath was removed, and the mixture was stirred for one hour. The mixture was then washed with 10% strength sodium thiosulphate solution, and the organic phase was separated off and dried over sodium sulphate. After filtration, the solution was concentrated on a rotary evaporator and the residue was triturated with diethyl ether. The solid was filtered off with suction and dried under reduced pressure. This gave 2.97 g (90% of theory) of the target compound.

HPLC (Method 8): $R_t$=4.73 min; MS (DCI/NH$_3$): m/z=586, 588 [M+H]$^+$, 603, 605 [M+NH$_4$]$^+$ $^1$H-NMR (400 MHz, d$_6$-DMSO): δ=0.97 (t, 3H), 3.50 (s, 3H), 3.96-4.07 (q, 2H), 4.13-4.24 (d, 1H), 4.65-4.75 (d, 1H), 6.48 (d, 1H), 7.46 (d, 1H), 7.72-8.12 (m, 5H), 8.31 (d, 1H), 8.42 (s, 1H).

Example 20A (rac)-Ethyl 6-methyl-4-[4-cyano-2-(trifluoromethyl)phenyl]-2-oxo-1-[3-(trifluoromethyl)phenyl]-1,2,3,4-tetrahydropyrimidine-5-carboxylate

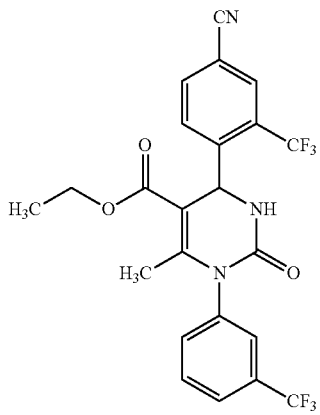 [SMILES: CCOC(=O)C1=C(C)N(c2cccc(C(F)(F)F)c2)C(=O)NC1c1ccc(C#N)cc1C(F)(F)F]

The reaction was carried out under argon. 4-Formyl-3-(trifluoromethyl)benzonitrile (996 mg, 5.0 mmol; for the preparation cf. WO 98/37058), 1-[3-(trifluoromethyl)phenyl]urea (1.02 g, 5.0 mmol) and ethyl acetoacetate (651 mg, 5.0 mmol) were added successively to a solution of ethyl polyphosphate (2.0 g; prepared from triethyl phosphate and diphosphorus pentoxide analogously to the process in Example 18A) in THF (25 ml). The mixture was stirred under reflux for 19 h and then concentrated. Ethyl acetate (150 ml) was added to the residue, and the mixture was washed successively with water (50 ml), saturated sodium bicarbonate solution (50 ml) and saturated sodium chloride solution (50 ml). The organic phase was dried over sodium sulphate and concentrated. The residue was purified by silica gel chromatography (mobile phase: cyclohexane→cyclohexane/ethyl acetate 2:1). This gave 1.55 g (62% of theory) of the target product.

LC-MS (Method 2): $R_t$=2.81 min; MS (ESIpos): m/z (%)=498 (100) [M+H]$^+$; MS (ESIneg): m/z (%)=453.0 (100), 469.2 (80) [M–H]$^-$.

$^1$H-NMR (400 MHz, d$_6$-DMSO): δ=0.85 (t, 3H), 2.10 (s, 3H), 3.90 (q, 2H), 5.75 (s, 1H), 7.70-7.90 (m, 4H), 8.00-8.15 (m, 2H), 8.20 (d, 1H), 8.30 (s, 1H).

Example 21A (rac)-Ethyl 6-(bromomethyl)-4-[4-cyano-2-(trifluoromethyl)phenyl]-2-oxo-1-[3-(trifluoromethyl)phenyl]-1,2,3,4-tetrahydropyrimidine-5-carboxylate

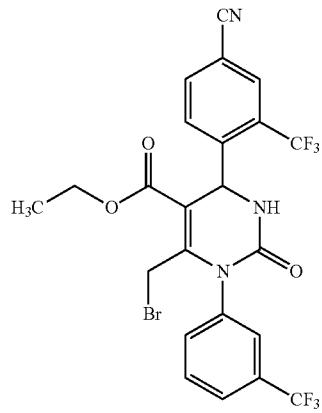 [SMILES: CCOC(=O)C1=C(CBr)N(c2cccc(C(F)(F)F)c2)C(=O)NC1c1ccc(C#N)cc1C(F)(F)F]

The compound described in Example 20A (497 mg, 1.0 mmol) was dissolved in chloroform (10 ml), and bromine (176 mg, 1.10 mmol) was added at 0° C. The ice-bath was removed, and the mixture was stirred at RT for 1.5 h. Dichloromethane (100 ml) was then added, and the reaction mixture was washed successively with 10% strength aqueous sodium thiosulphate solution (70 ml) and concentrated aqueous sodium chloride solution (50 ml). The organic phase was separated off, dried over sodium sulphate, filtered and concentrated on a rotary evaporator. This gave 735 mg (quant.) of the target compound, which was reacted further without any further work-up.

LC-MS (Method 3): $R_t$=4.08 min; MS (ESIpos): m/z (%)=576 (40) [M+H]$^+$.

Example 22A

N-[4-Fluoro-3-(trifluoromethyl)phenyl]urea

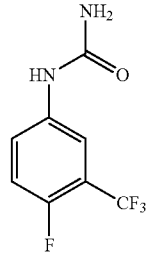 [SMILES: NC(=O)Nc1ccc(F)c(C(F)(F)F)c1]

2500 mg (13.957 mmol) of 4-fluoro-3-(trifluoromethyl)aniline were dissolved in 15 ml of 1 N hydrochloric acid, and 1132 mg (13.957 mmol) of potassium cyanate were added. The suspension was stirred at room temperature overnight and then diluted with ethyl acetate such that a clear two-phase solution was formed. The organic phase was separated off and the aqueous phase was extracted with ethyl acetate. The combined organic phases were dried and the solvent was removed on a rotary evaporator, and the crude product was then chromatographed on silica gel (mobile phase: dichloromethane/methanol 80:1, then 10:1). This gave 2180 mg (70% of theory) of the title compound.

LC-MS (Method 2): $R_t$=1.82 min; MS (ESIpos): m/z (%)=223.0 (100) [M+H]$^+$.

Example 23A

Ethyl 4-(4-cyanophenyl)-1-[4-fluoro-3-(trifluoromethyl)phenyl]-6-methyl-2-oxo-1,2,3,4-tetrahydropyrimidine-5-carboxylate

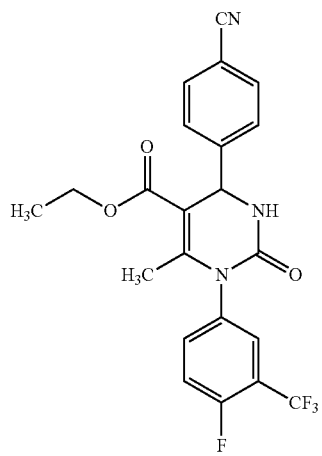 [SMILES: CCOC(=O)C1=C(C)N(c2ccc(F)c(C(F)(F)F)c2)C(=O)NC1c1ccc(C#N)cc1]

The reaction was carried out under argon. In succession, 4-formylbenzonitrile (656 mg, 5.0 mmol), 1-[4-fluoro-3-(trifluoromethyl)phenyl]urea (1.11 g, 5.0 mmol) and ethyl acetoacetate (651 mg, 5.0 mmol) were added to a solution of ethyl polyphosphate (2.0 g; prepared from triethyl phosphate and diphosphorus pentoxide analogously to the process in Example 18A) in THF (25 ml). The mixture was stirred under reflux for 19 h and then concentrated. Ethyl acetate (150 ml) was added to the residue, and the mixture was washed successively with water (50 ml), saturated sodium bicarbonate solution (50 ml) and saturated sodium chloride solution (50 ml). The organic phase was dried over sodium sulphate and concentrated. The residue was purified by silica gel chromatography (mobile phase: cyclohexane→cyclohexane/ethyl acetate 2:3). This gave 1.40 g (63% of theory) of the target product.

LC-MS (Method 1): $R_t$=2.42 min; MS (ESIpos): m/z (%)=448.2 (100) [M+H]$^+$; MS (ESIneg): m/z (%)=446.2 (100) [M−H]$^-$.

Example 24A

Ethyl 4-(4-cyanophenyl)-1-[4-fluoro-3-(trifluoromethyl)phenyl]-6-(bromomethyl)-2-oxo-1,2,3,4-tetrahydropyrimidine-5-carboxylate

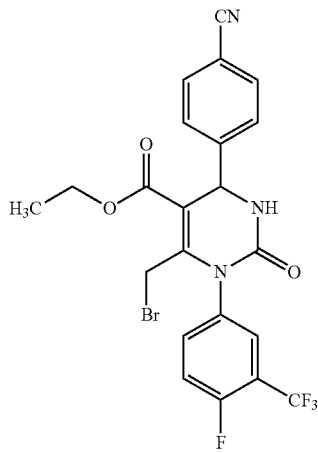 [SMILES: CCOC(=O)C1=C(CBr)N(c2ccc(F)c(C(F)(F)F)c2)C(=O)NC1c1ccc(C#N)cc1]

Ethyl 4-(4-cyanophenyl)-1-[4-fluoro-3-(trifluoromethyl)phenyl]-6-methyl-2-oxo-1,2,3,4-tetrahydropyrimidine-5-carboxylate (447 mg, 1.0 mmol) was dissolved in chloroform (10 ml) and bromine (176 mg, 1.10 mmol) was added at 0° C. The ice bath was removed and the mixture was stirred at room temperature for 0.5 h. The reaction mixture was then diluted with chloroform (20 ml) and washed successively with 10% strength aqueous sodium thiosulphate solution (10 ml) and concentrated aqueous sodium chloride solution (10 ml). The organic phase was separated off, dried over sodium sulphate, filtered and concentrated on a rotary evaporator. This gave 570 mg (quant.) of the target compound which was reacted further without further purification.

LC-MS (Method 2): $R_t$=2.79 min; MS (ESIpos): m/z (%)=526.0 (100) [M+H]$^+$.

Exemplary Embodiments

Example 1

4-{(4R)-7-Methyl-2,5-dioxo-1-[3-(trifluoromethyl)phenyl]-1,2,3,4,5,6,7,8-octahydropyrimido-[4,5-d]pyridazin-4-yl}benzonitrile

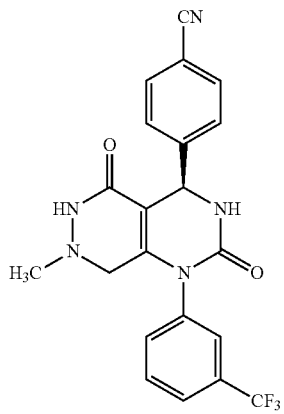 [SMILES: CN1CC2=C(C(=O)N1)[C@@H](c1ccc(C#N)cc1)NC(=O)N2c1cccc(C(F)(F)F)c1]

101 g (198.7 mmol) of ethyl (4R)-6-(bromomethyl)-4-(4-cyanophenyl)-2-oxo-1-[3-(trifluoromethyl)phenyl]-1,2,3,4- tetrahydropyrimidine-5-carboxylate (Example 6A) were initially charged in 2400 ml of dioxane. 27.46 g (596.1 mmol) of methylhydrazine were added dropwise to the solution, and the reaction mixture was then stirred at boiling point for 3 h. The mixture was then concentrated, and the residue was dissolved in dichloromethane and washed with water. The organic phase was dried over sodium sulphate and concentrated. The residue that remained was chomatographed on silica gel (mobile phase: dichloromethane/methanol 95:5). The solid which was obtained after concentration of the product fractions was triturated with diethyl ether, filtered off with suction and then dried at 50° C. under reduced pressure for 4 days. This gave 56.8 g (66% of theory) of the title compound.

LC-MS (Method 2): $R_t$=1.99 min; MS (ESIpos): m/z (%)=428.1 (100) [M+H]$^+$; MS (ESIneg): m/z (%)=426.2 (100) [M−H]$^-$.

$^1$H-NMR (400 MHz, $d_6$-DMSO): δ=2.36 (s, 3H), 3.06-3.14 (d, 1H), 3.60-3.69 (d, 1H), 5.42 (d, 1H), 7.64-7.74 (m, 4H), 7.78-7.86 (d, 2H), 7.88-7.90 (d, 2H), 8.30 (d, 1H), 8.86 (s, 1H).

Example 2

(rac)-4-[7-Methyl-2,5-dioxo-1-[3-(trifluoromethyl) phenyl]-1,2,3,4,5,6,7,8-octahydropyrimido-[4,5-d] pyridazin-4-yl]-3-(methylsulphonyl)benzonitrile

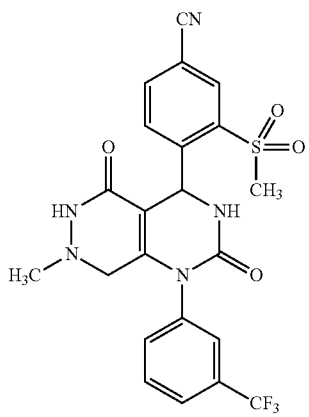 [SMILES: CN1CC2=C(C(=O)N1)C(c1ccc(C#N)cc1S(C)(=O)=O)NC(=O)N2c1cccc(C(F)(F)F)c1]

Ethyl 6-(bromomethyl)-4-[4-cyano-2-(methylsulphonyl) phenyl]-2-oxo-1-[3-(trifluoromethyl)-phenyl]-1,2,3,4-tetrahydropyrimidine-5-carboxylate (150 mg, 0.256 mmol; Example 19A) was initially charged in dioxane (3.5 ml). Methylhydrazine (35.4 mg, 0.767 mmol) was added dropwise to the reaction mixture, and the mixture was then stirred at boiling point for 3 h. The reaction mixture was then separated directly by preparative HPLC (Method 12). This gave 55 mg (39% of theory) of the target compound.

HPLC (Method 8): $R_t$=3.95 min; MS (ESIpos): m/z (%)=505.9 (100) [M+H]$^+$ $^1$H-NMR (400 MHz, $d_6$-DMSO): δ=2.52 (s, 3H), 3.23-3.29 (d, 1H), 3.55 (s, 3H), 3.55-3.62 (d, 1H), 6.53 (s, 1H), 7.70-7.95 (m, 5H), 8.19 (d, 1H), 8.26 (d, 1H), 8.31 (s, 1H), 8.93 (s, 1H).

Example 3

4-{(4S)-7-Methyl-2,5-dioxo-1-[3-(trifluoromethyl) phenyl]-1,2,3,4,5,6,7,8-octahydropyrimido-[4,5-d] pyridazin-4-yl}-3-(methylsulphonyl)benzonitrile

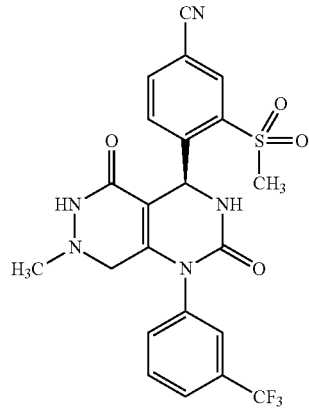 [SMILES: CN1CC2=C(C(=O)N1)[C@@H](c1ccc(C#N)cc1S(C)(=O)=O)NC(=O)N2c1cccc(C(F)(F)F)c1]

(rac)-4-{7-Methyl-2,5-dioxo-1-[3-(trifluoromethyl)phenyl]-1,2,3,4,5,6,7,8-octahydropyrimido [4,5-d]pyridazin-4-yl}-3-(methylsulphonyl)benzonitrile (Example 2; 55 mg) was separated into the enantiomers by HPLC chromatography on a chiral phase [sample preparation: sample dissolved in THF/ethyl acetate 1:10 (22 ml); injection volume: 11 ml; column: chiral silica gel phase based on the selector poly(N-methacryloyl-L-leucine-d-menthylamide), 450 mm×30 mm; mobile phase: ethyl acetate; flow rate: 50 ml/min; temperature: 25° C.; UV detection: 260 nm]. This gave 16 mg of the 4S-enantiomer in the form of a colourless amorphous solid.

$R_t$=7.84 min; ee=99.0% [column: chiral silica gel phase based on the selector poly(N-meth-acryloyl-L-leucine-D-menthylamide), 250 mm×4.6 mm; mobile phase: ethyl acetate; flow rate: 2 ml/min; temperature: 25° C.; UV detection: 265 nm]

HPLC (Method 9): $R_t$=3.86 min; MS (DCI/NH$_3$): m/z=506.1 [M+H]$^+$ $^1$H-NMR (400 MHz, $d_6$-DMSO): δ=2.52 (s, 3H), 3.22-3.29 (d, 1H), 3.55 (s, 3H), 3.56-3.62 (d, 1H), 6.53 (s, 1H), 7.68-7.97 (m, 5H), 8.19 (d, 1H), 8.26 (d, 1H), 8.31 (s, 1H), 8.93 (s, 1H).

Example 4

(rac)-4-[7-Methyl-2,5-dioxo-1-[3-(trifluoromethyl) phenyl]-1,2,3,4,5,6,7,8-octahydropyrimido-[4,5-d] pyridazin-4-yl]-3-(trifluoromethyl)benzonitrile

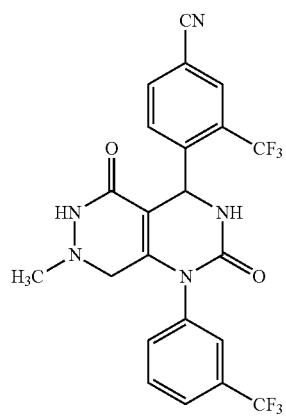 [SMILES: CN1CC2=C(C(=O)N1)C(c1ccc(C#N)cc1C(F)(F)F)NC(=O)N2c1cccc(C(F)(F)F)c1]

Under an atmosphere of argon protective gas, ethyl 6-(bromomethyl)-4-[4-cyano-2-(trifluoro-methyl)phenyl]-2-oxo-1-[3-(trifluoromethyl)phenyl]-1,2,3,4-tetrahydropyrimidine-5-carboxylate (576 mg, 1 mmol; Example 21A) was initially charged in dioxane (20 ml). Methylhydrazine (128 mg, 3 mmol) was added dropwise to the reaction mixture, and the mixture was then stirred at boiling point for 8 h (bath temperature 120° C.). The reaction mixture was then concentrated, and the residue was purified by preparative HPLC (column: Gromsil C18 10 µm; mobile phase: acetonitrile/water+0.1% TFA 10:90→90:10). This gave the target compound as a solid which was reprecipitated from acetonitrile/water (Yield: 205 mg, 41% of theory).

LC-MS (Method 4): $R_t$=2.87 min; MS (ESIpos): m/z (%)=496.2 (100) [M+H]$^+$; MS (ESIneg): m/z (%)=451.2 (100), 494 (20) [M−H]$^−$.

$^1$H-NMR (400 MHz, $d_6$-DMSO): δ=2.55 (s, 3H), 3.25 (d, 1H), 3.55 (d, 1H), 5.70 (s, 1H), 7.70-7.80 (m, 3H), 7.90 (s, 1H), 8.10-8.30 (m, 4H), 8.75 (s, 1H).

Example 5

4-{(4R)-7-Methyl-2,5-dioxo-1-[3-(trifluoromethyl)phenyl]-1,2,3,4,5,6,7,8-octahydropyrimido-[4,5-d]pyridazin-4-yl}-3-(trifluoromethyl)benzonitrile

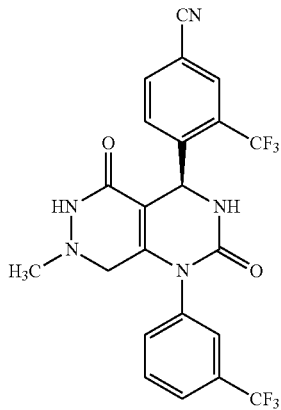 [SMILES: CN1CC2=C(C(=O)N1)[C@@H](c1ccc(C#N)cc1C(F)(F)F)NC(=O)N2c1cccc(C(F)(F)F)c1]

4-{(rac)-7-Methyl-2,5-dioxo-1-[3-(trifluoromethyl)phenyl]-1,2,3,4,5,6,7,8-octahydropyrimido [4,5-d]pyridazin-4-yl}-3-(trifluoromethyl)benzonitrile (Example 4; 180 mg) was separated into the enantiomers by HPLC chromatography on a chiral phase [column: Daicel Chiralpak IA, 5 µm, 250 mm×20 mm; sample preparation: sample dissolved in methanol/MTBE 1:1 (20 ml); injection volume: 1 ml; mobile phase: MTBE/methanol 95:5; flow rate: 15 ml/min; temperature: 30° C.; UV detection: 220 nm]. This gave 75 mg (83% of theory) of the 4R-enantiomer in the form of a solid. The enantiomeric excess (ee value) was determined chromatographically [column: Daicel Chiral-pak IA, 5 µm, 250 mm×4.6 mm; mobile phase: methanol/MTBE 1:9; flow rate: 1 ml/min; temperature: 25° C.; UV detection: 220 nm; $R_t$=6.17 min; ee=99.5%].

LC-MS (Method 3): $R_t$=3.06 min; MS (ESIpos): m/z (%)=496.2 (100) [M+H]$^+$; MS (ESIneg): m/z (%)=451.1 (100), 494 (20) [M−H]$^−$.

Example 6

4-{(4R)-2,5-Dioxo-7-phenyl-1-[3-(trifluoromethyl)phenyl]-1,2,3,4,5,6,7,8-octahydropyrimido-[4,5-d]pyridazin-4-yl}benzonitrile

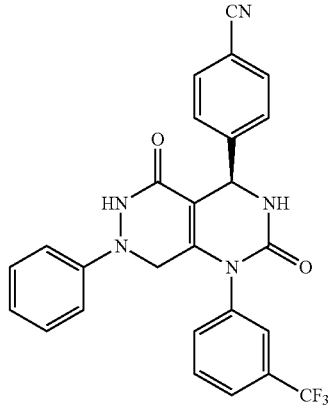 [SMILES: N#Cc1ccc([C@H]2NC(=O)N(c3cccc(C(F)(F)F)c3)C3=C2C(=O)NN(c2ccccc2)C3)cc1]

80 mg (0.16 mmol) of ethyl (4R)-6-(bromomethyl)-4-(4-cyanophenyl)-2-oxo-1-[3-(tri-fluoromethyl)phenyl]-1,2,3,4-tetrahydropyrimidine-5-carboxylate (Example 6A) were dissolved in 2 ml of dioxane, 51 mg (0.47 mmol) of phenylhydrazine were added and the mixture was stirred at 120° C. for 3 hours. The reaction mixture was then concentrated, and the residue that remained was purified by preparative HPLC (Method 10). The product fractions were combined and concentrated, and the solid that remained was dried under reduced pressure (Yield: 24.0 mg, 31% of theory).

HPLC (Method 8): $R_t$=4.31 min; MS (ESIpos): m/z (%)=490 (100) [M+H]$^+$ $^1$H-NMR (400 MHz, $d_6$-DMSO): δ=3.92-4.02 (d, 1H), 4.22-4.33 (d, 1H), 5.40-5.45 (d, 1H), 6.61-6.70 (d, 2H), 6.70-6.91 (t, 1H), 7.12-7.19 (t, 2H), 7.21-7.27 (d, 2H), 7.43-7.57 (m, 1H), 7.57-7.64 (br. s, 1H), 7.64-7.70 (d, 2H), 7.72-7.80 (t, 1H), 7.85-7.90 (d, 1H), 8.27-8.34 (d, 1H), 9.79 (s, 1H).

Example 7

4-{2,5-Dioxo-7-phenyl-1-[3-(trifluoromethyl)phenyl]-1,2,3,4,5,6,7,8-octahydropyrimido[4,5-d]-pyridazin-4-yl}-3-(methylsulphonyl)benzonitrile

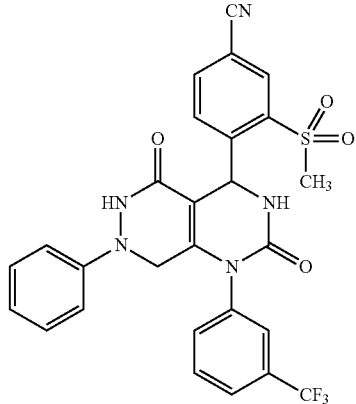 [SMILES: CS(=O)(=O)c1cc(C#N)ccc1C1NC(=O)N(c2cccc(C(F)(F)F)c2)C2=C1C(=O)NN(c1ccccc1)C2]

Ethyl 6-(bromomethyl)-4-[4-cyano-2-(methylsulphonyl)phenyl]-2-oxo-1-[3-(trifluoromethyl)-phenyl]-1,2,3,4-tetrahydropyrimidine-5-carboxylate (150 mg, 0.256 mmol; Example 19A) was initially charged in dioxane (3.5 ml).

Phenylhydrazine (83.0 mg, 0.767 mmol) was added dropwise to the reaction mixture, and the mixture was then stirred at boiling point for 3 h. The reaction mixture was then separated directly by preparative HPLC (Method 12). This gave 9 mg (6% of theory) of the target compound.

HPLC (Method 8): $R_t$=4.38 min; MS (ESIpos): m/z (%)=568.0 (100) [M+H]$^+$; MS (ESIneg): m/z (%)=566.0 (100) [M−H]$^-$ $^1$H-NMR (400 MHz, d$_6$-DMSO): δ=3.54 (s, 3H), 4.04-4.11 (d, 1H), 4.23-4.30 (d, 1H), 6.45 (s, 1H), 6.75 (d, 2H), 7.05 (t, 1H), 7.21-7.32 (m, 3H), 7.64-7.91 (m, 6H), 8.27 (d, 1H), 9.88 (s, 1H).

Example 8

4-{(4R)-7-(2-Fluorobenzyl)-2,5-dioxo-1-[3-(trifluoromethyl)phenyl]-1,2,3,4,5,6,7,8-octahydro-pyrimido[4,5-d]pyridazin-4-yl}benzonitrile

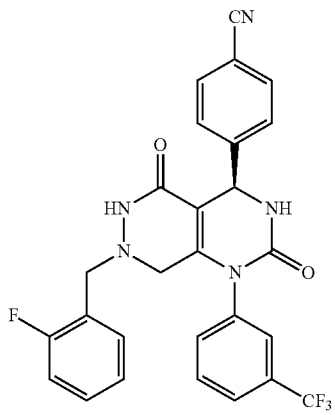 [SMILES: N#Cc1ccc([C@H]2NC(=O)N(c3cccc(C(F)(F)F)c3)C3=C2C(=O)NN(Cc2ccccc2F)C3)cc1]

150 mg (0.30 mmol) of ethyl (4R)-6-(bromomethyl)-4-(4-cyanophenyl)-2-oxo-1-[3-(trifluoromethyl)phenyl]-1,2,3,4-tetrahydropyrimidine-5-carboxylate (Example 6A) were dissolved in 3.5 ml of dioxane. 124 mg (0.89 mmol) of o-fluorobenzylhydrazine were added, and the mixture was stirred at 120° C. overnight. The reaction mixture was then concentrated, and the residue that remained was purified by preparative HPLC (Method 10). The product fractions were combined and concentrated, and the solid that remained was dried under reduced pressure (Yield: 35.0 mg, 22.7% of theory).

LC-MS (Method 4): $R_t$=3.23 min; MS (ESIpos): m/z (%)=522.2 (100) [M+H]$^+$; MS (ESIneg): m/z (%)=520.2 (100) [M−H]$^-$.

$^1$H-NMR (400 MHz, d$_6$-DMSO): δ=2.93-3.07 (d, 1H), 3.49-3.62 (d, 1H), 3.71-3.85 (m, 2H), 5.44 (s, 1H), 7.00-7.10 (t, 2H), 7.13-7.22 (m, 1H), 7.23-7.33 (m, 1H), 7.59-7.67 (m, 2H), 7.68-7.76 (m, 3H), 7.80 (br. s, 1H), 7.86-7.95 (d, 2H), 8.28-8.35 (d, 1H), 9.09 (s, 1H).

Analogously to the procedure for Example 8, the starting material prepared in Example 6A and the appropriate commercially available hydrazine derivative were used to prepare the compounds in the table below:

| Example | Structure | Yield | Analytical data |
|---|---|---|---|
| 9 | (structure shown) | 51% of theory | HPLC (Methody 8): $R_t$ = 3.66 min; MS (ESIpos): m/z = 527 [M + H]$^+$. |

-continued

| Example | Structure | Yield | Analytical data |
|---|---|---|---|
| 10 | 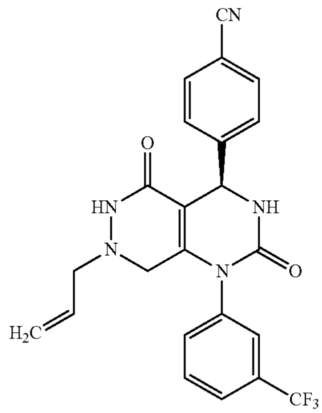 [SMILES: C=CCN1CC2=C(C(=O)N1)[C@@H](c1ccc(C#N)cc1)NC(=O)N2c1cccc(C(F)(F)F)c1] | 8% of theory | LC-MS (Method 4): $R_t$ = 2.94 min; MS (ESIpos): m/z = 454 [M + H]$^+$. |
| 11 | 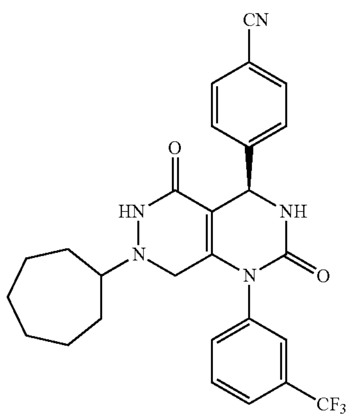 [SMILES: N#Cc1ccc([C@H]2NC(=O)N(c3cccc(C(F)(F)F)c3)C3=C2C(=O)NN(C2CCCCCC2)C3)cc1] | 11% of theory | LC-MS (Method 4): $R_t$ = 3.39 min; MS (ESIpos): m/z = 510 [M + H]$^+$. |
| 12 | 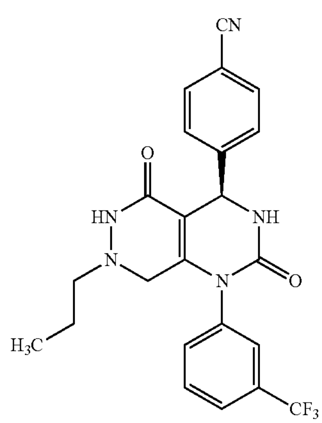 [SMILES: CCCN1CC2=C(C(=O)N1)[C@@H](c1ccc(C#N)cc1)NC(=O)N2c1cccc(C(F)(F)F)c1] | 22% of theory | LC-MS (Method 2): $R_t$ = 2.18 min; MS (ESIpos): m/z = 456 [M + H]$^+$. |

-continued

| Example | Structure | Yield | Analytical data |
|---|---|---|---|
| 13 | 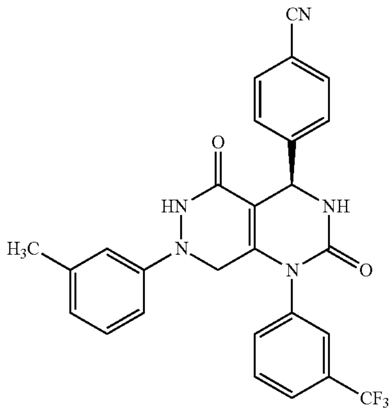 [SMILES: Cc1cccc(N2CC3=C(C(=O)N2)[C@@H](c2ccc(C#N)cc2)NC(=O)N3c2cccc(C(F)(F)F)c2)c1] | 5% of theory | LC-MS (Method 3): $R_t$ = 3.45 min; MS (ESIpos): m/z = 504 [M + H]$^+$. |
| 14 | 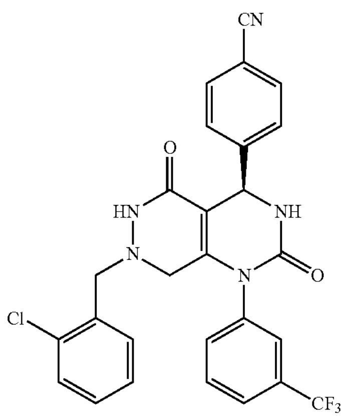 [SMILES: N#Cc1ccc([C@H]2NC(=O)N(c3cccc(C(F)(F)F)c3)C3=C2C(=O)NN(Cc2ccccc2Cl)C3)cc1] | 28% of theory | LC-MS (Method 3): $R_t$ = 3.50 min; MS (ESIpos): m/z = 538 [M + H]$^+$. |
| 15 | 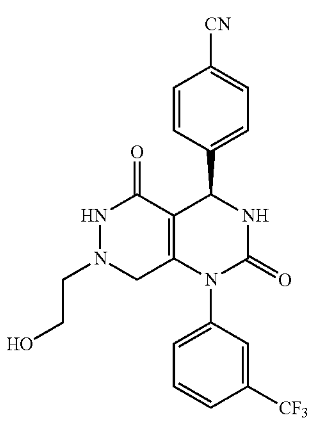 [SMILES: N#Cc1ccc([C@H]2NC(=O)N(c3cccc(C(F)(F)F)c3)C3=C2C(=O)NN(CCO)C3)cc1] | 32% of theory | HPLC (Method 9): $R_t$ = 3.63 min; MS (ESIpos): m/z = 458 [M + H]$^+$. |

-continued

| Example | Structure | Yield | Analytical data |
|---|---|---|---|
| 16 | 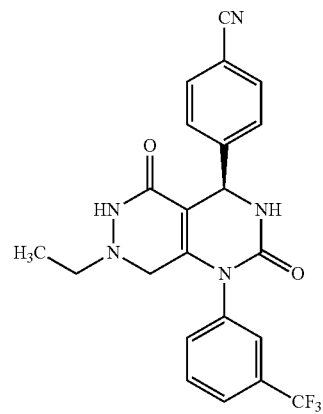 | 14% of theory | HPLC (Method 9): R_t = 3.72 min; MS (DCI/NH_3): m/z = 536.1 [M + H]+. 1H-NMR (400 MHz, d_6-DMSO): δ = 2.75-2.92 (m, 2H), 3.67 (t, 2H), 3.41-3.49 (d, 1H), 3.55 (s, 3H), 3.63-3.70 (d, 1H), 3.97 (t, 1H), 6.52 (s, 1H), 7.67-7.93 (m, 5H), 8.14-8.33 (m, 3H), 8.99 (s, 1H). |

Example 17

4-{(4R)-7-Ethyl-2,5-dioxo-1-[3-(trifluoromethyl)phenyl]-1,2,3,4,5,6,7,8-octahydropyrimido[4,5-d]-pyridazin-4-yl}benzonitrile

Example 18

4-[4-Cyano-2-(methylsulphonyl)phenyl]-7-ethyl-2,5-dioxo-1-[3-(trifluoromethyl)phenyl]-1,2,3,4,5,6,7,8-octahydropyrimido[4,5-d]pyridazin-7-ium trifluoroacetate

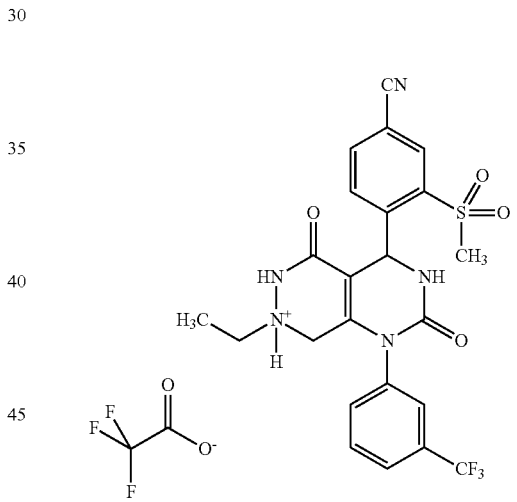

200 mg (0.393 mmol) of ethyl (4R)-6-(bromomethyl)-4-(4-cyanophenyl)-2-oxo-1-[3-(trifluoromethyl)phenyl]-1,2,3,4-tetrahydropyrimidine-5-carboxylate (Example 6A) were dissolved in 1 ml of dioxane, 71 mg (0.472 mmol) of ethylhydrazine oxalate were added and the mixture was stirred at 120° C. for 3 hours. The reaction mixture was then concentrated, and the residue that remained was purified by preparative HPLC (Method 10). The product fractions were combined and concentrated, and the solid that remained was dried under reduced pressure (Yield: 26.0 mg, 15% of theory).

LC-MS (Method 3): R_t=2.97 min; MS (ESIpos): m/z (%)=442.3 (100) [M+H]+.

1H-NMR (400 MHz, d_6-DMSO): δ=9.03 (s, 1H), 8.28 (d, 1H), 7.87 (d, 2H), 7.82 (d, 2H), 7.72 (t, 1H), 7.69 (s, 1H), 7.65 (d, 2H), 5.42 (br. s, 1H), 3.67 (d, 1H), 3.14 (d, 1H), 2.61 (q, 2H), 0.77 (t, 3H).

Ethyl 6-(bromomethyl)-4-[4-cyano-2-(methylsulphonyl)phenyl]-2-oxo-1-[3-(trifluoromethyl)-phenyl]-1,2,3,4-tetrahydropyrimidine-5-carboxylate (150 mg, 0.256 mmol; Example 19A) was initially charged in dioxane (3.5 ml). Ethylhydrazine oxalate (115 mg, 0.767 mmol) was added to the reaction mixture, and the mixture was then stirred at boiling point for 3 h. The reaction mixture was then separated directly by two preparative HPLCs (initially according to Method 12, then according to Method 15). This gave 18 mg (14% of theory) of the target compound.

HPLC (Method 9): R_t=4.04 min; MS (DCI/NH_3): m/z (%)=520.1 (100) [M+H]+.

1H-NMR (400 MHz, d_6-DMSO): δ=0.85 (t, 3H), 2.77 (q, 2H), 3.26-3.34 (d, 1H), 3.55 (s, 3H), 3.57-3.64 (d, 1H), 6.52 (s, 1H), 6.70-7.99 (m, 5H), 8.17 (d, 1H), 8.26 (d, 1H), 8.31 (s, 1H), 9.08 (s, 1H).

Example 19

4-(4R)-2,5-Dioxo-7-[4-(trifluoromethyl)benzyl]-1-[3-(trifluoromethyl)phenyl]-1,2,3,4,5,6,7,8-octahydropyrimido[4,5-d]pyridazin-4-ylbenzonitrile

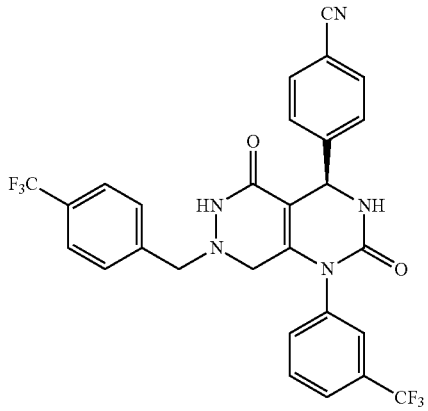 [SMILES: N#Cc1ccc([C@H]2NC(=O)N(c3cccc(C(F)(F)F)c3)C3=C2C(=O)NN(Cc2ccc(C(F)(F)F)cc2)C3)cc1]

150 mg (0.295 mmol) of ethyl (4R)-6-(bromomethyl)-4-(4-cyanophenyl)-2-oxo-1-[3-(trifluoromethyl)phenyl]-1,2,3,4-tetrahydropyrimidine-5-carboxylate (Example 6A) were dissolved in 3 ml of dioxane, 168 mg (0.885 mmol) of [4-(trifluoromethyl)benzyl]hydrazine were added and the mixture was stirred at 120° C. overnight. The reaction mixture was then concentrated, and the residue that remained was purified by preparative HPLC (Method 10). The product-containing fractions were combined and concentrated. The residue was purified again by another preparative HPLC (Method 13). Concentration of the product fractions gave 38 mg (23% of theory) of the target compound.

LC-MS (Method 2): $R_t$=2.59 min; MS (ESIpos): m/z (%)=572.1 (100) [M+H]$^+$.

$^1$H-NMR (400 MHz, $d_6$-DMSO): δ=9.08 (s, 1H), 8.32 (d, 1H), 7.92 (d, 2H), 7.84 (s, 1H), 7.75 (d, 2H), 7.71 (d, 1H), 7.63-7.57 (m, 4H), 7.37 (d, 2H), 5.45 (d, 1H), 3.83 (dd, 2H), 3.53 (d, 1H), 2.97 (d, 1H).

Example 20

4-(4R)-7-(Cyclopropylmethyl)-2,5-dioxo-1-[3-(trifluoromethyl)phenyl]-1,2,3,4,5,6,7,8-octahydro-pyrimido[4,5-d]pyridazin-4-ylbenzonitrile

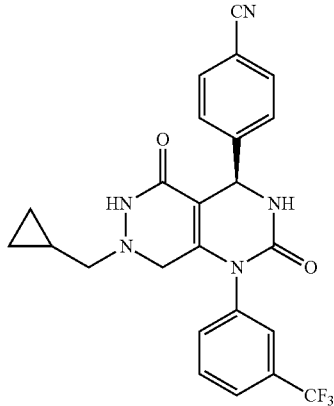 [SMILES: N#Cc1ccc([C@H]2NC(=O)N(c3cccc(C(F)(F)F)c3)C3=C2C(=O)NN(CC2CC2)C3)cc1]

150 mg (0.295 mmol) of ethyl (4R)-6-(bromomethyl)-4-(4-cyanophenyl)-2-oxo-1-[3-(trifluoromethyl)phenyl]-1,2,3,4-tetrahydropyrimidine-5-carboxylate (Example 6A) were dissolved in 2 ml of dioxane, 254 mg (2.951 mmol) of (cyclopropylmethyl)hydrazine were added and the mixture was stirred at 120° C. overnight. The reaction mixture was then concentrated, and the residue that remained was purified by preparative HPLC (Method 10). The product-containing fractions were combined and concentrated. The residue was purified again by another preparative HPLC (Method 14). Concentration of the product fractions gave 5 mg (4% of theory) of the target compound.

$^1$H-NMR (400 MHz, $d_6$-DMSO): δ=8.94 (s, 1H), 8.27 (d, 1H), 7.86 (br. d, 3H), 7.81-7.80 (m, 1H), 7.73-7.70 (m, 2H), 7.64 (d, 2H), 5.42 (s, 1H), 3.74 (d, 1H), 3.29 (d, 1H), 2.46 (dd, 1H), 2.34 (dd, 1H), 0.51 (m, 1H), 0.25 (m, 1H), 0.16 (m, 1H), −0.12 (m, 1H), −0.19 (m, 1H).

Example 21

Ethyl [(4R)-4-(4-cyanophenyl)-2,5-dioxo-1-[3-(trifluoromethyl)phenyl]-2,3,4,5,6,8-hexahydro-pyrimido[4,5-d]pyridazin-7(1H)-yl]acetate

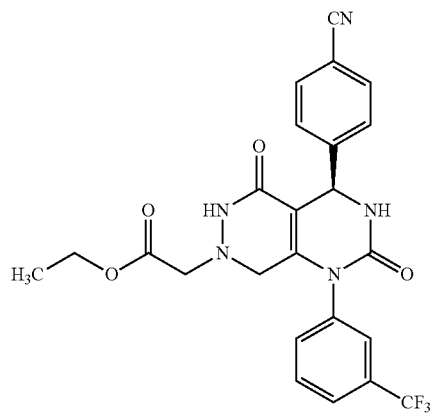 [SMILES: CCOC(=O)CN1CC2=C(C(=O)N1)[C@@H](c1ccc(C#N)cc1)NC(=O)N2c1cccc(C(F)(F)F)c1]

300 mg (0.59 mmol) of ethyl (4R)-6-(bromomethyl)-4-(4-cyanophenyl)-2-oxo-1-[3-(trifluoromethyl)phenyl]-1,2,3,4-tetrahydropyrimidine-5-carboxylate (Example 6A) were dissolved in 5 ml of dioxane. 456 mg (2.95 mmol) of ethyl hydrazinoacetate hydrochloride, which, dissolved in methanol, had been passed beforehand through StratoSphere cartridges (PL-HCO$_3$ MP SPE, from Polymere Laboratories), were added. The mixture was then stirred under reflux overnight. The reaction mixture was then concentrated, and the residue that remained was purified by preparative HPLC (Method 10). The product fractions were combined and concentrated, and the solid that remained was dried under reduced pressure (Yield: 45.0 mg, 15% of theory).

LC-MS (Method 5): $R_t$=1.05 min; MS (ESIpos): m/z (%)=500.2 (100) [M+H]$^+$; MS (ESIneg): m/z (%)=498.3 (100) [M−H]$^-$.

$^1$H-NMR (400 MHz, $d_6$-DMSO): δ=1.05-1.13 (t, 3H), 3.36-3.41 (d, 1H), 3.42-3.47 (s, 1H), 3.55-3.63 (d, 1H), 3.67-3.77 (d, 1H), 3.91-4.05 (m, 2H), 5.42 (s, 1H), 7.62-7.74 (m, 4H), 7.78-7.85 (m, 2H), 7.86-7.92 (d, 2H), 8.27-8.33 (d, 1H), 8.97 (s, 1H).

Analogously to the procedure for Example 21, the starting material prepared in Example 6A and the appropriate hydrazine hydrochloride were used to prepare the compound in the table below:

| Example | Structure | Yield | Analytical data |
|---|---|---|---|
| 22 | 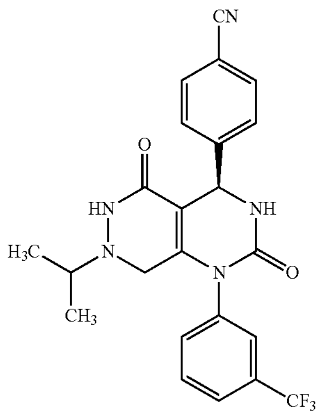 [SMILES: CC(C)N1CC2=C(C(=O)N1)[C@@H](c1ccc(C#N)cc1)NC(=O)N2c1cccc(C(F)(F)F)c1] | 15% of theory | LC-MS (Method 7): $R_t$ = 1.67 min; MS (ESIpos): m/z = 456 [M + H]$^+$. |

Example 23

2-[(4R)-4-(4-Cyanophenyl)-7-methyl-2,5-dioxo-1-[3-(trifluoromethyl)phenyl]-1,4,5,6,7,8-hexa-hydro-pyrimido[4,5-d]pyridazin-3(2H)-yl]-N,N-dimethylacetamide

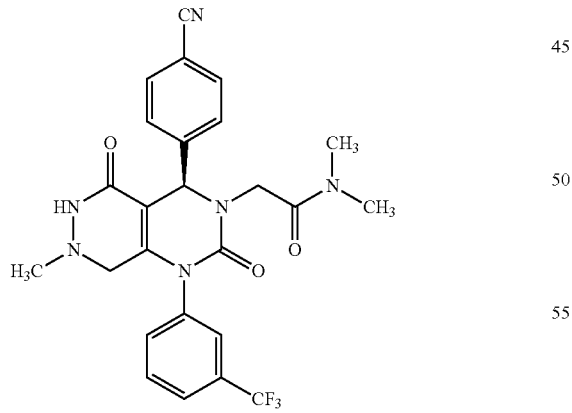

100 mg (0.169 mmol) of the compound from Example 13A were dissolved in 2 ml of dioxane, and 23 mg (0.506 mmol) of methylhydrazine were added. The mixture was stirred at 120° C. for two hours and then concentrated. The residue was taken up in DMSO and purified by preparative HPLC (Method 10). This gave 53 mg (61% of theory) of the target compound.

HPLC (Method 8): $R_t$=3.98 min; MS (ESIpos): m/z (%)=513.2 (100) [M+H]$^+$ $^1$H-NMR (400 MHz, d$_6$-DMSO): δ=2.34 (s, 3H), 2.81 (s, 3H), 2.85 (s, 3H), 3.06 (d, 1H), 3.52 (d, 1H), 3.77 (d, 1H), 4.50 (d, 1H), 5.53 (s, 1H), 7.87 (d, 1H), 7.71 (d, 1H), 7.73 (d, 2H), 7.82 (d, 2H), 7.88 (d, 2H), 8.87 (s, 1H).

Analogously to the procedure for Example 23, the starting materials stated and the appropriate hydrazine derivative are used to prepare the compounds in the table below:

| Example | Structure | Starting material | Yield | Analytical data |
|---|---|---|---|---|
| 24 | 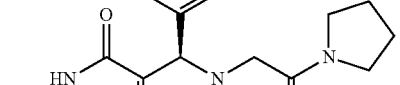 | 14A | 53% of theory | LC-MS (Method 3): $R_t$ = 3.10 min; MS (ESIpos): m/z = 539 [M + H]$^+$. |
| 25 | 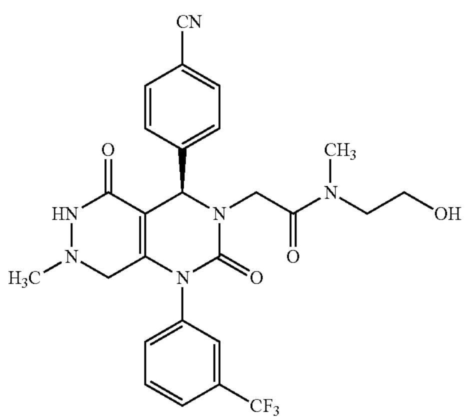 [SMILES: CN1CC2=C(C(=O)N1)[C@@H](c1ccc(C#N)cc1)N(CC(=O)N(C)CCO)C(=O)N2c1cccc(C(F)(F)F)c1] | 15A | 53% of theory | LC-MS (Method 4): $R_t$ = 2.50 min; MS (ESIpos): m/z = 543 [M + H]$^+$. |
| 26 | 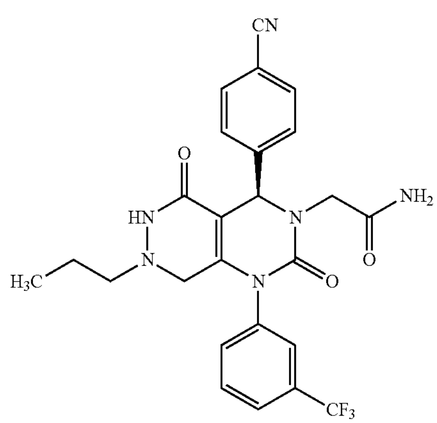 [SMILES: CCCN1CC2=C(C(=O)N1)[C@@H](c1ccc(C#N)cc1)N(CC(N)=O)C(=O)N2c1cccc(C(F)(F)F)c1] | 12A | 11% of theory | LC-MS (Method 2): $R_t$ = 2.11 min; MS (ESIpos): m/z = 513 [M + H]$^+$. |

Example 27

2-[(4R)-4-(4-Cyanophenyl)-7-(2-hydroxyethyl)-2,5-dioxo-1-[3-(trifluoromethyl)phenyl]-1,4,5,6,7,8-hexahydropyrimido [4,5-d]pyridazin-3(2H)-yl]acetamide

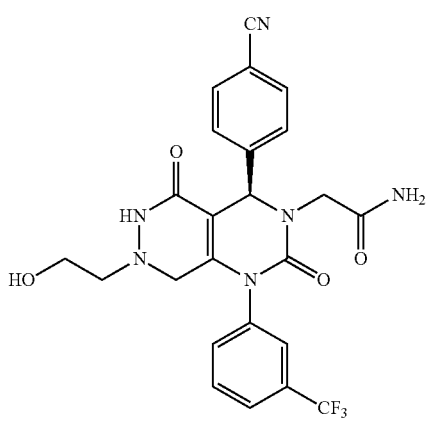 [SMILES: N#Cc1ccc([C@@H]2C3=C(CN(CCO)NC3=O)N(c3cccc(C(F)(F)F)c3)C(=O)N2CC(N)=O)cc1]

200 mg (0.393 mmol) of the compound from Example 12A were dissolved in 2 ml of dioxane, 32 mg (0.425 mmol) of 2-hydrazinoethanol were added and the mixture was stirred at 120° C. for 4 hours. The reaction mixture was then concentrated, and the residue was taken up in a mixture of water and methylene chloride. The organic phase was separated off, dried over sodium sulphate, filtered and concentrated almost to dryness. A small amount of silica gel was added to this residue, and the remaining solvent was then removed under reduced pressure. This crude product was then purified by two chromatographies on silica gel (mobile phase in each case dichloromethane/methanol 10:1). This gave 13 mg (7% of theory) of the target compound.

LC-MS (Method 2): $R_t$=1.71 min; MS (ESIpos): m/z (%)=515.0 (100) [M+H]$^+$; MS (ESIneg): m/z (%)=513.2 (100) [M−H]$^−$.

$^1$H-NMR (400 MHz, $d_6$-DMSO): δ=8.93 (s, 1H), 7.89 (d, 2H), 7.82 (d, 2H), 7.74-7.69 (m, 4H), 7.40 (s, 1H), 7.15 (s, 1H), 5.54 (s, 1H), 4.43 (t, 1H), 4.17 (d, 1H), 3.76 (d, 1H), 3.30-3.21 (m, 4H), 2.71-2.57 (m, 2H).

Example 28

Methyl [(4R)-4-(4-cyanophenyl)-7-methyl-2,5-dioxo-1-[3-(trifluoromethyl)phenyl]-1,4,5,6,7,8-hexahydropyrimido[4,5-d]pyridazin-3(2H)-yl]acetate

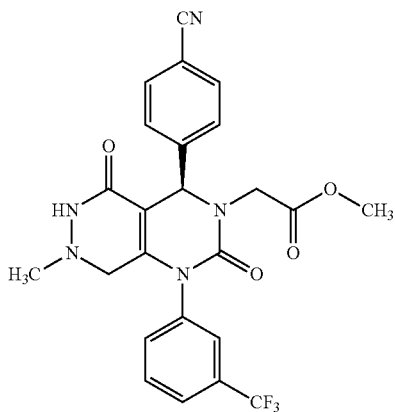

65 mg (0.112 mmol) of the compound from Example 17A were dissolved in 2 ml of dioxane, and 16 mg (0.336 mmol) of methylhydrazine were added. The mixture was stirred at 120° C. overnight and then concentrated. The residue was taken up in DMSO and purified by preparative HPLC (Method 10). This gave 40 mg (72% of theory) of the target compound.

LC-MS (Method 4): $R_t$=2.96 min; MS (ESIpos): m/z (%)=500.3 (100) [M+H]$^+$; MS (ESIneg): m/z (%)=498.3 (100) [M−H]$^−$.

$^1$H-NMR (400 MHz, $d_6$-DMSO): δ=8.90 (s, 1H), 7.88 (br. d, 3H), 7.85-7.82 (m, 1H), 7.76-7.72 (m, 4H), 5.66 (s, 1H), 4.19 (d, 1H), 3.82 (d, 1H), 3.78 (d, 1H), 3.55 (s, 3H), 3.08 (d, 1H), 2.36 (s, 3H).

Example 29

4-{(4R)-7-(3-Methylbutyl)-2,5-dioxo-1-[3-(trifluoromethyl)phenyl]-1,2,3,4,5,6,7,8-octahydro-pyrimido[4,5-d]pyridazin-4-yl}benzonitrile

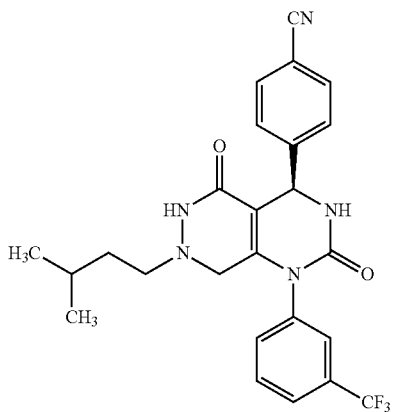 [SMILES: CC(C)CCN1CC2=C(C(=O)N1)[C@@H](c1ccc(C#N)cc1)NC(=O)N2c1cccc(C(F)(F)F)c1]

150 mg (0.295 mmol) of the compound from Example 6A were dissolved in 3 ml of dioxane, and 91 mg (0.885 mmol)

of (3-methylbutyl)hydrazine were added. The mixture was stirred at 120° C. for 3 h and then concentrated. The residue was taken up in DMSO and purified by preparative HPLC (Method 10). This gave 43 mg (29% of theory) of the target compound.

LC-MS (Method 4): $R_t$=3.31 min; MS (ESIpos): m/z (%)=484 (100) [M+H]$^+$.

$^1$H-NMR (400 MHz, $d_6$-DMSO): δ=9.00 (s, 1H), 8.29 (d, 1H), 7.88-7.64 (m, 8H), 5.45 (d, 1H), 3.70 (d, 1H), 3.07 (d, 1H), 2.57-2.45 (m, 2H), 1.38 (m, 1H), 1.03 (m, 2H), 0.71 (d, 3H), 0.66 (d, 3H).

Example 30

(rac)-4-{1-[4-Fluoro-3-(trifluoromethyl)phenyl]-7-methyl-2,5-dioxo-1,2,3,4,5,6,7,8-octahydro-pyrimido[4,5-d]pyridazin-4-yl}benzonitrile

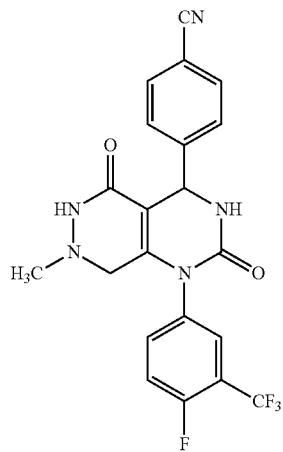 [SMILES: CN1CC2=C(C(=O)N1)C(c1ccc(C#N)cc1)NC(=O)N2c1ccc(F)c(C(F)(F)F)c1]

527 mg (1.0 mmol) of ethyl 4-(4-cyanophenyl)-1-[4-fluoro-3-(trifluoromethyl)phenyl]-6-(bromomethyl)-2-oxo-1,2,3,4-tetrahydropyrimidine-5-carboxylate were dissolved in 25 ml of dioxane, and 138 mg (3.0 mmol; 3 eq.) of methylhydrazine were added. The mixture was stirred at 120° C. for 1 h and then concentrated. The residue was purified directly by preparative HPLC (column: Gromsil C-18 10 μm; mobile phase: acetonitrile/water+0.1% TFA 10:90→90:10). This gave 270 mg (55% of theory) of the target compound.

LC-MS (Method 3): $R_t$=2.91 min; MS (ESIpos): m/z (%)=446.1 (100) [M+H]$^+$; MS (ESIneg): m/z (%)=401.0 (100), 444.2 (50) [M−H]$^-$.

$^1$H-NMR (400 MHz, $d_6$-DMSO): δ=2.37 (s, 3H), 3.14-3.18 (d, 1H), 3.65-3.70 (d, 1H), 5.43 (s, 1H), 7.60-7.90 (m, 7H), 8.30 (d, 1H), 8.84 (s, 1H).

Example 31

(4R)-4-{1-[4-Fluoro-3-(trifluoromethyl)phenyl]-7-methyl-2,5-dioxo-1,2,3,4,5,6,7,8-octahydro-pyrimido[4,5-d]pyridazin-4-yl}benzonitrile

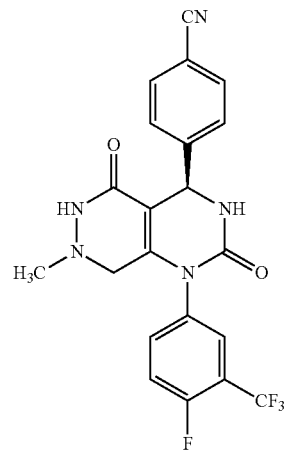 [SMILES: CN1CC2=C(C(=O)N1)[C@@H](c1ccc(C#N)cc1)NC(=O)N2c1ccc(F)c(C(F)(F)F)c1]

(rac)-4-{1-[4-Fluoro-3-(trifluoromethyl)phenyl]-7-methyl-2,5-dioxo-1,2,3,4,5,6,7,8-octahydropyrimido[4,5-d]pyridazin-4-yl}benzonitrile (250 mg) was separated into the enantiomers by HPLC chromatography on a chiral phase [sample preparation: sample dissolved in THF/ethyl acetate 2:5 (14 ml); injection volume: 14 ml; column: chiral silica gel phase based on the selector poly(N-methacryloyl-L-leucine-dicyclopropylmethylamide), 250 mm×20 mm; mobile phase: ethyl acetate; flow rate: 50 ml/min; temperature: 24° C.; UV detection: 260 nm]. 118 mg of the 4R enantiomer were obtained in the form of a colourless amorphous solid as fraction 2 (the 4S enantiomer was obtained as earlier-eluting fraction 1). The 4R enantiomer was then re-purified again by preparative HPLC on a chiral phase (column: Gromsil C-18 10 μm; mobile phase: acetonitrile/water+0.1% TFA 10:90→90:10). This gave 117 mg of the title compound.

$R_t$=4.91 min; ee>99.0% [column: chiral silica gel phase based on the selector poly(N-meth-acryloyl-L-leucine-dicyclopropylmethylamide), 250 mm×4.6 mm; mobile phase: ethyl acetate/methanol 10:1; flow rate: 2 ml/min; temperature: 25° C.; UV detection: 260 nm].

LC-MS (Method 1): $R_t$=1.78 min; MS (ESIpos): m/z (%)=446.2 (100) [M+H]$^+$; MS (ESIneg): m/z (%)=401.2 (100), 444.2 (50) [M−H]$^-$.

$^1$H-NMR (400 MHz, $d_6$-DMSO): δ=2.37 (s, 3H), 3.14-3.18 (d, 1H), 3.65-3.70 (d, 1H), 5.43 (s, 1H), 7.59-7.89 (m, 7H), 8.29 (d, 1H), 8.83 (s, 1H).

B. Assessment of the Pharmacological Activity

The pharmacological effect of the compounds of the invention can be shown in the assays described below:

Abbreviations:
AMC 7-amido-4-methylcoumarin
BNP brain natriuretic peptide

BSA bovine serum albumin
HEPES N-(2-hydroxyethyl)piperazine-N'-2-ethanesulphonic acid
HNE humane neutrophil elastase
IC inhibitory concentration
MeOSuc methoxysuccinyl
NADP nicotinamide adenine dinucleotide phosphate
v/v volume to volume ratio (of a solution)
w/v weight to volume ratio (of a solution)

B-1. In vitro HNE Inhibition Assay

The potency of the compounds of the invention is ascertained in an in vitro inhibition assay. The HNE-mediated amidolytic cleavage of a suitable peptide substrate leads in this connection to an increase in the fluorescent light. The signal intensity of the fluorescent light is directly proportional to the enzyme activity. The effective concentration of a test compound at which half the enzyme is inhibited (50% signal intensity of the fluorescent light) is indicated as $IC_{50}$.

Procedure:

Enzyme (80 pM HNE; from Serva, Heidelberg) and substrate (20 μM MeOSuc-Ala-Ala-Pro-Val-AMC; from Bachem, Weil am Rhein) are incubated in an assay volume of in total 50 μl of assay buffer (0.1 M HEPES pH 7.4, 0.5 M NaCl, 0.1% w/v BSA, 1% v/v DMSO) in a 384-well microtiter plate in the presence and absence of the test substance at 37° C. for 2 hours. The intensity of the fluorescent light from the assay mixtures is measured (Ex. 380 nm, Em. 460 nm). The $IC_{50}$ values are determined by plotting the intensity of the fluorescent light against the active substance concentration.

Representative $IC_{50}$ values for the compounds of the invention are shown in Table A below:

TABLE A

Inhibition of human neutrophil elastase (HNE)

| Exemplary embodiment No. | $IC_{50}$ [nM] |
|---|---|
| 1 | 28 |
| 2 | 3 |
| 4 | 10 |
| 8 | 32 |
| 9 | 23 |
| 17 | 16 |
| 23 | 4 |
| 27 | 11 |
| 31 | 28 |

B-2. Animal Model of Pulmonary Arterial Hypertension

The monocrotaline-induced pulmonary hypertension in rats is a widely used animal model of pulmonary arterial hypertension. The pyrrolizidine alkaloid monocrotaline is metabolized after subcutaneous injection to the toxic monocrotalinepyrrole in the liver and leads within a few days to endothelial damage in the pulmonary circulation, followed by a remodeling of the small pulmonary arteries (media hypertrophy, de novo muscularization). A single subcutaneous injection is sufficient to induce pronounced pulmonary hypertension in rats within 4 weeks [Cowan et al., Nature Med. 6, 698-702 (2000)].

Male Sprague-Dawley rats are used for the model. On day 0, the animals receive a subcutaneous injection of 60 mg/kg monocrotaline. Treatment of the animals begins no earlier than 14 days after the monocrotaline injection and extends over a period of at least 14 days. At the end of the study, the animals undergo hemodynamic investigations, and the arterial and central venous oxygen saturation are determined. For the hemodynamic measurement, the rats are initially anesthetized with pentobarbital (60 mg/kg). The animals are then tracheotomized and artificially ventilated (rate: 60 breaths/min; inspiration to expiration ratio: 50:50; positive end-expiratory pressure: 1 cm $H_2O$; tidal volume: 10 ml/kg of body weight; $FIO_2$: 0.5). The anesthesia is maintained by isoflurane inhalation anesthesia. The systemic blood pressure is determined in the left carotid artery using a Millar microtip catheter. A polyethylene catheter is advanced through the right jugular vein into the right ventricle to determine the right ventricular pressure. The cardiac output is determined by thermodilution. Following the hemodynamics, the heart is removed and the ratio of right to left ventricle including septum is determined. In addition, plasma samples are obtained to determine biomarkers (for example proBNP) and plasma substance levels.

B-3. Animal Model of Acute Lung Failure

Elastase-induced lung failure in mice, rats or hamsters is a widely used animal model of acute lung failure (also: "acute lung injury", "acute respiratory distress syndrome") [Tremblay et al., Chest 121, 582-588 (2002); Kuraki et al., Am. J. Resp. Crit. Care Med. 166, 596-500 (2002)]. The animals are treated 1 hour prior to orotracheal instillation of human neutrophil elastase (HNE). 2 hours after orotracheal HNE instillation, a bronchoalveolar lavage is carried out, and the hemoglobin content and the differential cell picture of the lavage are determined.

B-4. Animal Model of Pulmonary Emphysema

Elastase-induced pulmonary emphysema in mice, rats or hamsters is a widely used animal model of pulmonary emphysema [Sawada et al., Exp. Lung Res. 33, 277-288 (2007)]. The animals receive an orotracheal instillation of porcine pancreas elastase. The treatment of the animals starts at the day of the instillation of the porcine pancreas elastase and extends over a period of 3 weeks. At the end of the study, the pulmonary compliance is determined, and an alveolar morphometry is carried out.

B-5. Determination of Pharmacokinetic Parameters Following Intravenous and Oral Administration The substance to be examined is administered to animals (for example mouse, rat, dog) intravenously as a solution, oral administration is carried out as a solution or suspension via a stomach tube. After the administration of the substance, blood samples are taken from the animals at certain points in time. This blood is heparinized and then used to obtain plasma by centrifu-gation. The substance in the plasma is quantified analytically by LC/MS-MS. The plasma concentration/time curves determined in this manner are used to calculate the pharmacokinetic parameters such as AUC (area under the concentration/time cureve), $C_{max}$ (maximum plasma concentration), $+T_{1/2}$ (half-time) and CL (clearance) using a validated pharmacokinetic calculation program.

B-6. Determination of Plasma Protein Binding

Protein binding of test substances in the plasma of various species is determined by the ultra-filtration method. Here, the substance is pipetted from an acetonitrile stock solution into the plasma usually in a final concentration of 1000 ng/ml, the final concentration of acetonitrile not exceeding 1%. The plasma is filtered through a cellulose membrane (for example Centrifree Micropartition Device, from Amicon-Millipore, Witten) to separate the protein and the substance bound to the protein. The concentration of the unbound substance in the filtrate is determined. Additionally, unspecific binding of the substance (without plasma) to the filtration unit is determined in an analogous manner. This unspecific binding to the filter unit, which should not exceed 20%, is taken into account when calculating protein binding of the substance.

C. Exemplary Embodiments of Pharmaceutical Compositions

The compounds of the invention can be converted into pharmaceutical preparations in the following ways:

Tablet:

Composition:

100 mg of the compound of the invention, 50 mg of lactose (monohydrate), 50 mg of corn starch (native), 10 mg of polyvinylpyrrolidone (PVP 25) (from BASF, Ludwigshafen, Germany) and 2 mg of magnesium stearate.

Tablet weight 212 mg, diameter 8 mm, radius of curvature 12 mm

Production:

The mixture of compound of the invention, lactose and starch is granulated with a 5% strength solution (m/m) of the PVP in water. The granules are mixed with the magnesium stearate for 5 minutes after drying. This mixture is compressed with a conventional tablet press (see above for format of the tablet). A guideline compressive force for the compression is 15 kN.

Suspension which can be Administered Orally:

Composition:

1000 mg of the compound of the invention, 1000 mg of ethanol (96%), 400 mg of Rhodigel® (xanthan gum from FMC, Pennsylvania, USA) and 99 g of water.

10 ml of oral suspension correspond to a single dose of 100 mg of the compound of the invention.

Production:

The Rhodigel is suspended in ethanol, and the compound of the invention is added to the suspension. The water is added while stirring. The mixture is stirred for about 6 h until the swelling of the Rhodigel is complete.

Solution which can be Administered Orally:

Composition:

500 mg of the compound of the invention, 2.5 g of polysorbate and 97 g of polyethylene glycol 400.20 g of oral solution correspond to a single dose of 100 mg of the compound according to the invention.

Production:

The compound of the invention is suspended in the mixture of polyethylene glycol and polysorbate with stirring. The stirring process is continued until the compound according to the invention has completely dissolved.

i.v. Solution:

The compound of the invention is dissolved in a concentration below the saturation solubility in a physiologically tolerated solvent (e.g. isotonic saline solution, 5% glucose solution and/or 30% PEG 400 solution). The solution is sterilized by filtration and used to fill sterile and pyrogen-free injection containers.

The invention claimed is:

1. A compound of the formula (I)

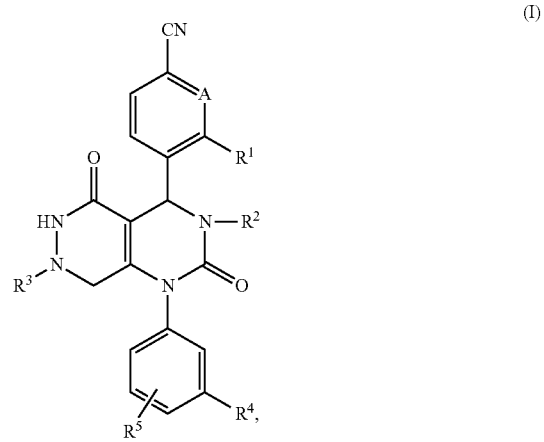

in which

A represents CH or N, $R^1$ represents hydrogen, halogen, cyano, nitro, $(C_1-C_6)$-alkyl, difluoromethyl, trifluoromethyl, $(C_1-C_6)$-alkoxy, difluoromethoxy, trifluoromethoxy, amino, mono- or di-$(C_1-C_6)$-alkylamino or represents a group of the formula —NH—C(=O)—$R^6$, —NH—C(=O)—NH$R^6$, —NH—SO$_2$—$R^7$ or —S(O)$_n$—$R^8$ in which $R^6$ represents hydrogen or $(C_1-C_6)$-alkyl, $R^7$ represents $(C_1-C_6)$-alkyl, $R^8$ represents $(C_1-C_6)$-alkyl which may be substituted by hydroxyl, $(C_1-C_4)$-alkoxy, amino, mono- or di-$(C_1-C_4)$-alkylamino, hydroxycarbonyl, aminocarbonyl, $(C_3-C_6)$-cycloalkyl or phenyl, or represents $(C_2-C_6)$-alkenyl, $(C_3-C_6)$-cycloalkyl or phenyl, where the $(C_3-C_6)$-cycloalkyl groups mentioned may be substituted up to two times by identical or different substituents from the group consisting of $(C_1-C_4)$-alkyl, hydroxyl and $(C_1-C_4)$-alkoxy and the phenyl groups mentioned may be substituted up to two times by identical or different substituents from the group consisting of fluorine, chlorine, cyano, $(C_1-C_4)$-alkyl, difluoromethyl, trifluoromethyl, $(C_1-C_4)$-alkoxy, difluoromethoxy and trifluoro-methoxy, and n represents the number 0, 1 or 2, $R^2$ represents hydrogen, represents $(C_1-C_6)$-alkyl or $(C_1-C_6)$-alkenyl, each of which may be substituted up to three times by fluorine, or represents phenyl, pyridyl or pyrimidinyl, where phenyl, pyridyl and pyrimidinyl for their part may be substituted up to two times by identical or different substituents from the group consisting of fluorine, chlorine, cyano, $(C_1-C_4)$-alkyl, trifluoromethyl, $(C_1-C_4)$-alkoxy and trifluoromethoxy, or $R^2$ represents a group of the formula —C(=O)—O—$R^9$, -$L^1$-C(=O)—O—$R^{10}$, -$L^2$-C(=O)—N$R^{11}R^{12}$, -$L^2$-SO$_2$—N$R^{11}R^{12}$, -$L^2$-C(=O)—N$R^{13}$—N$R^{11}R^{12}$ or -$L^2$-SO$_2$—$R^{14}$ in which $L^1$ represents $(C_1-C_6)$-alkanediyl,
$L^2$ represents a bond or $(C_1-C_6)$-alkanediyl,
$R^9$ represents $(C_1-C_6)$-alkyl,
$R^{10}$ represents hydrogen or $(C_1-C_6)$-alkyl,
$R^{11}$ and $R^{12}$ are identical or different and independently of one another represent hydrogen, $(C_1-C_6)$-alkyl, $(C_3-C_6)$-cycloalkyl or 4- to 6-membered heterocyclyl,
where $(C_1-C_6)$-alkyl, $(C_3-C_6)$-cycloalkyl and 4- to 6-membered heterocyclyl for their part may be substituted up to two times by identical or different substituents from the group consisting of fluorine, hydroxyl, $(C_1-C_4)$-alkoxy, oxo, amino, mono- or di-$(C_1-C_4)$-alkylamino, hydroxycarbonyl, $(C_1-C_4)$-alkoxycarbonyl and aminocarbonyl and where in $(C_1-C_6)$-alkyl a $CH_2$ group may be exchanged for an oxygen atom if this results in a chemically stable compound,
or
$R^{11}$ and $R^{12}$ together with the nitrogen atom to which they are attached form a 4- to 6-membered heterocycle which may contain a further ring heteroatom from the group consisting of N, O, S, SO and $SO_2$ and which may be substituted up to two times by identical or different substituents from the group consisting of $(C_1-C_4)$-alkyl, hydroxyl, $(C_1-C_4)$-alkoxy, oxo, amino, mono- and di-$(C_1-C_4)$-alkyl-amino,
where $(C_1-C_4)$-alkyl for its part may be substituted by hydroxyl or $(C_1-C_4)$-alkoxy,
$R^{13}$ represents hydrogen or $(C_1-C_4)$-alkyl
and
$R^{14}$ represents $(C_1-C_6)$-alkyl, $(C_3-C_6)$-cycloalkyl, phenyl or 5- or 6-membered heteroaryl,
where $(C_1-C_6)$-alkyl may be substituted by fluorine, chlorine, hydroxyl, $(C_1-C_4)$-alkoxy, mono- or di-$(C_1-C_4)$-alkylamino
and
phenyl and 5- or 6-membered heteroaryl for their part may be substituted up to two times by identical or different substituents from the group consisting of fluorine, chlorine, cyano, $(C_1-C_4)$-alkyl, trifluoromethyl, $(C_1-C_4)$-alkoxy and trifluoromethoxy,
$R^3$ represents $(C_1-C_6)$-alkyl or $(C_2-C_6)$-alkenyl, each of which may be substituted by hydroxyl, $(C_1-C_4)$-alkoxy, amino, mono- or di-$(C_1-C_4)$-alkylamino, hydroxycarbonyl, $(C_1-C_4)$-alkoxycarbonyl, aminocarbonyl or mono- or di-$(C_1-C_4)$-alkylaminocarbonyl,
or
represents a group of the formula $-L^3-R^{15}$ in which
$L^3$ represents a bond or $(C_1-C_4)$-alkanediyl
and
$R^{15}$ represents $(C_3-C_7)$-cycloalkyl, 4- to 7-membered heterocyclyl, phenyl or 5- or 6-membered heteroaryl,
where $(C_3-C_7)$-cycloalkyl and 4- to 7-membered heterocyclyl for their part may be substituted up to two times by identical or different substituents from the group consisting of $(C_1-C_4)$-alkyl, oxo, hydroxyl and $(C_1-C_4)$-alkoxy
and
phenyl and 5- or 6-membered heteroaryl for their part may be substituted up to two times by identical or different substituents from the group consisting of fluorine, chlorine, cyano, $(C_1-C_4)$-alkyl, trifluoromethyl, $(C_1-C_4)$-alkoxy, trifluoromethoxy and amino,
$R^4$ represents nitro or trifluoromethyl
and
$R^5$ represents hydrogen, fluorine or chlorine,
or a salt thereof.

2. The compound according to claim 1 in which
A represents CH,
$R^1$ represents hydrogen, fluorine, chlorine, cyano, nitro, $(C_1-C_4)$-alkyl, difluoromethyl, trifluoromethyl, $(C_1-C_4)$-alkoxy, difluoromethoxy, trifluoromethoxy, amino, mono- or di-$(C_1-C_4)$-alkylamino
or
represents a group of the formula $-NH-C(=O)-R^6$, $-NH-SO_2-R^7$ or $-SO_2-R^8$ in which
$R^6$ and $R^7$ each represent $(C_1-C_4)$-alkyl
and
$R^8$ represents $(C_1-C_4)$-alkyl which may be substituted by hydroxyl, $(C_1-C_4)$-alkoxy, hydroxycarbonyl, aminocarbonyl, $(C_3-C_6)$-cycloalkyl or phenyl, or represents $(C_3-C_6)$-cycloalkyl or phenyl,
where the mentioned phenyl groups may be substituted up to two times by identical or different substituents from the group consisting of fluorine, chlorine, cyano, methyl, trifluoromethyl, methoxy and trifluoromethoxy,
$R^2$ represents hydrogen, $(C_1-C_4)$-alkyl or $(C_2-C_4)$-alkenyl
or
represents a group of the formula $-L^1-C(=O)-O-R^{10}$, $-L^2-C(=O)-NR^{11}R^{12}$ or
$-L^2-SO_2-R^{14}$ in which
$L^1$ represents methylene or ethane-1,2-diyl,
$L^2$ represents a bond, methylene, ethane-1,1-diyl or ethane-1,2-diyl,
$R^{10}$ represents hydrogen or $(C_1-C_4)$-alkyl,
$R^{11}$ represents hydrogen or $(C_1-C_4)$-alkyl which may be substituted by hydroxyl or $(C_1-C_4)$-alkoxy,
$R^{12}$ represents hydrogen, $(C_1-C_6)$-alkyl or $(C_3-C_6)$-cycloalkyl,
where $(C_1-C_6)$-alkyl may be substituted up to two times by identical or different substituents from the group consisting of hydroxyl, $(C_1-C_4)$-alkoxy, hydroxycarbonyl, $(C_1-C_4)$-alkoxycarbonyl and aminocarbonyl and where in $(C_1-C_6)$-alkyl a $CH_2$ group may be exchanged for an oxygen atom if this results in a chemically stable compound,
or
$R^{11}$ and $R^{12}$ together with the nitrogen atom to which they are attached form a 5- or 6-membered heterocycle which may contain a further ring heteroatom from the group consisting of N, O and S and which may be substituted by $(C_1-C_4)$-alkyl, hydroxyl, $(C_1-C_4)$-alkoxy or
oxo,
where $(C_1-C_4)$-alkyl for its part may be substituted by hydroxy or $(C_1-C_4)$-alkoxy,
and
$R^{14}$ represents $(C_1-C_4)$-alkyl, $(C_3-C_6)$-cycloalkyl or phenyl,
where phenyl may be substituted up to two times by identical or different substituents from the group consisting of fluorine, chlorine, cyano, methyl, trifluoromethyl, methoxy and trifluoro-methoxy,
$R^3$ represents $(C_1-C_4)$-alkyl which may be substituted by hydroxyl, $(C_1-C_4)$-alkoxy, hydroxycarbonyl, $(C_1-C_4)$-alkoxycarbonyl, aminocarbonyl, mono-or di-$(C_1-C_4)$-alkylaminocarbonyl or 5- or 6-membered heteroaryl,
represents $(C_2-C_4)$-alkenyl
or
represents a group of the formula $-L^3-R^{15}$ in which
$L^3$ represents a bond or $(C_1-C_4)$-alkanediyl and R[15] represents (C_3-C_7)-cycloalkyl, 4- to 6-membered heterocyclyl or phenyl,
where 4- to 6-membered heterocyclyl for its part may be substituted by oxo
and
phenyl for its part may be substituted up to two times by identical or different substituents from the group consisting of fluorine, chlorine, cyano, methyl, trifluoromethyl, methoxy and trifluoro-methoxy, R[4] represents trifluoromethyl
and
R[5] represents hydrogen or fluorine,
or a salt thereof.

3. The compound according to claim 1 in which
A represents CH,
R[1] represents hydrogen, fluorine, chlorine, nitro, methyl, difluoromethyl, trifluoromethyl, methoxy, trifluoromethoxy or a group of the formula $-SO_2-R^8$ in which
R[8] represents (C_1-C_4)-alkyl which may be substituted by hydroxyl, methoxy or ethoxy,
R[2] represents hydrogen, (C_1-C_4)-alkyl or a group of the formula $-CH_2-C(=O)-O-R^{10}$ or $-CH_2-C(=O)-NR^{11}R^{12}$ in which
R[10] represents (C_1-C_4)-alkyl,
R[11] represents hydrogen or methyl,
R[12] represents hydrogen or (C_1-C_4)-alkyl which may be substituted by hydroxyl, methoxy or ethoxy
or
R[11] and R[12] together with the nitrogen atom to which they are attached form a pyrrolidino, piperidino or morpholino ring,
R[3] represents (C_1-C_4)-alkyl which may be substituted by hydroxyl, pyrrolidino, piperidino, morpholino or pyridyl, represents allyl or represents a group of the formula -L^3-R^{15} in which
L[3] represents a bond, methylene or ethane-1,2-diyl
and
R[15] represents (C_3-C_7)-cycloalkyl or phenyl,
where phenyl for its part may be substituted up to two times by identical or different substituents from the group consisting of fluorine, chlorine, cyano, methyl and trifluoromethyl, R[4] represents trifluoromethyl
and
R[5] represents hydrogen,
or a salt thereof.

4. The compound according to claim 1 in which
A represents CH,
R[1] represents hydrogen, trifluoromethyl or methylsulphonyl,
R[2] represents hydrogen or a group of the formula $-CH_2-C(=O)-NR^{11}R^{12}$ in which
R[11] and R[12] independently of one another represent hydrogen or methyl
or
R[11] and R[12] together with the nitrogen atom to which they are attached form a pyrrolidino ring,
R[3] represents methyl, ethyl, 2-hydroxyethyl or 2-(morpholin-4-yl)ethyl,
R[4] represents trifluoromethyl
and
R[5] represents hydrogen,
or a salt thereof.

5. (rac)-4-{7-Methyl-2,5-dioxo-1-[3-(trifluoromethyl)phenyl]-1,2,3,4,5,6,7,8- octahydropyrimido [4,5-d]pyridazin-4-yl}-3-(methylsulphonyl)benzonitrile, as represented by:

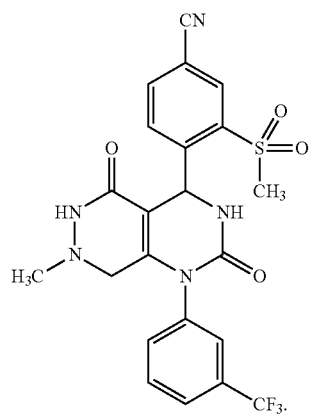 [SMILES: CN1CC2=C(C(=O)N1)C(c1ccc(C#N)cc1S(C)(=O)=O)NC(=O)N2c1cccc(C(F)(F)F)c1]

6. 4-{(4S)-7-Methyl-2,5-dioxo-1-[3-trifluoromethyl)phenyl]-1,2,3,4,5,6,7,8- octahydropyrimido-[4,5 d]pyridazin-4-yl}-3-(methylsulphonyl)benzonitrile, as represented by:

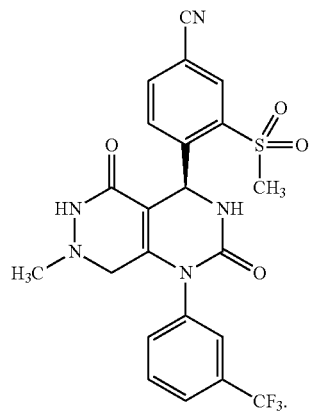 [SMILES: CN1CC2=C(C(=O)N1)[C@@H](c1ccc(C#N)cc1S(C)(=O)=O)NC(=O)N2c1cccc(C(F)(F)F)c1]

7. A composition comprising a compound as defined in claim 1 and one or more inert non-toxic pharmaceutically acceptable auxiliaries.

8. A composition comprising a compound as defined in claim 1. and one or more additional active compounds selected from kinase inhibitors, stimulators and activators of soluble guanylate cyclase, prostacyclin analogs, endothelin receptor antagonists, phosphodiesterase inhibitors, beta-adrenergic receptor agonists, matrix metalloprotease inhibitors, serotonin antagonists, anticholinergics and glucocorticoids.

9. A process for preparing compounds of the formula (I) as defined in claim 1, wherein a compound of the formula (II)

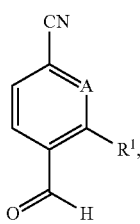
(II)

in which A and R$^1$ have the meanings given in claim 1
is condensed in the presence of an acid or an acid anhydride in a 3-component one-pot reaction or sequentially with an acetoacetic ester of the formula (III)

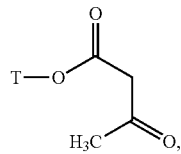
(III)

in which
T represents methyl or ethyl,
and a phenylurea derivative of the formula (IV)

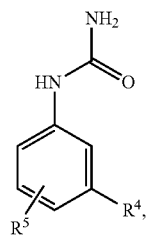
(IV)

in which R$^4$ and R$^5$ have the meanings given in claim 1,
to give a compound of the formula (V-A)

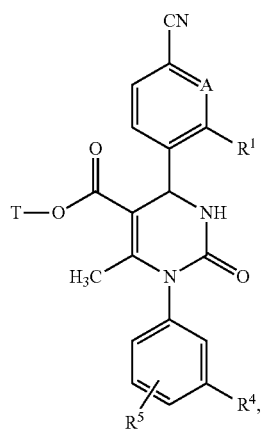
(V-A)

in which A, T, R$^1$, R$^4$ and R$^5$ each have the meanings given above, and this compound is then
[A] in the case that R$^2$ in formula (I) represents hydrogen, brominated in an inert solvent to give a compound of the formula (VI-A)

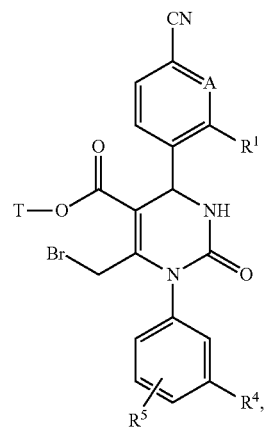
(VI-A)

in which A, T, R$^1$, R$^4$ and R$^5$ each have the meanings given above,
and subsequently reacted with a hydrazine derivative of the formula (VII)

R$^3$—NH—NH$_2$ (VII), in which R$^3$ has the meaning given in claim 1,
with formation of a six-membered ring to give a compound of the formula (I-A)

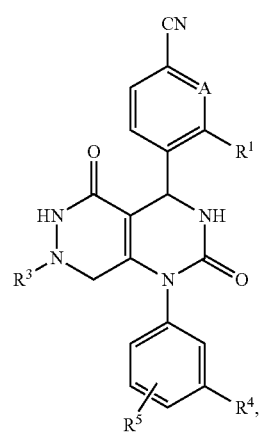
(I-A)

in which A, R$^1$, R$^3$, R$^4$ and R$^5$ each have the meanings given above,
or
[B] in the case that R$^2$ in formula (I) is different from hydrogen, initially reacted with a compound of the formula (VIII)

R$^{2A}$—X (VIII), in which
R$^{2A}$ has the meaning of R$^2$ given in claim 1, but does not represent hydrogen,
and
X represents a leaving group such as, for example, halogen, mesylate, tosylate or triflate,
in the presence of a base to give a compound of the formula (V-B)

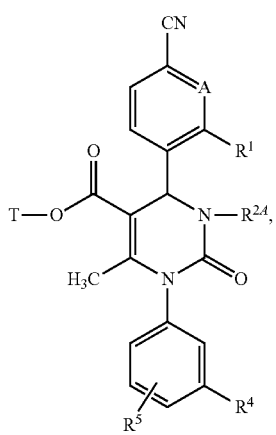

(V-B)

in which A, T, $R^1$, $R^{2A}$, $R^4$ and $R^5$ each have the meanings given above,
then brominated in an inert solvent to give a compound of the formula (VI-B)

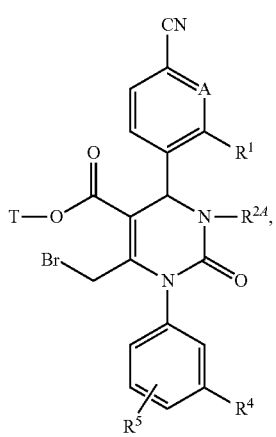

(VI-B)

in which A, T, $R^1$, $R^{2A}$, $R^4$ and $R^5$ each have the meanings given above,
and subsequently reacted with a hydrazine derivative of the formula (VII)

$$R^3\text{—NH—NH}_2 \quad (VII),$$

in which $R^3$ has the meaning given in claim 1,
with cyclization to give a compound of the formula (I-B)

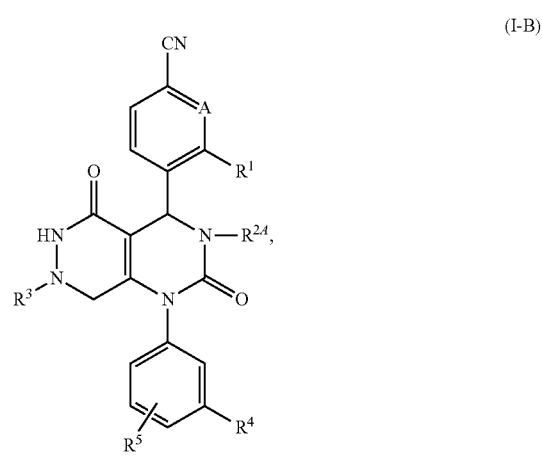

(I-B)

in which A, $R^1$, $R^{2A}$, $R^3$, $R^4$ and $R^5$ each have the meanings given above,
and the compound of the formula (I-A) or (I-B) is optionally separated into its enantiomers and/or diastereomers and/or converted with the appropriate (i) solvents and/or (ii) bases or acids into a salt thereof.

\* \* \* \* \*